US012746144B2

(12) United States Patent
Martin et al.

(10) Patent No.: US 12,746,144 B2
(45) Date of Patent: Sep. 29, 2026

(54) URINE COLLECTION CONTAINER BAFFLE STRUCTURES, AND RELATED SYSTEMS AND METHODS

(71) Applicant: PUREWICK CORPORATION, Covington, GA (US)

(72) Inventors: Adam Martin, Holly Springs, NC (US); Richard Abbott, Raleigh, NC (US); Nicholas Jardine, Holly Springs, NC (US)

(73) Assignee: PUREWICK CORPORATION, Covington, GA (US)

( * ) Notice: Subject to any disclaimer, the term of this patent is extended or adjusted under 35 U.S.C. 154(b) by 367 days.

(21) Appl. No.: 18/558,502

(22) PCT Filed: May 24, 2022

(86) PCT No.: PCT/US2022/030685
§ 371 (c)(1),
(2) Date: Nov. 1, 2023

(87) PCT Pub. No.: WO2022/251184
PCT Pub. Date: Dec. 1, 2022

(65) Prior Publication Data

US 2024/0268989 A1 Aug. 15, 2024

Related U.S. Application Data

(60) Provisional application No. 63/193,235, filed on May 26, 2021.

(51) Int. Cl.
*A61F 5/451* (2006.01)
*A61F 5/44* (2006.01)

(52) U.S. Cl.
CPC ............ *A61F 5/451* (2013.01); *A61F 5/4404* (2013.01)

(58) Field of Classification Search
CPC ............ A61M 1/60; A61M 2202/0496; A61M 2205/42; A61F 5/451; A61F 5/4404
See application file for complete search history.

(56) References Cited

U.S. PATENT DOCUMENTS

| | | | |
|---|---|---|---|
| 737,443 | A | 8/1903 | Mooers |
| 976,883 | A | 11/1910 | Keagy et al. |

(Continued)

FOREIGN PATENT DOCUMENTS

| | | | |
|---|---|---|---|
| AU | 2018216821 | A1 | 8/2019 |
| AU | 2021299304 | A1 | 2/2023 |

(Continued)

OTHER PUBLICATIONS

US 9,908,683 B2, 03/2018, Sandhausen et al. (withdrawn)

(Continued)

*Primary Examiner* — Susan S Su
*Assistant Examiner* — Erin A Kim
(74) *Attorney, Agent, or Firm* — Ballard Spahr LLP

(57) ABSTRACT

Examples relate to urine collection container baffle structures, and related systems and methods. A urine collection system includes a urine collection device, a conduit, a canister, and a baffle structure. The urine collection device is configured to be positioned at least proximate to a urethra of a user. The conduit is in fluid communication with the urine collection device. The canister has an interior region, and the baffle structure is positioned or positionable in the interior region of the canister.

38 Claims, 6 Drawing Sheets

(56) References Cited

U.S. PATENT DOCUMENTS 1,015,905 A 1/1912 Northrop
1,032,841 A 7/1912 Koenig
1,178,644 A * 4/1916 Johnson .................. A61F 5/455 604/350
1,229,423 A 6/1917 Eckenrode
1,387,726 A 8/1921 Karge
1,742,080 A 12/1929 Jones
1,979,899 A 11/1934 Obrien et al.
2,241,010 A 5/1941 Chipley
2,262,772 A 11/1941 Peder
2,326,881 A 8/1943 Packer
2,379,346 A 6/1945 Farrell
2,485,555 A 10/1949 Bester
2,571,357 A 10/1951 Charles
2,613,670 A 10/1952 Edward
2,616,426 A 11/1952 Adele
2,644,234 A 7/1953 Earl
2,648,335 A 8/1953 Chambers
2,789,560 A 4/1957 Weimer
2,859,786 A 11/1958 Tupper
2,944,551 A 7/1960 Carl
2,968,046 A 1/1961 Duke
2,971,512 A 2/1961 Reinhardt
3,032,038 A 5/1962 Swinn
3,077,883 A 2/1963 Hill
3,087,938 A 4/1963 Hans et al.
3,114,916 A 12/1963 Hadley
3,169,528 A 2/1965 Knox et al.
3,171,506 A 3/1965 Therkel
3,175,719 A 3/1965 Herndon
3,194,238 A 7/1965 Breece
3,198,994 A 8/1965 Hildebrandt et al.
3,221,742 A 12/1965 Egon
3,312,221 A 4/1967 Overment
3,312,981 A 4/1967 Mcguire et al.
3,349,768 A 10/1967 Keane
3,356,091 A 12/1967 Patterson
3,362,590 A 1/1968 Gene
3,366,116 A 1/1968 Huck
3,368,564 A 2/1968 Selix
3,369,940 A 2/1968 Slautterback
3,398,848 A 8/1968 Donovan
3,400,717 A 9/1968 Bruce et al.
3,406,688 A 10/1968 Bruce
3,411,504 A 11/1968 Glassman
3,424,163 A 1/1969 Gravdahl
3,425,471 A 2/1969 Yates
3,434,565 A 3/1969 Fischer
3,447,536 A 6/1969 Snyder
3,511,241 A 5/1970 Lee
3,512,185 A 5/1970 Ellis
3,520,300 A 7/1970 Flower
3,528,423 A 9/1970 Lee
3,608,552 A 9/1971 Broerman
3,613,123 A 10/1971 Langstrom
3,648,700 A 3/1972 Warner
3,651,810 A 3/1972 Ormerod
3,661,155 A 5/1972 Lindan
3,683,918 A 8/1972 Pizzella
3,699,815 A 10/1972 Holbrook
3,720,554 A 3/1973 Stumpf
3,721,243 A 3/1973 Greth et al.
3,726,277 A 4/1973 Hirschman
3,727,788 A 4/1973 Holbrook
3,742,952 A 7/1973 Magers et al.
3,742,953 A 7/1973 Lee
3,757,355 A 9/1973 Allen et al.
3,788,324 A 1/1974 Lim
3,843,016 A 10/1974 Bornhorst et al.
3,863,638 A 2/1975 Rogers et al.
3,863,798 A 2/1975 Kurihara et al.
3,864,759 A 2/1975 Horiuchi
3,865,109 A 2/1975 Elmore et al.
3,881,486 A 5/1975 Fenton
3,881,489 A 5/1975 Hartwell
3,915,189 A 10/1975 Holbrook et al.
3,931,650 A 1/1976 Miller
3,931,819 A 1/1976 Weedle
3,964,786 A 6/1976 Mashuda
3,998,228 A 12/1976 Poidomani
3,999,550 A 12/1976 Martin
4,006,793 A 2/1977 Robinson
4,015,604 A 4/1977 Csillag
4,020,843 A 5/1977 Kanall
4,022,211 A 5/1977 Timmons et al.
4,022,213 A 5/1977 Stein
4,023,216 A 5/1977 Li
4,027,776 A 6/1977 Douglas
4,031,897 A 6/1977 Graetz
4,042,337 A * 8/1977 Griffith ................ A61B 10/007 4/144.1
4,064,962 A 12/1977 Hunt
4,069,817 A 1/1978 Fenole et al.
4,084,589 A 4/1978 Kulvi
4,096,897 A 6/1978 Cammarata
4,116,197 A 9/1978 Bermingham
4,140,739 A 2/1979 Cotten
4,180,178 A 12/1979 Turner
4,187,953 A 2/1980 Turner
4,194,508 A 3/1980 Anderson
4,197,849 A 4/1980 Bostick
4,200,102 A 4/1980 Duhamel et al.
4,202,058 A 5/1980 Anderson
4,203,503 A 5/1980 Bertotti et al.
4,209,076 A 6/1980 Bertotti et al.
D255,935 S 7/1980 Cullis et al.
4,223,677 A 9/1980 Anderson
4,233,025 A 11/1980 Larson et al.
4,233,978 A 11/1980 Hickey
4,246,901 A 1/1981 Frosch et al.
4,253,542 A 3/1981 Ruspa et al.
4,257,418 A 3/1981 Hessner
4,270,539 A 6/1981 Frosch et al.
4,280,498 A 7/1981 Jensen
4,281,655 A 8/1981 Terauchi
4,292,916 A 10/1981 Bradley et al.
4,330,239 A 5/1982 Gannaway
4,345,341 A 8/1982 Saito
4,349,029 A 9/1982 Mott
4,352,356 A 10/1982 Tong
4,356,012 A 10/1982 Hofstetter
4,360,933 A 11/1982 Kimura et al.
4,365,363 A 12/1982 Windauer
4,372,299 A 2/1983 Fixel
4,375,841 A 3/1983 Vielbig
4,387,726 A 6/1983 Denard
4,403,991 A 9/1983 Hill
4,421,511 A 12/1983 Steer et al.
4,425,130 A 1/1984 Desmarais
4,446,986 A 5/1984 Bowen et al.
4,453,938 A 6/1984 Brendling
4,457,314 A 7/1984 Knowles
4,457,758 A 7/1984 Norton
4,476,879 A 10/1984 Jackson
4,512,771 A 4/1985 Norton
4,526,688 A 7/1985 Schmidt et al.
4,528,703 A 7/1985 Kraus
4,533,354 A 8/1985 Jensen
4,533,357 A 8/1985 Hall
D280,438 S 9/1985 Wendt
4,551,141 A 11/1985 Mcneil
4,553,968 A 11/1985 Komis
4,568,341 A 2/1986 Mitchell et al.
4,581,026 A 4/1986 Schneider
4,583,983 A 4/1986 Einhorn et al.
4,589,516 A 5/1986 Inoue et al.
4,601,716 A 7/1986 Smith
4,610,675 A 9/1986 Triunfol
4,620,333 A 11/1986 Ritter
4,626,250 A 12/1986 Schneider
4,627,846 A 12/1986 Ternstroem
4,631,061 A 12/1986 Martin
4,650,477 A 3/1987 Johnson
4,655,754 A 4/1987 Richmond et al.

(56) References Cited

U.S. PATENT DOCUMENTS

| | | | |
|---|---|---|---|
| 4,656,675 | A | 4/1987 | Fajnsztajn |
| 4,681,570 | A | 7/1987 | Dalton |
| 4,681,572 | A | 7/1987 | Tokarz et al. |
| 4,681,577 | A | 7/1987 | Stern et al. |
| 4,692,160 | A | 9/1987 | Nussbaumer |
| 4,707,864 | A | 11/1987 | Ikematsu et al. |
| 4,713,065 | A | 12/1987 | Koot |
| 4,713,066 | A | 12/1987 | Komis |
| 4,723,953 | A | 2/1988 | Pratt et al. |
| 4,735,841 | A | 4/1988 | Sourdet |
| 4,743,236 | A | 5/1988 | Manschot |
| 4,747,166 | A | 5/1988 | Kuntz |
| 4,752,944 | A | 6/1988 | Conrads et al. |
| 4,759,753 | A | 7/1988 | Schneider et al. |
| 4,769,215 | A | 9/1988 | Ehrenkranz |
| 4,771,484 | A | 9/1988 | Mozell |
| 4,772,280 | A | 9/1988 | Rooyakkers |
| 4,775,458 | A | 10/1988 | Forester |
| 4,784,654 | A | 11/1988 | Beecher |
| 4,790,830 | A | 12/1988 | Hamacher |
| 4,790,835 | A | 12/1988 | Elias |
| 4,791,686 | A | 12/1988 | Taniguchi et al. |
| 4,795,449 | A | 1/1989 | Schneider et al. |
| 4,798,603 | A | 1/1989 | Meyer et al. |
| 4,799,928 | A | 1/1989 | Crowley |
| 4,804,377 | A | 2/1989 | Hanifl et al. |
| 4,812,053 | A | 3/1989 | Bhattacharjee |
| 4,813,943 | A | 3/1989 | Smith |
| 4,820,291 | A | 4/1989 | Terauchi et al. |
| 4,820,297 | A | 4/1989 | Kaufman et al. |
| 4,841,728 | A | 6/1989 | Jean et al. |
| 4,846,818 | A | 7/1989 | Keldahl et al. |
| 4,846,819 | A | 7/1989 | Welch |
| 4,846,824 | A | 7/1989 | Lassen et al. |
| 4,846,909 | A | 7/1989 | Klug et al. |
| 4,857,064 | A | 8/1989 | Mendoza |
| 4,865,595 | A | 9/1989 | Heyden |
| 4,872,299 | A | 10/1989 | Troutner et al. |
| 4,875,898 | A | 10/1989 | Eakin |
| 4,880,417 | A | 11/1989 | Yabrov et al. |
| 4,882,794 | A | 11/1989 | Stewart |
| 4,883,465 | A | 11/1989 | Brennan |
| 4,886,498 | A | 12/1989 | Newton |
| 4,886,508 | A | 12/1989 | Washington |
| 4,886,509 | A | 12/1989 | Mattsson |
| 4,889,532 | A | 12/1989 | Metz et al. |
| 4,889,533 | A | 12/1989 | Beecher |
| 4,890,691 | A | 1/1990 | Ching-Ho |
| 4,895,140 | A | 1/1990 | Bellak |
| 4,903,254 | A | 2/1990 | Haas |
| 4,904,248 | A | 2/1990 | Vaillancourt |
| D306,759 | S | 3/1990 | D'Alo |
| 4,905,692 | A | 3/1990 | More |
| 4,911,262 | A | 3/1990 | Tani et al. |
| 4,930,997 | A | 6/1990 | Bennett |
| 4,936,838 | A | 6/1990 | Cross et al. |
| 4,950,262 | A | 8/1990 | Takagi |
| 4,955,922 | A | 9/1990 | Terauchi |
| 4,957,487 | A | 9/1990 | Gerow |
| 4,965,460 | A | 10/1990 | Tanaka et al. |
| 4,986,823 | A | 1/1991 | Anderson et al. |
| 4,987,849 | A | 1/1991 | Sherman |
| 5,002,541 | A | 3/1991 | Conkling et al. |
| 5,004,463 | A | 4/1991 | Nigay |
| 5,013,308 | A | 5/1991 | Sullivan et al. |
| 5,030,229 | A | 7/1991 | Yang |
| 5,031,248 | A | 7/1991 | Kemper |
| 5,045,077 | A | 9/1991 | Blake |
| 5,045,283 | A | 9/1991 | Patel |
| 5,049,144 | A | 9/1991 | Payton |
| 5,053,339 | A | 10/1991 | Patel |
| 5,057,092 | A | 10/1991 | Webster |
| 5,058,088 | A | 10/1991 | Haas et al. |
| 5,071,347 | A | 12/1991 | Mcguire |
| 5,078,707 | A | 1/1992 | Peter |
| 5,084,037 | A | 1/1992 | Barnett |
| 5,100,396 | A | 3/1992 | Zamierowski |
| 5,102,404 | A | 4/1992 | Goldberg et al. |
| 5,112,324 | A | 5/1992 | Wallace |
| 5,134,994 | A | 8/1992 | Say |
| 5,137,033 | A | 8/1992 | Norton |
| 5,147,301 | A | 9/1992 | Ruvio |
| 5,176,667 | A | 1/1993 | Debring |
| 5,195,997 | A | 3/1993 | Carns |
| 5,196,654 | A | 3/1993 | Diflora et al. |
| 5,199,444 | A | 4/1993 | Wheeler |
| 5,203,699 | A | 4/1993 | Mcguire |
| 5,234,419 | A | 8/1993 | Bryant et al. |
| 5,244,458 | A | 9/1993 | Takasu |
| 5,246,454 | A | 9/1993 | Peterson |
| 5,267,988 | A | 12/1993 | Farkas |
| 5,275,307 | A | 1/1994 | Freese |
| 5,282,795 | A | 2/1994 | Finney |
| 5,295,979 | A | 3/1994 | DeLaurentis et al. |
| 5,295,983 | A | 3/1994 | Kubo |
| 5,300,052 | A | 4/1994 | Kubo |
| 5,304,749 | A | 4/1994 | Crandell |
| 5,312,383 | A | 5/1994 | Kubalak |
| 5,318,550 | A | 6/1994 | Cermak et al. |
| 5,330,457 | A | 7/1994 | Cohen |
| 5,330,459 | A | 7/1994 | Lavon et al. |
| 5,334,174 | A | 8/1994 | Street |
| 5,334,176 | A | 8/1994 | Buenger et al. |
| 5,340,840 | A | 8/1994 | Park et al. |
| D354,129 | S | 1/1995 | Salvadori |
| D354,560 | S | 1/1995 | Chase |
| 5,382,244 | A | 1/1995 | Telang |
| 5,397,315 | A | 3/1995 | Schmidt et al. |
| 5,409,014 | A | 4/1995 | Napoli et al. |
| 5,409,475 | A | 4/1995 | Steer |
| 5,411,495 | A | 5/1995 | Willingham |
| 5,423,784 | A | 6/1995 | Metz |
| 5,423,788 | A | 6/1995 | Rollins et al. |
| 5,437,836 | A | 8/1995 | Yamada |
| 5,455,091 | A | 10/1995 | Oreglia et al. |
| 5,456,246 | A | 10/1995 | Schmieding et al. |
| 5,466,229 | A | 11/1995 | Elson et al. |
| 5,478,334 | A | 12/1995 | Bernstein |
| 5,499,977 | A | 3/1996 | Marx |
| 5,525,407 | A | 6/1996 | Yang |
| 5,543,042 | A | 8/1996 | Filan et al. |
| D373,928 | S | 9/1996 | Green |
| 5,582,604 | A | 12/1996 | Ahr et al. |
| 5,592,950 | A | 1/1997 | Kopelowicz |
| 5,593,389 | A | 1/1997 | Chang |
| 5,605,161 | A | 2/1997 | Cross |
| 5,614,699 | A | 3/1997 | Yashiro et al. |
| 5,618,277 | A | 4/1997 | Goulter |
| 5,628,735 | A | 5/1997 | Skow |
| 5,632,736 | A | 5/1997 | Block |
| 5,636,643 | A | 6/1997 | Argenta et al. |
| 5,637,104 | A | 6/1997 | Ball et al. |
| D380,543 | S | 7/1997 | Piontek et al. |
| 5,662,633 | A | 9/1997 | Doak et al. |
| 5,674,212 | A | 10/1997 | Osborn et al. |
| 5,678,564 | A | 10/1997 | Lawrence et al. |
| 5,681,297 | A | 10/1997 | Hashimoto et al. |
| 5,687,429 | A | 11/1997 | Rahlff |
| 5,695,485 | A | 12/1997 | Duperret et al. |
| 5,695,487 | A | 12/1997 | Cohen et al. |
| 5,700,254 | A | 12/1997 | Mcdowall et al. |
| 5,701,612 | A | 12/1997 | Daneshvar |
| 5,705,777 | A | 1/1998 | Flanigan et al. |
| 5,735,835 | A | 4/1998 | Holland |
| 5,735,837 | A | 4/1998 | Ishikawa |
| 5,752,944 | A | 5/1998 | Dann et al. |
| 5,763,333 | A | 6/1998 | Suzuki et al. |
| 5,772,644 | A | 6/1998 | Bark et al. |
| 5,792,132 | A | 8/1998 | Garcia |
| 5,827,243 | A | 10/1998 | Palestrant |
| 5,827,247 | A | 10/1998 | Kay |
| 5,827,250 | A | 10/1998 | Fujioka et al. |
| 5,827,257 | A | 10/1998 | Fujioka et al. |
| D401,699 | S | 11/1998 | Herchenbach et al. |

(56) References Cited

U.S. PATENT DOCUMENTS

| | | | |
|---|---|---|---|
| 5,859,393 | A | 1/1999 | Cummins et al. |
| 5,865,378 | A | 2/1999 | Hollinshead et al. |
| 5,873,869 | A | 2/1999 | Hammons et al. |
| 5,876,393 | A | 3/1999 | Ahr et al. |
| 5,887,291 | A | 3/1999 | Bellizzi |
| 5,891,125 | A | 4/1999 | Plumley |
| 5,894,608 | A | 4/1999 | Birbara |
| 5,895,349 | A | 4/1999 | Tihon |
| D409,303 | S | 5/1999 | Oepping |
| 5,911,222 | A | 6/1999 | Lawrence et al. |
| 5,956,782 | A | 9/1999 | Olguin |
| 5,957,904 | A | 9/1999 | Holland |
| 5,968,026 | A | 10/1999 | Osborn et al. |
| 5,972,505 | A | 10/1999 | Phillips et al. |
| 6,007,524 | A | 12/1999 | Schneider |
| 6,007,526 | A | 12/1999 | Passalaqua et al. |
| D421,307 | S | 2/2000 | Harmanoglu |
| 6,039,060 | A | 3/2000 | Rower |
| 6,050,983 | A | 4/2000 | Moore et al. |
| 6,059,762 | A | 5/2000 | Boyer et al. |
| 6,063,064 | A | 5/2000 | Tuckey et al. |
| 6,098,625 | A | 8/2000 | Winkler |
| 6,105,174 | A | 8/2000 | Karlsten et al. |
| 6,113,582 | A | 9/2000 | Dwork |
| 6,117,163 | A | 9/2000 | Bierman |
| 6,123,398 | A | 9/2000 | Arai et al. |
| 6,129,718 | A | 10/2000 | Wada et al. |
| 6,131,964 | A | 10/2000 | Sareshwala |
| 6,152,902 | A | 11/2000 | Christian et al. |
| 6,164,569 | A | 12/2000 | Hollinshead et al. |
| 6,177,606 | B1 | 1/2001 | Etheredge et al. |
| 6,209,142 | B1 | 4/2001 | Mattsson et al. |
| 6,220,050 | B1 | 4/2001 | Cooksey |
| 6,244,311 | B1 | 6/2001 | Hand et al. |
| 6,248,096 | B1 | 6/2001 | Dwork et al. |
| 6,263,887 | B1 | 7/2001 | Dunn |
| 6,283,246 | B1 | 9/2001 | Nishikawa |
| 6,296,627 | B1 | 10/2001 | Edwards |
| 6,311,339 | B1 | 11/2001 | Kraus |
| 6,316,688 | B1 | 11/2001 | Hammons et al. |
| 6,336,919 | B1 | 1/2002 | Davis et al. |
| 6,338,729 | B1 | 1/2002 | Wada et al. |
| 6,352,525 | B1 | 3/2002 | Wakabayashi |
| 6,394,988 | B1 | 5/2002 | Hashimoto |
| 6,395,956 | B1 | 5/2002 | Glasgow et al. |
| 6,398,742 | B1 | 6/2002 | Kim |
| 6,406,463 | B1 | 6/2002 | Brown |
| 6,409,712 | B1 | 6/2002 | Dutari et al. |
| 6,415,888 | B2 | 7/2002 | An et al. |
| 6,416,500 | B1 | 7/2002 | Wada et al. |
| 6,417,750 | B1 | 7/2002 | Sohn |
| 6,423,045 | B1 | 7/2002 | Wise et al. |
| 6,428,521 | B1 | 8/2002 | Droll |
| 6,428,522 | B1 | 8/2002 | Dipalma et al. |
| 6,446,454 | B1 | 9/2002 | Lee et al. |
| 6,461,340 | B1 | 10/2002 | Lenker et al. |
| 6,467,570 | B1 | 10/2002 | Herold |
| 6,475,198 | B1 | 11/2002 | Lipman et al. |
| 6,479,726 | B1 | 11/2002 | Cole et al. |
| 6,491,673 | B1 | 12/2002 | Palumbo et al. |
| 6,508,794 | B1 | 1/2003 | Palumbo et al. |
| 6,524,292 | B1 | 2/2003 | Dipalma et al. |
| 6,526,603 | B1 | 3/2003 | Murphy |
| 6,540,729 | B1 | 4/2003 | Wada et al. |
| 6,547,771 | B2 | 4/2003 | Robertson et al. |
| 6,551,293 | B1 | 4/2003 | Mitchell |
| 6,569,133 | B2 | 5/2003 | Cheng et al. |
| D476,518 | S | 7/2003 | Doppelt |
| 6,592,560 | B2 | 7/2003 | Snyder et al. |
| 6,610,038 | B1 | 8/2003 | Dipalma et al. |
| 6,618,868 | B2 | 9/2003 | Minnick |
| 6,620,142 | B1 | 9/2003 | Flueckiger |
| 6,629,651 | B1 | 10/2003 | Male et al. |
| 6,635,037 | B1 | 10/2003 | Bennett |
| 6,635,038 | B2 | 10/2003 | Scovel |
| 6,652,495 | B1 | 11/2003 | Walker |
| 6,666,850 | B1 | 12/2003 | Ahr et al. |
| 6,685,684 | B1 | 2/2004 | Falconer |
| 6,695,828 | B1 | 2/2004 | Dipalma et al. |
| 6,699,174 | B1 | 3/2004 | Bennett |
| 6,700,034 | B1 | 3/2004 | Lindsay et al. |
| 6,702,793 | B1 | 3/2004 | Sweetser et al. |
| 6,706,027 | B2 | 3/2004 | Harvie et al. |
| 6,732,384 | B2 | 5/2004 | Scott |
| 6,736,977 | B1 | 5/2004 | Hall et al. |
| 6,740,066 | B2 | 5/2004 | Wolff et al. |
| 6,764,477 | B1 | 7/2004 | Chen et al. |
| 6,783,519 | B2 | 8/2004 | Samuelsson |
| 6,796,974 | B2 | 9/2004 | Palumbo et al. |
| 6,814,547 | B2 | 11/2004 | Childers et al. |
| 6,848,719 | B2 | 2/2005 | Rowley |
| 6,849,065 | B2 | 2/2005 | Schmidt et al. |
| 6,857,137 | B2 | 2/2005 | Otto |
| 6,878,647 | B1 | 4/2005 | Rezai et al. |
| 6,885,690 | B2 | 4/2005 | Aggerstam et al. |
| 6,888,044 | B2 | 5/2005 | Fell et al. |
| 6,893,425 | B2 | 5/2005 | Dunn et al. |
| 6,912,737 | B2 | 7/2005 | Ernest et al. |
| 6,918,899 | B2 | 7/2005 | Harvie |
| 6,979,324 | B2 | 12/2005 | Bybordi et al. |
| 7,018,366 | B2 | 3/2006 | Easter |
| 7,066,411 | B2 | 6/2006 | Male et al. |
| 7,087,043 | B2 | 8/2006 | Dolan |
| 7,122,023 | B1 | 10/2006 | Hinoki |
| 7,125,399 | B2 | 10/2006 | Miskie |
| 7,131,964 | B2 | 11/2006 | Harvie |
| 7,135,012 | B2 | 11/2006 | Harvie |
| 7,141,043 | B2 | 11/2006 | Harvie |
| D533,972 | S | 12/2006 | La |
| 7,160,273 | B2 | 1/2007 | Greter et al. |
| 7,166,092 | B2 | 1/2007 | Elson et al. |
| 7,171,699 | B2 | 2/2007 | Ernest et al. |
| 7,171,871 | B2 | 2/2007 | Kozak |
| 7,179,951 | B2 | 2/2007 | Krishnaswamy-mirle et al. |
| 7,181,781 | B1 | 2/2007 | Trabold et al. |
| 7,186,245 | B1 | 3/2007 | Cheng et al. |
| 7,192,424 | B2 | 3/2007 | Cooper |
| 7,219,764 | B1 | 5/2007 | Forbes |
| 7,220,250 | B2 | 5/2007 | Suzuki et al. |
| D562,975 | S | 2/2008 | Otto |
| 7,335,189 | B2 | 2/2008 | Harvie |
| 7,358,282 | B2 | 4/2008 | Krueger et al. |
| 7,390,320 | B2 | 6/2008 | Machida et al. |
| 7,438,706 | B2 | 10/2008 | Koizumi et al. |
| 7,488,310 | B2 | 2/2009 | Yang |
| 7,491,194 | B1 | 2/2009 | Oliwa |
| D591,106 | S | 4/2009 | Dominique et al. |
| 7,513,381 | B2 | 4/2009 | Heng et al. |
| 7,520,872 | B2 | 4/2009 | Biggie et al. |
| D593,801 | S | 6/2009 | Wilson et al. |
| 7,540,364 | B2 | 6/2009 | Sanderson |
| 7,549,511 | B2 | 6/2009 | Marocco |
| 7,549,512 | B2 | 6/2009 | Newberry |
| 7,585,293 | B2 | 9/2009 | Vermaak |
| 7,588,560 | B1 | 9/2009 | Dunlop |
| 7,637,905 | B2 | 12/2009 | Saadat et al. |
| 7,658,730 | B2 | 2/2010 | Conley |
| 7,665,359 | B2 | 2/2010 | Barber |
| 7,682,347 | B2 | 3/2010 | Parks et al. |
| 7,687,004 | B2 | 3/2010 | Allen |
| 7,695,459 | B2 | 4/2010 | Gilbert et al. |
| 7,695,460 | B2 | 4/2010 | Wada et al. |
| 7,699,818 | B2 | 4/2010 | Gilbert |
| 7,699,831 | B2 | 4/2010 | Bengtson et al. |
| 7,722,584 | B2 | 5/2010 | Tanaka et al. |
| 7,727,206 | B2 | 6/2010 | Gorres |
| 7,740,620 | B2 | 6/2010 | Gilbert et al. |
| 7,749,205 | B2 | 7/2010 | Tazoe et al. |
| 7,755,497 | B2 | 7/2010 | Wada et al. |
| 7,766,887 | B2 | 8/2010 | Burns et al. |
| 7,803,144 | B1 | 9/2010 | Vollrath |
| D625,407 | S | 10/2010 | Koizumi et al. |
| 7,806,879 | B2 | 10/2010 | Brooks et al. |
| 7,811,272 | B2 | 10/2010 | Lindsay et al. |

(56) References Cited

U.S. PATENT DOCUMENTS 7,815,067 B2 10/2010 Matsumoto et al.
7,833,169 B2 11/2010 Hannon
7,857,806 B2 12/2010 Karpowicz et al.
7,866,942 B2 1/2011 Harvie
7,871,385 B2 1/2011 Levinson et al.
7,875,010 B2 1/2011 Frazier et al.
7,901,389 B2 3/2011 Mombrinie
7,927,320 B2 4/2011 Goldwasser et al.
7,927,321 B2 4/2011 Marland
7,931,634 B2 4/2011 Swiecicki et al.
7,939,706 B2 5/2011 Okabe et al.
7,946,443 B2 5/2011 Stull et al.
7,947,025 B2 5/2011 Buglino et al.
7,963,419 B2 6/2011 Burney et al.
7,976,519 B2 7/2011 Bubb et al.
7,981,087 B2 7/2011 Gesler, III
7,993,318 B2 8/2011 Olsson et al.
8,015,627 B2 9/2011 Baker et al.
8,016,071 B1 9/2011 Martinus et al.
8,028,460 B2 10/2011 Williams
8,047,398 B2 11/2011 Dimartino et al.
8,083,094 B2 12/2011 Caulfield et al.
8,128,608 B2 3/2012 Thevenin
8,156,941 B1 4/2012 Simms
8,167,860 B1 5/2012 Siegel
8,181,651 B2 5/2012 Pinel
8,181,819 B2 5/2012 Burney et al.
8,211,063 B2 7/2012 Bierman et al.
8,221,369 B2 7/2012 Parks et al.
8,241,262 B2 8/2012 Mahnensmith
8,277,426 B2 10/2012 Wilcox et al.
8,287,508 B1 10/2012 Sanchez
8,303,554 B2 11/2012 Tsai et al.
8,322,565 B2 12/2012 Caulfield et al.
8,337,477 B2 12/2012 Parks et al.
D674,241 S 1/2013 Bickert et al.
8,343,122 B2 1/2013 Gorres
8,343,125 B2 1/2013 Kawazoe et al.
8,353,074 B2 1/2013 Krebs
8,353,886 B2 1/2013 Bester et al.
D676,241 S 2/2013 Merrill
8,388,587 B1 3/2013 Gmuer et al.
8,388,588 B2 3/2013 Wada et al.
D679,807 S 4/2013 Burgess et al.
8,425,482 B2 4/2013 Khoubnazar
8,434,586 B2 5/2013 Pawelski et al.
8,449,510 B2 5/2013 Martini et al.
D684,260 S 6/2013 Lund et al.
8,470,230 B2 6/2013 Caulfield et al.
8,479,941 B2 7/2013 Matsumoto et al.
8,479,949 B2 7/2013 Henkel
8,500,719 B1 8/2013 Simpson et al.
8,512,301 B2 8/2013 Ma
8,529,530 B2 9/2013 Koch et al.
8,535,284 B2 9/2013 Joder et al.
8,546,639 B2 10/2013 Wada et al.
8,551,062 B2 10/2013 Kay
8,551,075 B2 10/2013 Bengtson
8,568,376 B2 10/2013 Delattre et al.
D694,404 S 11/2013 Burgess et al.
8,585,683 B2 11/2013 Bengtson et al.
8,652,112 B2 2/2014 Johannison et al.
8,669,412 B2 3/2014 Fernkvist et al.
D702,973 S 4/2014 Norland et al.
8,702,667 B1 4/2014 Johnson
8,703,032 B2 4/2014 Menon et al.
D704,330 S 5/2014 Cicatelli
D704,510 S 5/2014 Mason et al.
D705,423 S 5/2014 Walsh Cutler
D705,926 S 5/2014 Burgess et al.
8,714,394 B2 5/2014 Wulf
8,715,267 B2 5/2014 Bengtson et al.
8,740,852 B2 6/2014 Aviles
8,757,425 B2 6/2014 Copeland
8,777,032 B2 7/2014 Biesecker et al.
8,808,260 B2 8/2014 Koch et al.
8,864,730 B2 10/2014 Conway et al.
8,881,923 B2 11/2014 Higginson
8,882,731 B2 11/2014 Suzuki et al.
8,936,585 B2 1/2015 Carson et al.
D729,581 S 5/2015 Boroski
9,028,460 B2 5/2015 Medeiros
9,056,698 B2 6/2015 Noer
9,078,792 B2 7/2015 Ruiz
9,145,879 B2 9/2015 Pirovano et al.
9,173,602 B2 11/2015 Gilbert
9,173,799 B2 11/2015 Tanimoto et al.
9,187,220 B2 11/2015 Biesecker et al.
9,199,772 B2 12/2015 Krippendorf
9,233,020 B2 1/2016 Matsumiya
9,248,058 B2 2/2016 Conway et al.
9,308,118 B1 4/2016 Dupree et al.
9,309,029 B2 4/2016 Incorvia et al.
9,333,281 B2 5/2016 Giezendanner et al.
9,381,108 B2 7/2016 Longoni et al.
9,382,047 B2 7/2016 Schmidtner et al.
9,402,424 B2 8/2016 Roy
9,415,191 B2 8/2016 Aviles
9,456,937 B2 10/2016 Ellis
9,480,595 B2 11/2016 Baham et al.
9,517,865 B2 12/2016 Albers et al.
D777,941 S 1/2017 Piramoon
9,533,806 B2 1/2017 Ding et al.
9,550,611 B2 1/2017 Hodge
9,555,930 B2 1/2017 Campbell et al.
9,623,159 B2 4/2017 Locke
D789,522 S 6/2017 Burgess et al.
9,687,849 B2 6/2017 Bruno et al.
9,694,949 B2 7/2017 Hendricks et al.
9,709,048 B2 7/2017 Kinjo
9,713,547 B2 7/2017 Lee et al.
9,732,754 B2 8/2017 Huang et al.
9,737,433 B2 8/2017 Joh
9,752,564 B2 9/2017 Arceno et al.
9,788,992 B2 10/2017 Harvie
D804,907 S 12/2017 Sandoval
D806,236 S 12/2017 Lin
9,868,564 B2 1/2018 Mcgirr et al.
D814,239 S 4/2018 Arora
D817,484 S 5/2018 Lafond
9,968,908 B2 5/2018 Ladrech et al.
10,010,393 B1 7/2018 Nguyen et al.
10,037,640 B2 7/2018 Gordon
10,058,470 B2 8/2018 Phillips
10,098,990 B2 10/2018 Koch et al.
D835,264 S 12/2018 Mozzicato et al.
D835,779 S 12/2018 Mozzicato et al.
D840,533 S 2/2019 Mozzicato et al.
D840,534 S 2/2019 Mozzicato et al.
10,225,376 B2 3/2019 Perez Martinez
10,226,376 B2 3/2019 Sanchez et al.
10,258,517 B1 4/2019 Maschino et al.
D848,612 S 5/2019 Mozzicato et al.
10,307,305 B1 6/2019 Hodges
10,335,121 B2 7/2019 Desai
D856,512 S 8/2019 Cowart et al.
10,376,406 B2 8/2019 Newton
10,376,407 B2 8/2019 Newton
10,390,989 B2 8/2019 Sanchez et al.
D858,144 S 9/2019 Fu
10,406,039 B2 9/2019 Villarreal
10,407,222 B2 9/2019 Allen
10,478,356 B2 11/2019 Griffin
10,500,108 B1 12/2019 Maschino et al.
10,502,198 B2 12/2019 Stumpf et al.
10,538,366 B2 1/2020 Pentelovitch et al.
10,569,938 B2 2/2020 Zhao et al.
10,577,156 B2 3/2020 Dagnelie et al.
RE47,930 E 4/2020 Cho
10,618,721 B2 4/2020 Vazin
D884,390 S 5/2020 Wang
10,669,079 B2 6/2020 Freedman et al.
D892,315 S 8/2020 Airy
10,730,672 B2 8/2020 Bertram et al.

(56) References Cited

U.S. PATENT DOCUMENTS 10,737,848 B2 8/2020 Philip et al.
10,765,854 B2 9/2020 Law et al.
10,766,670 B2 9/2020 Kittmann
10,799,386 B1 10/2020 Harrison
10,806,623 B2 10/2020 VanMiddendorp et al.
10,806,642 B2 10/2020 Tagomori et al.
D901,214 S 11/2020 Hu
10,849,799 B2 12/2020 Nishikawa et al.
10,857,025 B2 12/2020 Davis et al.
10,865,017 B1 12/2020 Cowart et al.
10,889,412 B2 1/2021 West et al.
10,913,581 B2 2/2021 Stahlecker
D912,244 S 3/2021 Rehm et al.
10,952,889 B2 3/2021 Newton et al.
10,973,378 B2 4/2021 Ryu et al.
10,973,678 B2 4/2021 Newton et al.
10,974,874 B2 4/2021 Ragias et al.
11,000,401 B2 5/2021 Ecklund et al.
11,002,165 B2 5/2021 Poulin
D923,365 S 6/2021 Wang
11,020,567 B2 6/2021 Rule et al.
11,026,829 B2 6/2021 Harvie
11,027,900 B2 6/2021 Liu
11,045,346 B2 6/2021 Argent et al.
D928,946 S 8/2021 Sanchez et al.
11,090,183 B2 8/2021 Sanchez et al.
11,160,695 B2 11/2021 Febo et al.
11,160,697 B2 11/2021 Maschino et al.
11,168,420 B2 11/2021 Kinugasa et al.
11,179,506 B2 11/2021 Barr et al.
11,199,116 B2 12/2021 Ostromecki et al.
11,207,206 B2 12/2021 Sharma et al.
D941,998 S 1/2022 Tretheway et al.
11,226,376 B2 1/2022 Yamauchi et al.
11,253,389 B2 2/2022 Sharma et al.
11,253,407 B2 2/2022 Miao et al.
11,326,586 B2 5/2022 Milner et al.
11,369,508 B2 6/2022 Ecklund et al.
11,369,524 B2 6/2022 Hubbard et al.
11,376,152 B2 7/2022 Sanchez et al.
11,382,786 B2 7/2022 Sanchez et al.
11,382,788 B2 7/2022 Hjorth et al.
11,389,318 B2 7/2022 Radl et al.
11,395,871 B2 7/2022 Radl et al.
11,399,990 B2 8/2022 Suyama
11,426,303 B2 8/2022 Davis et al.
11,504,265 B2 11/2022 Godinez et al.
11,529,252 B2 12/2022 Glithero et al.
11,547,788 B2 1/2023 Radl et al.
11,806,266 B2 11/2023 Sanchez et al.
11,813,189 B2 11/2023 Hussey et al.
11,839,567 B2 12/2023 Davis et al.
D1,010,109 S 1/2024 Ecklund et al.
11,857,716 B2 1/2024 Lee et al.
11,865,030 B2 1/2024 Davis et al.
11,890,221 B2 2/2024 Ulreich et al.
11,911,160 B2 2/2024 Woodard et al.
11,925,575 B2 3/2024 Newton
11,938,053 B2 3/2024 Austermann et al.
11,944,740 B2 4/2024 Hughett et al.
11,994,122 B2 5/2024 Bodain
11,998,475 B2 6/2024 Becker et al.
12,023,457 B2 7/2024 Mann et al.
12,042,422 B2 7/2024 Davis et al.
D1,038,385 S 8/2024 Ecklund et al.
12,064,372 B2 8/2024 Godinez et al.
12,070,432 B2 8/2024 Tourchak et al.
12,090,083 B2 9/2024 Ecklund et al.
12,121,468 B2 10/2024 Sanchez et al.
12,133,813 B2 11/2024 Ulreich et al.
12,138,195 B2 11/2024 Alder et al.
D1,054,019 S 12/2024 Miyawaki
D1,059,585 S 1/2025 Miyawaki
D1,059,586 S 1/2025 Miyawaki
12,186,229 B2 1/2025 Davis et al.
12,193,962 B2 1/2025 Newton et al.
D1,067,424 S 3/2025 Naughton et al.
12,245,966 B2 3/2025 Newton
12,274,638 B2 4/2025 Spector
D1,074,995 S 5/2025 Laffay et al.
12,324,765 B2 6/2025 Sanchez et al.
12,350,190 B2 7/2025 Hughett, Sr. et al.
D1,104,255 S 12/2025 Hanna et al.
D1,107,222 S 12/2025 Ecklund et al.
2001/0037097 A1 11/2001 Cheng et al.
2001/0037098 A1 11/2001 Snyder
2001/0054426 A1 12/2001 Knudson et al.
2002/0019614 A1 2/2002 Woon
2002/0026161 A1 2/2002 Grundke
2002/0026163 A1 2/2002 Grundke
2002/0033200 A1 3/2002 Alex et al.
2002/0042945 A1 4/2002 Sands
2002/0087131 A1 7/2002 Wolff et al.
2002/0091364 A1 7/2002 Prabhakar
2002/0189992 A1 12/2002 Schmidt et al.
2002/0193760 A1 12/2002 Thompson
2002/0193762 A1 12/2002 Suydam
2003/0004436 A1 1/2003 Schmidt et al.
2003/0018309 A1 1/2003 Breznock
2003/0032931 A1 2/2003 Grundke et al.
2003/0032944 A1 2/2003 Cawood
2003/0073964 A1 4/2003 Palumbo et al.
2003/0074724 A1 4/2003 Sands
2003/0120178 A1 6/2003 Heki
2003/0129178 A1 7/2003 Wegman et al.
2003/0157859 A1 8/2003 Ishikawa
2003/0181880 A1 9/2003 Schwartz
2003/0195484 A1 10/2003 Harvie
2003/0204173 A1 10/2003 Burns et al.
2003/0233079 A1 12/2003 Parks et al.
2004/0002687 A1 1/2004 Burns et al.
2004/0006321 A1 1/2004 Cheng et al.
2004/0015141 A1 1/2004 Cheng et al.
2004/0056122 A1 3/2004 Male et al.
2004/0084465 A1 5/2004 Luburic
2004/0098794 A1 5/2004 Ernest et al.
2004/0102753 A1 5/2004 Butler
2004/0127872 A1 7/2004 Petryk et al.
2004/0128749 A1 7/2004 Scott
2004/0143229 A1 7/2004 Easter
2004/0147863 A1 7/2004 Diaz et al.
2004/0147894 A1 7/2004 Mizutani et al.
2004/0147895 A1 7/2004 Mizutani et al.
2004/0158221 A1 8/2004 Mizutani et al.
2004/0176731 A1 9/2004 Cheng et al.
2004/0176746 A1 9/2004 Forral
2004/0181201 A1 9/2004 Mizutani et al.
2004/0187200 A1 9/2004 Otto et al.
2004/0191919 A1 9/2004 Unger et al.
2004/0194792 A1 10/2004 Zhuang et al.
2004/0200936 A1 10/2004 Opperthauser
2004/0207530 A1 10/2004 Nielsen
2004/0236292 A1 11/2004 Tazoe et al.
2004/0243075 A1 12/2004 Harvie
2004/0254547 A1 12/2004 Okabe et al.
2005/0010182 A1 1/2005 Parks et al.
2005/0010197 A1 1/2005 Lau et al.
2005/0033248 A1 2/2005 Machida et al.
2005/0065471 A1 3/2005 Kuntz
2005/0070861 A1 3/2005 Okabe et al.
2005/0070862 A1 3/2005 Tazoe et al.
2005/0082300 A1 4/2005 Modrell et al.
2005/0097662 A1 5/2005 Leimkuhler et al.
2005/0101924 A1 5/2005 Elson et al.
2005/0119630 A1 6/2005 Harvie
2005/0131361 A1 6/2005 Miskie
2005/0137557 A1 6/2005 Swiecicki et al.
2005/0137560 A1 6/2005 Mizutani et al.
2005/0137561 A1 6/2005 Mizutani et al.
2005/0148984 A1 7/2005 Lindsay et al.
2005/0154360 A1 7/2005 Harvie
2005/0177070 A1 8/2005 Levinson et al.
2005/0197645 A1 9/2005 Karpowicz et al.
2005/0215969 A1 9/2005 Mizutani et al.

(56) References Cited

U.S. PATENT DOCUMENTS

2005/0273069 A1 12/2005 Mizutani et al.
2005/0273920 A1 12/2005 Marinas
2005/0277903 A1 12/2005 Mizutani et al.
2005/0277904 A1 12/2005 Chase et al.
2005/0279359 A1 12/2005 LeBlanc et al.
2006/0004332 A1 1/2006 Marx
2006/0005307 A1 1/2006 Arguelles
2006/0015080 A1 1/2006 Mahnensmith
2006/0015081 A1 1/2006 Suzuki et al.
2006/0016778 A1 1/2006 Park
2006/0069359 A1 3/2006 Dipalma et al.
2006/0079852 A1 4/2006 Bubb et al.
2006/0079854 A1 4/2006 Kay et al.
2006/0100596 A1 5/2006 Miskie
2006/0111648 A1 5/2006 Vermaak
2006/0113334 A1 6/2006 Mikhail et al.
2006/0155214 A1 7/2006 Wightman
2006/0166350 A1 7/2006 Lowe et al.
2006/0171997 A1 8/2006 Gruenbacher et al.
2006/0180566 A1 8/2006 Mataya
2006/0200102 A1 9/2006 Cooper
2006/0229575 A1 10/2006 Boiarski
2006/0229576 A1 10/2006 Conway et al.
2006/0231648 A1 10/2006 Male et al.
2006/0235266 A1 10/2006 Nan
2006/0235359 A1 10/2006 Marland
2006/0241553 A1 10/2006 Harvie
2006/0269439 A1 11/2006 White
2006/0277670 A1 12/2006 Baker et al.
2007/0006368 A1 1/2007 Key et al.
2007/0010797 A1 1/2007 Nishtala et al.
2007/0016152 A1 1/2007 Karpowicz et al.
2007/0025886 A1 2/2007 Yong
2007/0038194 A1 2/2007 Wada et al.
2007/0055209 A1 3/2007 Patel et al.
2007/0073252 A1 3/2007 Forgrave
2007/0117880 A1 5/2007 Elson et al.
2007/0118993 A1 5/2007 Bates
2007/0135786 A1 6/2007 Schmidt et al.
2007/0137718 A1 6/2007 Rushlander et al.
2007/0149935 A1 6/2007 Dirico
2007/0191804 A1 8/2007 Coley
2007/0203464 A1 8/2007 Green et al.
2007/0214553 A1 9/2007 Carromba et al.
2007/0225663 A1 9/2007 Watt et al.
2007/0225666 A1 9/2007 Otto
2007/0225668 A1 9/2007 Otto
2007/0266486 A1 11/2007 Ramirez
2007/0270716 A1 11/2007 Wu et al.
2007/0282309 A1 12/2007 Bengtson et al.
2008/0004576 A1* 1/2008 Tanaka .................... A61F 5/451
604/326
2008/0015526 A1 1/2008 Reiner et al.
2008/0015527 A1 1/2008 House
2008/0033386 A1 2/2008 Okabe et al.
2008/0041869 A1 2/2008 Backaert
2008/0077099 A1 3/2008 House
2008/0091153 A1 4/2008 Harvie
2008/0091158 A1 4/2008 Yang
2008/0114327 A1 5/2008 Barge
2008/0140033 A1 6/2008 Burgess et al.
2008/0167634 A1 7/2008 Kouta et al.
2008/0183157 A1 7/2008 Walters
2008/0200884 A1 8/2008 Perkins et al.
2008/0215031 A1 9/2008 Belfort et al.
2008/0234642 A1 9/2008 Patterson et al.
2008/0269703 A1 10/2008 Collins et al.
2008/0281282 A1 11/2008 Finger et al.
2008/0287894 A1 11/2008 Van Den Heuvel et al.
2008/0312550 A1 12/2008 Nishtala et al.
2009/0025717 A1 1/2009 Pinel
2009/0048570 A1 2/2009 Jensen
2009/0056003 A1 3/2009 Ivie et al.
2009/0069761 A1 3/2009 Vogel
2009/0069765 A1 3/2009 Wortham
2009/0120179 A1 5/2009 Nylander et al.
2009/0192482 A1 7/2009 Dodge et al.
2009/0199857 A1 8/2009 Peake et al.
2009/0226541 A1 9/2009 Scholz et al.
2009/0234312 A1 9/2009 Otoole et al.
2009/0247968 A1 10/2009 Brooks et al.
2009/0251510 A1 10/2009 Noro et al.
2009/0254040 A1 10/2009 Bierman et al.
2009/0259206 A1 10/2009 Kai et al.
2009/0264840 A1 10/2009 Virginio
2009/0270822 A1 10/2009 Medeiros
2009/0281510 A1 11/2009 Fisher
2009/0283982 A1 11/2009 Thomas
2009/0306610 A1 12/2009 Van Den Heuvel et al.
2010/0004612 A1 1/2010 Thevenin
2010/0030189 A1 2/2010 Fleming
2010/0031429 A1 2/2010 Kim et al.
2010/0032789 A1 2/2010 Schoen et al.
2010/0058660 A1 3/2010 Williams
2010/0121289 A1 5/2010 Parks et al.
2010/0160882 A1 6/2010 Lowe
2010/0174250 A1 7/2010 Hu et al.
2010/0179493 A1 7/2010 Heagle et al.
2010/0185168 A1 7/2010 Graauw et al.
2010/0198172 A1 8/2010 Wada et al.
2010/0211032 A1 8/2010 Tsai et al.
2010/0234820 A1 9/2010 Tsai et al.
2010/0241104 A1 9/2010 Gilbert
2010/0263113 A1 10/2010 Shelton et al.
2010/0310845 A1 12/2010 Bond et al.
2011/0028920 A1 2/2011 Johannison
2011/0028922 A1 2/2011 Kay et al.
2011/0034889 A1 2/2011 Smith
2011/0036837 A1 2/2011 Shang
2011/0040267 A1 2/2011 Wada et al.
2011/0040271 A1 2/2011 Rogers et al.
2011/0054426 A1 3/2011 Stewart et al.
2011/0060299 A1 3/2011 Wada et al.
2011/0060300 A1 3/2011 Weig et al.
2011/0077495 A1 3/2011 Gilbert
2011/0077606 A1 3/2011 Wilcox et al.
2011/0087337 A1 4/2011 Forsell
2011/0145993 A1 6/2011 Rader et al.
2011/0152802 A1 6/2011 Dicamillo et al.
2011/0152842 A1 6/2011 Graffam et al.
2011/0164147 A1 7/2011 Takahashi et al.
2011/0172620 A1 7/2011 Khambatta
2011/0172625 A1 7/2011 Wada et al.
2011/0198904 A1 8/2011 Thomas et al.
2011/0202024 A1 8/2011 Cozzens
2011/0238023 A1 9/2011 Slayton
2011/0240648 A1 10/2011 Tucker
2011/0251572 A1 10/2011 Nishtala et al.
2011/0265889 A1 11/2011 Tanaka et al.
2011/0276020 A1 11/2011 Mitsui
2012/0004079 A1 1/2012 Hyacinth
2012/0029452 A1 2/2012 Roedsten
2012/0035577 A1 2/2012 Tomes et al.
2012/0041400 A1 2/2012 Christensen
2012/0059328 A1 3/2012 Dikeman et al.
2012/0066825 A1 3/2012 Birbara et al.
2012/0103347 A1 5/2012 Wheaton et al.
2012/0116336 A1 5/2012 Sharma et al.
2012/0137420 A1 6/2012 Gordon et al.
2012/0165768 A1 6/2012 Sekiyama et al.
2012/0209216 A1 8/2012 Jensen et al.
2012/0209225 A1 8/2012 Hu et al.
2012/0210503 A1 8/2012 Anzivino et al.
2012/0215187 A1 8/2012 Tippet et al.
2012/0233761 A1 9/2012 Huang
2012/0245541 A1 9/2012 Suzuki et al.
2012/0245542 A1 9/2012 Suzuki et al.
2012/0245547 A1 9/2012 Wilcox et al.
2012/0253303 A1 10/2012 Suzuki et al.
2012/0271259 A1 10/2012 Ulert
2012/0296305 A1 11/2012 Barraza Khaled et al.
2012/0316522 A1 12/2012 Carter et al.
2012/0330256 A1 12/2012 Wilcox et al.
2013/0006206 A1 1/2013 Wada et al.

(56) References Cited

U.S. PATENT DOCUMENTS

| | | | |
|---|---|---|---|
| 2013/0019374 | A1 | 1/2013 | Schwartz |
| 2013/0036544 | A1 | 2/2013 | Lee et al. |
| 2013/0045651 | A1 | 2/2013 | Esteves et al. |
| 2013/0046258 | A1 | 2/2013 | Chambers |
| 2013/0053804 | A1 | 2/2013 | Soerensen et al. |
| 2013/0096523 | A1 | 4/2013 | Chang et al. |
| 2013/0110059 | A1 | 5/2013 | Kossow et al. |
| 2013/0138064 | A1 | 5/2013 | Stroebech et al. |
| 2013/0144240 | A1 | 6/2013 | Ellis |
| 2013/0150813 | A1 | 6/2013 | Gordon et al. |
| 2013/0158494 | A1 | 6/2013 | Ong et al. |
| 2013/0165880 | A1 | 6/2013 | Amos et al. |
| 2013/0211385 | A1 | 8/2013 | Lazarus |
| 2013/0218112 | A1 | 8/2013 | Thompson |
| 2013/0245496 | A1 | 9/2013 | Wells et al. |
| 2013/0245586 | A1 | 9/2013 | Jha |
| 2013/0274711 | A1 | 10/2013 | O'Day |
| 2013/0292537 | A1 | 11/2013 | Dirico |
| 2013/0324954 | A1 | 12/2013 | Friedrich |
| 2013/0330501 | A1 | 12/2013 | Aizenberg et al. |
| 2014/0005647 | A1 | 1/2014 | Shuffler et al. |
| 2014/0031774 | A1 | 1/2014 | Bengtson |
| 2014/0039432 | A1 | 2/2014 | Dunbar et al. |
| 2014/0039440 | A1 | 2/2014 | Doescher |
| 2014/0058347 | A1 | 2/2014 | Marquette |
| 2014/0107599 | A1 | 4/2014 | Fink et al. |
| 2014/0157499 | A1 | 6/2014 | Suzuki et al. |
| 2014/0171889 | A1 | 6/2014 | Hopman et al. |
| 2014/0182051 | A1 | 7/2014 | Tanimoto et al. |
| 2014/0196189 | A1 | 7/2014 | Lee et al. |
| 2014/0230831 | A1 | 8/2014 | Zaltsberg et al. |
| 2014/0257231 | A1 | 9/2014 | Wang et al. |
| 2014/0303582 | A1 | 10/2014 | Wright et al. |
| 2014/0316381 | A1 | 10/2014 | Reglin |
| 2014/0325746 | A1 | 11/2014 | Block |
| 2014/0348139 | A1 | 11/2014 | Gomez Martinez |
| 2014/0352050 | A1 | 12/2014 | Yao et al. |
| 2014/0371628 | A1 | 12/2014 | Desai |
| 2015/0045757 | A1 | 2/2015 | Lee et al. |
| 2015/0047114 | A1 | 2/2015 | Ramirez |
| 2015/0048089 | A1 | 2/2015 | Robertson |
| 2015/0135423 | A1 | 5/2015 | Sharpe et al. |
| 2015/0157300 | A1 | 6/2015 | Ealovega et al. |
| 2015/0209188 | A1 | 7/2015 | Scheremet et al. |
| 2015/0209194 | A1 | 7/2015 | Heyman |
| 2015/0267862 | A1 | 9/2015 | Mishler |
| 2015/0290421 | A1 | 10/2015 | Glickman et al. |
| 2015/0290425 | A1 | 10/2015 | Macy et al. |
| 2015/0320583 | A1 | 11/2015 | Harvie |
| 2015/0329255 | A1 | 11/2015 | Rzepecki |
| 2015/0342799 | A1 | 12/2015 | Michiels et al. |
| 2015/0359660 | A1 | 12/2015 | Harvie |
| 2015/0359996 | A1 | 12/2015 | Arora et al. |
| 2015/0366699 | A1 | 12/2015 | Nelson |
| 2015/0374535 | A1 | 12/2015 | Davis et al. |
| 2016/0008193 | A1 | 1/2016 | Schulke |
| 2016/0029998 | A1 | 2/2016 | Brister et al. |
| 2016/0030228 | A1 | 2/2016 | Jones |
| 2016/0038356 | A1 | 2/2016 | Yao et al. |
| 2016/0051395 | A1 | 2/2016 | Ugarte |
| 2016/0058322 | A1 | 3/2016 | Brister et al. |
| 2016/0060001 | A1 | 3/2016 | Wada et al. |
| 2016/0100976 | A1 | 4/2016 | Conway et al. |
| 2016/0106604 | A1 | 4/2016 | Timm |
| 2016/0113809 | A1 | 4/2016 | Kim |
| 2016/0135792 | A1 | 5/2016 | Cai |
| 2016/0136338 | A1 | 5/2016 | Lee et al. |
| 2016/0183689 | A1 | 6/2016 | Miner |
| 2016/0256022 | A1 | 9/2016 | Le |
| 2016/0270982 | A1 | 9/2016 | Raycheck et al. |
| 2016/0278662 | A1 | 9/2016 | Brister et al. |
| 2016/0327553 | A1 | 11/2016 | Edwards et al. |
| 2016/0357400 | A1 | 12/2016 | Penha et al. |
| 2016/0366699 | A1 | 12/2016 | Zhang et al. |
| 2016/0367226 | A1 | 12/2016 | Newton et al. |
| 2016/0367411 | A1 | 12/2016 | Justiz et al. |
| 2016/0374848 | A1 | 12/2016 | Sanchez et al. |
| 2017/0007438 | A1 | 1/2017 | Harvie |
| 2017/0014560 | A1 | 1/2017 | Minskoff et al. |
| 2017/0042724 | A1 | 2/2017 | Ugarte |
| 2017/0042748 | A1 | 2/2017 | Griffin |
| 2017/0049605 | A1 | 2/2017 | Wisniewski |
| 2017/0100276 | A1 | 4/2017 | Joh |
| 2017/0107312 | A1 | 4/2017 | Hinayama et al. |
| 2017/0128638 | A1 | 5/2017 | Giezendanner et al. |
| 2017/0136209 | A1 | 5/2017 | Burnett et al. |
| 2017/0143534 | A1 | 5/2017 | Sanchez |
| 2017/0165100 | A1 | 6/2017 | Jackson et al. |
| 2017/0165405 | A1 | 6/2017 | Muser et al. |
| 2017/0189225 | A1 | 7/2017 | Voorhees et al. |
| 2017/0202692 | A1 | 7/2017 | Laniado |
| 2017/0216081 | A1 | 8/2017 | Accosta |
| 2017/0238911 | A1 | 8/2017 | Duval |
| 2017/0246026 | A1 | 8/2017 | Laniado |
| 2017/0252014 | A1 | 9/2017 | Siller Gonzalez et al. |
| 2017/0252202 | A9 | 9/2017 | Sanchez et al. |
| 2017/0266031 | A1 | 9/2017 | Sanchez et al. |
| 2017/0266658 | A1 | 9/2017 | Bruno et al. |
| 2017/0281399 | A1 | 10/2017 | Vanmiddendorp et al. |
| 2017/0281419 | A1 | 10/2017 | Pintado |
| 2017/0312116 | A1 | 11/2017 | Laniado |
| 2017/0325788 | A1 | 11/2017 | Ealovega et al. |
| 2017/0333244 | A1 | 11/2017 | Laniado |
| 2017/0340489 | A1 | 11/2017 | Yamada |
| 2017/0348139 | A1 | 12/2017 | Newton et al. |
| 2017/0354532 | A1 | 12/2017 | Holt |
| 2017/0354551 | A1 | 12/2017 | Gawley et al. |
| 2017/0367873 | A1 | 12/2017 | Grannum |
| 2018/0002075 | A1 | 1/2018 | Lee |
| 2018/0008451 | A1 | 1/2018 | Stroebech |
| 2018/0008804 | A1 | 1/2018 | Laniado |
| 2018/0021218 | A1 | 1/2018 | Brosch et al. |
| 2018/0028349 | A1 | 2/2018 | Newton et al. |
| 2018/0037384 | A1 | 2/2018 | Archeny et al. |
| 2018/0049910 | A1 | 2/2018 | Newton |
| 2018/0064572 | A1 | 3/2018 | Wiltshire |
| 2018/0104131 | A1 | 4/2018 | Killian |
| 2018/0127187 | A1 | 5/2018 | Sewell |
| 2018/0149635 | A1 | 5/2018 | Abir |
| 2018/0169281 | A1 | 6/2018 | Russell et al. |
| 2018/0193215 | A1 | 7/2018 | Davies et al. |
| 2018/0200101 | A1 | 7/2018 | Su |
| 2018/0214297 | A1 | 8/2018 | Hughett et al. |
| 2018/0221216 | A1 | 8/2018 | Benz et al. |
| 2018/0228642 | A1 | 8/2018 | Davis et al. |
| 2018/0229014 | A1 | 8/2018 | Guirguis et al. |
| 2018/0256384 | A1 | 9/2018 | Kasirye |
| 2018/0271694 | A1 | 9/2018 | Fernandez et al. |
| 2018/0280236 | A1 | 10/2018 | Ludin et al. |
| 2018/0317892 | A1 | 11/2018 | Catlin |
| 2018/0325748 | A1 | 11/2018 | Sharma et al. |
| 2019/0001029 | A1 | 1/2019 | Davie et al. |
| 2019/0001030 | A1 | 1/2019 | Braga et al. |
| 2019/0021899 | A1 | 1/2019 | Met |
| 2019/0029869 | A1 | 1/2019 | Huchthausen |
| 2019/0038451 | A1 | 2/2019 | Harvie |
| 2019/0046102 | A1 | 2/2019 | Kushnir et al. |
| 2019/0059938 | A1 | 2/2019 | Holsten |
| 2019/0060138 | A1 | 2/2019 | Marquez et al. |
| 2019/0091059 | A1 | 3/2019 | Gabriel |
| 2019/0100362 | A1 | 4/2019 | Meyers et al. |
| 2019/0133126 | A1 | 5/2019 | Modak et al. |
| 2019/0133814 | A1 | 5/2019 | Tammen et al. |
| 2019/0142624 | A1 | 5/2019 | Sanchez et al. |
| 2019/0224036 | A1 | 7/2019 | Sanchez et al. |
| 2019/0226189 | A1 | 7/2019 | Braxton |
| 2019/0240079 | A1 | 8/2019 | Tuli |
| 2019/0247222 | A1 | 8/2019 | Ecklund et al. |
| 2019/0247223 | A1 | 8/2019 | Brun et al. |
| 2019/0247623 | A1 | 8/2019 | Helm et al. |
| 2019/0282391 | A1 | 9/2019 | Johannes et al. |
| 2019/0314189 | A1 | 10/2019 | Acosta |
| 2019/0314190 | A1 | 10/2019 | Sanchez et al. |
| 2019/0321587 | A1 | 10/2019 | Mcmenamin et al. |

(56) References Cited

U.S. PATENT DOCUMENTS

| | | | |
|---|---|---|---|
| 2019/0344934 | A1 | 11/2019 | Faerber et al. |
| 2019/0365303 | A1 | 12/2019 | Bullington et al. |
| 2019/0365307 | A1 | 12/2019 | Laing et al. |
| 2019/0365561 | A1 | 12/2019 | Newton et al. |
| 2019/0374373 | A1 | 12/2019 | Joh |
| 2020/0008985 | A1 | 1/2020 | Nguyen et al. |
| 2020/0016012 | A1 | 1/2020 | Dutkiewicz |
| 2020/0030595 | A1 | 1/2020 | Boukidjian et al. |
| 2020/0040561 | A1 | 2/2020 | Sugawara |
| 2020/0046544 | A1 | 2/2020 | Godinez et al. |
| 2020/0055638 | A1 | 2/2020 | Lau et al. |
| 2020/0070392 | A1 | 3/2020 | Huber et al. |
| 2020/0085609 | A1 | 3/2020 | Schelch et al. |
| 2020/0085610 | A1 | 3/2020 | Cohn et al. |
| 2020/0086090 | A1 | 3/2020 | Von Weymarn-schärli et al. |
| 2020/0107518 | A1 | 4/2020 | Hiroshima et al. |
| 2020/0129322 | A1 | 4/2020 | Leuckel |
| 2020/0171217 | A9 | 6/2020 | Braga et al. |
| 2020/0179177 | A1 | 6/2020 | Erdem et al. |
| 2020/0187918 | A1 | 6/2020 | Wiygul |
| 2020/0206015 | A1 | 7/2020 | Langer |
| 2020/0206039 | A1 | 7/2020 | Mclain |
| 2020/0214910 | A1 | 7/2020 | Varona et al. |
| 2020/0216898 | A1 | 7/2020 | Hubbell |
| 2020/0216989 | A1 | 7/2020 | Kinugasa et al. |
| 2020/0229964 | A1 | 7/2020 | Staali et al. |
| 2020/0231343 | A1 | 7/2020 | Freedman et al. |
| 2020/0232841 | A1 | 7/2020 | Satish et al. |
| 2020/0246172 | A1 | 8/2020 | Ho |
| 2020/0246203 | A1 | 8/2020 | Tulk et al. |
| 2020/0255189 | A1 | 8/2020 | Liu |
| 2020/0261280 | A1 | 8/2020 | Heyman |
| 2020/0276046 | A1 | 9/2020 | Staali et al. |
| 2020/0306075 | A1 | 10/2020 | Newton et al. |
| 2020/0315837 | A1 | 10/2020 | Radl et al. |
| 2020/0315838 | A1 | 10/2020 | Eckert |
| 2020/0315872 | A1 | 10/2020 | Viens et al. |
| 2020/0315874 | A1 | 10/2020 | Viens et al. |
| 2020/0331672 | A1 | 10/2020 | Bertram et al. |
| 2020/0345332 | A1 | 11/2020 | Duval |
| 2020/0352774 | A1 | 11/2020 | Rabinowitz et al. |
| 2020/0353135 | A1 | 11/2020 | Gregory et al. |
| 2020/0367677 | A1 | 11/2020 | Silsby et al. |
| 2020/0369444 | A1 | 11/2020 | Silsby et al. |
| 2020/0375781 | A1 | 12/2020 | Staali et al. |
| 2020/0375810 | A1 | 12/2020 | Carlin et al. |
| 2020/0384242 | A1 | 12/2020 | Havard et al. |
| 2020/0385179 | A1 | 12/2020 | Mccourt |
| 2020/0390591 | A1 | 12/2020 | Glithero et al. |
| 2020/0390592 | A1 | 12/2020 | Merrill |
| 2020/0398024 | A1 | 12/2020 | Fletter et al. |
| 2020/0405521 | A1 | 12/2020 | Glasroe |
| 2020/0405523 | A1 | 12/2020 | Obst et al. |
| 2021/0007910 | A1 | 1/2021 | Furukawa |
| 2021/0008771 | A1 | 1/2021 | Huber et al. |
| 2021/0009323 | A1 | 1/2021 | Markarian et al. |
| 2021/0020072 | A1 | 1/2021 | Moehring et al. |
| 2021/0023279 | A1 | 1/2021 | Radl et al. |
| 2021/0059853 | A1 | 3/2021 | Davis et al. |
| 2021/0061523 | A1 | 3/2021 | Bytheway |
| 2021/0069005 | A1 | 3/2021 | Sanchez et al. |
| 2021/0069008 | A1 | 3/2021 | Blabas et al. |
| 2021/0069009 | A1 | 3/2021 | Im |
| 2021/0069030 | A1 | 3/2021 | Nishikawa et al. |
| 2021/0077993 | A1 | 3/2021 | Nazareth et al. |
| 2021/0113749 | A1 | 4/2021 | Radl et al. |
| 2021/0121318 | A1 | 4/2021 | Pinlac |
| 2021/0137724 | A1 | 5/2021 | Ecklund et al. |
| 2021/0138190 | A1 | 5/2021 | Erbey et al. |
| 2021/0154055 | A1 | 5/2021 | Villarreal |
| 2021/0170079 | A1 | 6/2021 | Radl et al. |
| 2021/0178390 | A1 | 6/2021 | Oueslati et al. |
| 2021/0186742 | A1 | 6/2021 | Newton et al. |
| 2021/0186744 | A1 | 6/2021 | Spector |
| 2021/0206144 | A1 | 7/2021 | Ewell |
| 2021/0211568 | A1 | 7/2021 | Zhou et al. |
| 2021/0212865 | A1 | 7/2021 | Wallajapet et al. |
| 2021/0220162 | A1 | 7/2021 | Jamison |
| 2021/0220163 | A1 | 7/2021 | Mayrand |
| 2021/0228400 | A1 | 7/2021 | Glithero |
| 2021/0228401 | A1 | 7/2021 | Becker et al. |
| 2021/0228795 | A1 | 7/2021 | Hughett et al. |
| 2021/0229877 | A1 | 7/2021 | Ragias et al. |
| 2021/0236323 | A1 | 8/2021 | Austermann et al. |
| 2021/0236324 | A1 | 8/2021 | Sweeney |
| 2021/0251814 | A1 | 8/2021 | Jönegren et al. |
| 2021/0267787 | A1 | 9/2021 | Nazemi |
| 2021/0275343 | A1 | 9/2021 | Sanchez et al. |
| 2021/0275344 | A1 | 9/2021 | Wing |
| 2021/0290454 | A1 | 9/2021 | Yamada |
| 2021/0290464 | A1 | 9/2021 | Furuta |
| 2021/0315726 | A1 | 10/2021 | Lin |
| 2021/0315727 | A1 | 10/2021 | Jiang |
| 2021/0353449 | A1 | 11/2021 | Sharma et al. |
| 2021/0353450 | A1 | 11/2021 | Sharma et al. |
| 2021/0361469 | A1 | 11/2021 | Liu et al. |
| 2021/0369495 | A1 | 12/2021 | Cheng et al. |
| 2021/0386925 | A1 | 12/2021 | Hartwell et al. |
| 2021/0393433 | A1 | 12/2021 | Godinez et al. |
| 2022/0015958 | A1 | 1/2022 | Ito |
| 2022/0023091 | A1 | 1/2022 | Ecklund et al. |
| 2022/0026546 | A1 | 1/2022 | Aono et al. |
| 2022/0031290 | A1 | 2/2022 | Weed |
| 2022/0031523 | A1 | 2/2022 | Pierpoint |
| 2022/0039995 | A1 | 2/2022 | Johannes et al. |
| 2022/0047410 | A1 | 2/2022 | Walthall |
| 2022/0062025 | A1 | 3/2022 | Shields et al. |
| 2022/0062027 | A1 | 3/2022 | Mitchell et al. |
| 2022/0062028 | A1 | 3/2022 | Mitchell et al. |
| 2022/0062029 | A1 | 3/2022 | Johannes et al. |
| 2022/0066825 | A1 | 3/2022 | Saraf et al. |
| 2022/0071811 | A1 | 3/2022 | Cheng et al. |
| 2022/0071826 | A1 | 3/2022 | Kulkarni et al. |
| 2022/0104965 | A1 | 4/2022 | Vaninetti et al. |
| 2022/0104976 | A1 | 4/2022 | Hoeger et al. |
| 2022/0104981 | A1 | 4/2022 | Jones |
| 2022/0117773 | A1 | 4/2022 | Davis et al. |
| 2022/0117774 | A1 | 4/2022 | Meyer et al. |
| 2022/0117775 | A1 | 4/2022 | Jones et al. |
| 2022/0118165 | A1 | 4/2022 | Knapp et al. |
| 2022/0133524 | A1 | 5/2022 | Davis |
| 2022/0151817 | A1 | 5/2022 | Mann |
| 2022/0160949 | A1 | 5/2022 | Simiele et al. |
| 2022/0168159 | A1 | 6/2022 | Triado et al. |
| 2022/0193312 | A1 | 6/2022 | Lee et al. |
| 2022/0211536 | A1 | 7/2022 | Johannes et al. |
| 2022/0218510 | A1 | 7/2022 | Metzger et al. |
| 2022/0229053 | A1 | 7/2022 | Levin et al. |
| 2022/0241106 | A1 | 8/2022 | Johannes et al. |
| 2022/0248836 | A1 | 8/2022 | Cagle et al. |
| 2022/0257407 | A1 | 8/2022 | Johannes et al. |
| 2022/0265460 | A1 | 8/2022 | Coker |
| 2022/0265462 | A1 | 8/2022 | Alder et al. |
| 2022/0270711 | A1 | 8/2022 | Feala et al. |
| 2022/0273482 | A1 | 9/2022 | Johannes et al. |
| 2022/0280357 | A1 | 9/2022 | Jagannathan et al. |
| 2022/0280710 | A1 | 9/2022 | Agrawal et al. |
| 2022/0287689 | A1 | 9/2022 | Johannes |
| 2022/0287691 | A1 | 9/2022 | Wormser et al. |
| 2022/0287867 | A1 | 9/2022 | Jones et al. |
| 2022/0287868 | A1 | 9/2022 | Garvey et al. |
| 2022/0296408 | A1 | 9/2022 | Evans et al. |
| 2022/0305191 | A1 | 9/2022 | Joseph et al. |
| 2022/0313222 | A1 | 10/2022 | Austermann et al. |
| 2022/0313474 | A1 | 10/2022 | Kriscovich et al. |
| 2022/0331170 | A1 | 10/2022 | Erdem et al. |
| 2022/0339023 | A1 | 10/2022 | Davis et al. |
| 2022/0339024 | A1 | 10/2022 | Johannes et al. |
| 2022/0354685 | A1 | 11/2022 | Davis et al. |
| 2022/0362049 | A1 | 11/2022 | Austermann et al. |
| 2022/0370231 | A1 | 11/2022 | Wang et al. |
| 2022/0370234 | A1 | 11/2022 | Hughett et al. |
| 2022/0370235 | A1 | 11/2022 | Johannes et al. |
| 2022/0370237 | A1 | 11/2022 | Parmar et al. |

(56) References Cited

U.S. PATENT DOCUMENTS

| | | | |
|---|---|---|---|
| 2022/0387001 | A1 | 12/2022 | Askenazi et al. |
| 2022/0387693 | A1 | 12/2022 | Bannwart et al. |
| 2022/0395390 | A1 | 12/2022 | Brooks |
| 2022/0395391 | A1 | 12/2022 | Saunders et al. |
| 2022/0401252 | A1 | 12/2022 | Warren |
| 2022/0409419 | A1 | 12/2022 | Garvey et al. |
| 2022/0409422 | A1 | 12/2022 | Schneider et al. |
| 2023/0018845 | A1 | 1/2023 | Lee |
| 2023/0020563 | A1 | 1/2023 | Sharma et al. |
| 2023/0031640 | A1 | 2/2023 | Hughett et al. |
| 2023/0037159 | A1 | 2/2023 | Brennan et al. |
| 2023/0049924 | A1 | 2/2023 | Johannes et al. |
| 2023/0052238 | A1 | 2/2023 | Oluwasogo |
| 2023/0062994 | A1 | 3/2023 | Ecklund et al. |
| 2023/0070347 | A1 | 3/2023 | Watson et al. |
| 2023/0073708 | A1 | 3/2023 | Xu et al. |
| 2023/0089032 | A1 | 3/2023 | Hughett et al. |
| 2023/0091118 | A1 | 3/2023 | Watson |
| 2023/0099821 | A1 | 3/2023 | Radl et al. |
| 2023/0099991 | A1 | 3/2023 | Bianchi et al. |
| 2023/0105001 | A1 | 4/2023 | Whittome et al. |
| 2023/0110577 | A1 | 4/2023 | Choi |
| 2023/0138269 | A1 | 5/2023 | Abdelal et al. |
| 2023/0145365 | A1 | 5/2023 | Martin et al. |
| 2023/0155253 | A1 | 5/2023 | Yin et al. |
| 2023/0190511 | A1 | 6/2023 | Sharma et al. |
| 2023/0210504 | A1 | 7/2023 | Kuroda et al. |
| 2023/0210685 | A1 | 7/2023 | Fallows et al. |
| 2023/0218426 | A1 | 7/2023 | Hughett |
| 2023/0240884 | A1 | 8/2023 | Davis et al. |
| 2023/0248562 | A1 | 8/2023 | Sanchez et al. |
| 2023/0248564 | A1 | 8/2023 | Mann et al. |
| 2023/0255812 | A1 | 8/2023 | Sanchez et al. |
| 2023/0255813 | A1 | 8/2023 | Sanchez et al. |
| 2023/0255815 | A1 | 8/2023 | Newton |
| 2023/0263650 | A1 | 8/2023 | Sanchez et al. |
| 2023/0263655 | A1 | 8/2023 | Johannes et al. |
| 2023/0277360 | A1 | 9/2023 | Lambert et al. |
| 2023/0277362 | A1 | 9/2023 | Davis et al. |
| 2023/0285178 | A1 | 9/2023 | Sanchez et al. |
| 2023/0293339 | A1 | 9/2023 | James |
| 2023/0301846 | A1 | 9/2023 | Greenwood |
| 2023/0355423 | A1 | 11/2023 | Stevenson et al. |
| 2023/0389900 | A1 | 12/2023 | Xie et al. |
| 2023/0404791 | A1 | 12/2023 | Ecklund et al. |
| 2024/0008444 | A1 | 1/2024 | Su et al. |
| 2024/0009023 | A1 | 1/2024 | Johannes et al. |
| 2024/0024170 | A1 | 1/2024 | Scott |
| 2024/0033148 | A1 | 2/2024 | Gordon et al. |
| 2024/0041638 | A1 | 2/2024 | Johannes et al. |
| 2024/0058157 | A1 | 2/2024 | Davis |
| 2024/0058160 | A1 | 2/2024 | Young Joyner et al. |
| 2024/0058161 | A1 | 2/2024 | Ulreich et al. |
| 2024/0058520 | A1 | 2/2024 | Yin et al. |
| 2024/0065881 | A1 | 2/2024 | Kuroda et al. |
| 2024/0082044 | A1 | 3/2024 | Nguyen et al. |
| 2024/0099874 | A1 | 3/2024 | Sanchez et al. |
| 2024/0108268 | A1 | 4/2024 | Woodard et al. |
| 2024/0110318 | A1 | 4/2024 | Bendt et al. |
| 2024/0122773 | A1 | 4/2024 | Nguyen et al. |
| 2024/0123134 | A1 | 4/2024 | Kharkar et al. |
| 2024/0130885 | A1 | 4/2024 | Young Joyner et al. |
| 2024/0148539 | A1 | 5/2024 | Austermann et al. |
| 2024/0156633 | A1 | 5/2024 | Fallows et al. |
| 2024/0164935 | A1 | 5/2024 | Newton |
| 2024/0252343 | A1 | 8/2024 | Voda |
| 2024/0261131 | A1 | 8/2024 | Garvey et al. |
| 2024/0268986 | A1 | 8/2024 | Barnes et al. |
| 2024/0268989 | A1 | 8/2024 | Martin et al. |
| 2024/0268991 | A1 | 8/2024 | Davis |
| 2024/0269027 | A1 | 8/2024 | Tourchak et al. |
| 2024/0285425 | A1 | 8/2024 | Donohoe et al. |
| 2024/0325190 | A1 | 10/2024 | Minchew et al. |
| 2024/0341998 | A1 | 10/2024 | Julian et al. |
| 2024/0358539 | A1 | 10/2024 | Gallup |
| 2024/0358542 | A1 | 10/2024 | Richardson et al. |
| 2024/0374414 | A1 | 11/2024 | Richardson et al. |
| 2025/0009552 | A1 | 1/2025 | Blabas et al. |
| 2025/0073055 | A1 | 3/2025 | Ecklund et al. |
| 2025/0107920 | A1 | 4/2025 | Fallows et al. |
| 2025/0107921 | A1 | 4/2025 | Sanchez et al. |
| 2025/0367358 | A1 | 12/2025 | Smith et al. |

FOREIGN PATENT DOCUMENTS

| | | | |
|---|---|---|---|
| AU | 2022349367 | A1 | 4/2024 |
| CA | 2165286 | C | 9/1999 |
| CA | 2335223 | A1 | 1/2000 |
| CA | 2354132 | A1 | 6/2000 |
| CA | 2359091 | C | 9/2003 |
| CA | 2488867 | C | 8/2007 |
| CA | 3031934 | A1 | 2/2018 |
| CA | 3050918 | A1 | 8/2018 |
| CA | 3098571 | A1 | 11/2019 |
| CA | 3144181 | A1 | 1/2021 |
| CA | 3188651 | A1 | 7/2023 |
| CN | 2269203 | Y | 12/1997 |
| CN | 1332620 | A | 1/2002 |
| CN | 1434693 | A | 8/2003 |
| CN | 1533755 | A | 10/2004 |
| CN | 1579348 | A | 2/2005 |
| CN | 1602825 | A | 4/2005 |
| CN | 1638708 | A | 7/2005 |
| CN | 1720888 | A | 1/2006 |
| CN | 2936204 | Y | 8/2007 |
| CN | 101262836 | A | 9/2008 |
| CN | 101522148 | A | 9/2009 |
| CN | 102159159 | A | 8/2011 |
| CN | 202184840 | U | 4/2012 |
| CN | 102481441 | A | 5/2012 |
| CN | 202463712 | U | 10/2012 |
| CN | 202950810 | U | 5/2013 |
| CN | 103533968 | A | 1/2014 |
| CN | 103717180 | A | 4/2014 |
| CN | 204562697 | U | 8/2015 |
| CN | 105411783 | A | 3/2016 |
| CN | 105451607 | A | 3/2016 |
| CN | 105451693 | A | 3/2016 |
| CN | 105534632 | A | 5/2016 |
| CN | 106132360 | A | 11/2016 |
| CN | 106137631 | A | 11/2016 |
| CN | 205849719 | U | 1/2017 |
| CN | 205924282 | U | 2/2017 |
| CN | 106726089 | A | 5/2017 |
| CN | 107847384 | A | 3/2018 |
| CN | 107920912 | A | 4/2018 |
| CN | 108420590 | A | 8/2018 |
| CN | 207785556 | U | 8/2018 |
| CN | 209285902 | U | 8/2019 |
| CN | 110381883 | A | 10/2019 |
| CN | 111465375 | A | 7/2020 |
| CN | 211198839 | U | 8/2020 |
| CN | 111991136 | A | 11/2020 |
| CN | 112022488 | A | 12/2020 |
| CN | 212234893 | U | 12/2020 |
| CN | 212466312 | U | 2/2021 |
| CN | 112566550 | A | 3/2021 |
| CN | 112603184 | A | 4/2021 |
| CN | 213490035 | U | 6/2021 |
| CN | 114007493 | A | 2/2022 |
| CN | 114375187 | A | 4/2022 |
| CN | 116096332 | A | 5/2023 |
| DE | 1516466 | A1 | 6/1969 |
| DE | 2721330 | A1 | 11/1977 |
| DE | 2742298 | A1 | 3/1978 |
| DE | 9407554.9 | U1 | 5/1995 |
| DE | 4443710 | A1 | 6/1995 |
| DE | 4416094 | A1 | 11/1995 |
| DE | 4236097 | C2 | 10/1996 |
| DE | 19619597 | A1 | 11/1997 |
| DE | 202005013173 | U1 | 6/2006 |
| DE | 102005037762 | B3 | 9/2006 |
| DE | 102011103783 | A1 | 12/2012 |
| DE | 102012112818 | A1 | 6/2014 |

(56) References Cited

FOREIGN PATENT DOCUMENTS

| | | | |
|---|---|---|---|
| DE | 202015104597 | U1 | 7/2016 |
| DE | 102018118570 | A1 | 2/2020 |
| DE | 102020121462 | B3 | 1/2022 |
| DK | 9600118 | | 11/1996 |
| EP | 0032138 | A2 | 7/1981 |
| EP | 0066070 | B1 | 12/1982 |
| EP | 0068712 | A1 | 1/1983 |
| EP | 0140470 | A1 | 5/1985 |
| EP | 0220962 | A1 | 5/1987 |
| EP | 0140471 | B1 | 5/1988 |
| EP | 0274753 | A2 | 7/1988 |
| EP | 0119143 | B1 | 11/1988 |
| EP | 0483592 | A1 | 5/1992 |
| EP | 0483730 | A1 | 5/1992 |
| EP | 0610638 | A1 | 8/1994 |
| EP | 0613355 | A1 | 9/1994 |
| EP | 0711536 | A1 | 5/1996 |
| EP | 0613355 | B1 | 1/1997 |
| EP | 0680296 | B1 | 5/1997 |
| EP | 0787472 | A1 | 8/1997 |
| EP | 0966936 | A1 | 12/1999 |
| EP | 0987293 | A1 | 3/2000 |
| EP | 1063953 | A1 | 1/2001 |
| EP | 0653928 | B1 | 10/2002 |
| EP | 1332738 | A1 | 8/2003 |
| EP | 1382318 | A1 | 1/2004 |
| EP | 1089684 | B1 | 10/2004 |
| EP | 1616542 | A1 | 1/2006 |
| EP | 1382318 | B1 | 5/2006 |
| EP | 1063953 | B1 | 1/2007 |
| EP | 1658831 | B1 | 1/2008 |
| EP | 1872752 | A1 | 1/2008 |
| EP | 2180907 | A1 | 5/2010 |
| EP | 2380532 | A1 | 10/2011 |
| EP | 2389908 | A1 | 11/2011 |
| EP | 2601916 | A1 | 6/2013 |
| EP | 2676643 | A1 | 12/2013 |
| EP | 2470251 | B1 | 12/2014 |
| EP | 2997950 | A2 | 3/2016 |
| EP | 2879534 | B1 | 3/2017 |
| EP | 3424471 | A1 | 1/2019 |
| EP | 3169292 | B1 | 11/2019 |
| EP | 3753492 | A1 | 12/2020 |
| EP | 3777801 | A1 | 2/2021 |
| EP | 3788992 | A1 | 3/2021 |
| EP | 3576689 | B1 | 3/2022 |
| EP | 3752110 | B1 | 3/2022 |
| EP | 3787570 | B1 | 3/2022 |
| EP | 4025163 | A1 | 7/2022 |
| EP | 3463180 | B1 | 3/2023 |
| EP | 3749230 | B1 | 3/2023 |
| EP | 3569205 | B1 | 6/2023 |
| EP | 4192402 | A1 | 6/2023 |
| EP | 4218702 | A1 | 8/2023 |
| EP | 3624742 | B1 | 1/2024 |
| EP | 4382082 | A2 | 6/2024 |
| EP | 4445881 | A2 | 10/2024 |
| EP | 4464288 | A2 | 11/2024 |
| EP | 4215134 | B1 | 1/2025 |
| EP | 4494611 | A2 | 1/2025 |
| EP | 4527361 | A2 | 3/2025 |
| FR | 2826704 | A1 | 1/2003 |
| GB | 871820 | A | 7/1961 |
| GB | 0873045 | A | 7/1961 |
| GB | 996370 | A | 6/1965 |
| GB | 1011517 | A | 12/1965 |
| GB | 1467144 | A | 3/1977 |
| GB | 2106395 | A | 4/1983 |
| GB | 2106784 | A | 4/1983 |
| GB | 2148126 | A | 5/1985 |
| GB | 2171315 | A | 8/1986 |
| GB | 2181953 | A | 5/1987 |
| GB | 2148126 | B | 7/1987 |
| GB | 2191095 | A | 12/1987 |
| GB | 2199750 | A | 7/1988 |
| GB | 2260907 | A | 5/1993 |
| GB | 2415386 | A | 12/2005 |
| GB | 2462267 | A | 2/2010 |
| GB | 2469496 | A | 10/2010 |
| GB | 2490327 | A | 10/2012 |
| GB | 2507318 | A | 4/2014 |
| GB | 2612752 | A | 5/2023 |
| IT | 201800009129 | A1 | 4/2020 |
| JP | S498638 | U | 1/1974 |
| JP | S5410596 | A | 1/1979 |
| JP | S5410596 | Y2 | 5/1979 |
| JP | S54155729 | U | 10/1979 |
| JP | S55155618 | A | 12/1980 |
| JP | S56152629 | U | 11/1981 |
| JP | S57142534 | U | 9/1982 |
| JP | S5888596 | U | 6/1983 |
| JP | S58130026 | A | 8/1983 |
| JP | S58188016 | U | 12/1983 |
| JP | S59118161 | A | 7/1984 |
| JP | S61502100 | A | 9/1986 |
| JP | S63107780 | U | 7/1988 |
| JP | H0267530 | A | 3/1990 |
| JP | H02103871 | A | 4/1990 |
| JP | H02131422 | A | 5/1990 |
| JP | H02131422 | U | 11/1990 |
| JP | H0460220 | A | 2/1992 |
| JP | H0515928 | U | 3/1993 |
| JP | H05123349 | A | 5/1993 |
| JP | H05123350 | A | 5/1993 |
| JP | H0625981 | U | 4/1994 |
| JP | H0626264 | U | 4/1994 |
| JP | 3087938 | B2 | 10/1995 |
| JP | H085630 | A | 1/1996 |
| JP | H08117271 | A | 5/1996 |
| JP | H08510924 | A | 11/1996 |
| JP | 2686634 | B2 | 12/1997 |
| JP | H1038669 | A | 2/1998 |
| JP | H1040141 | A | 2/1998 |
| JP | H10225430 | A | 8/1998 |
| JP | H11113946 | A | 4/1999 |
| JP | H11290365 | A | 10/1999 |
| JP | 2000116690 | A | 4/2000 |
| JP | 2000152953 | A | 6/2000 |
| JP | 2000185068 | A | 7/2000 |
| JP | 2000225139 | A | 8/2000 |
| JP | 2001054531 | A | 2/2001 |
| JP | 2001070331 | A | 3/2001 |
| JP | 2001224616 | A | 8/2001 |
| JP | 2001276107 | A | 10/2001 |
| JP | 2001276108 | A | 10/2001 |
| JP | 2002028173 | A | 1/2002 |
| JP | 2002502667 | A | 1/2002 |
| JP | 2002102285 | A | 4/2002 |
| JP | 2003038563 | A | 2/2003 |
| JP | 2003505152 | A | 2/2003 |
| JP | 2003126242 | A | 5/2003 |
| JP | 2003180722 | A | 7/2003 |
| JP | 2003227004 | A | 8/2003 |
| JP | 2003528691 | A | 9/2003 |
| JP | 2004057578 | A | 2/2004 |
| JP | 2004130056 | A | 4/2004 |
| JP | 2004267400 | A | 9/2004 |
| JP | 2004267530 | A | 9/2004 |
| JP | 2005052219 | A | 3/2005 |
| JP | 2005066011 | A | 3/2005 |
| JP | 2005066325 | A | 3/2005 |
| JP | 2005102978 | A | 4/2005 |
| JP | 2005518237 | A | 6/2005 |
| JP | 2005518901 | A | 6/2005 |
| JP | 3749097 | B2 | 12/2005 |
| JP | 2006026108 | A | 2/2006 |
| JP | 3123547 | B2 | 6/2006 |
| JP | 2006136491 | A | 6/2006 |
| JP | 2006136492 | A | 6/2006 |
| JP | 2006204868 | A | 8/2006 |
| JP | 2007044494 | A | 2/2007 |
| JP | 3132659 | B2 | 5/2007 |
| JP | 2007209687 | A | 8/2007 |
| JP | 2007259898 | A | 10/2007 |

(56) References Cited

FOREIGN PATENT DOCUMENTS

| | | | |
|---|---|---|---|
| JP | 4039641 | B2 | 11/2007 |
| JP | 2008005975 | A | 1/2008 |
| JP | 2008278928 | A | 11/2008 |
| JP | 2009500111 | A | 1/2009 |
| JP | 2009509570 | A | 3/2009 |
| JP | 2009165887 | A | 7/2009 |
| JP | 2009525776 | A | 7/2009 |
| JP | 2010504150 | A | 2/2010 |
| JP | 2010058795 | A | 3/2010 |
| JP | 2010081981 | A | 4/2010 |
| JP | 2010166954 | A | 8/2010 |
| JP | 4640772 | B2 | 12/2010 |
| JP | 2010536439 | A | 12/2010 |
| JP | 2011500225 | A | 1/2011 |
| JP | 2011030962 | A | 2/2011 |
| JP | 4747166 | B2 | 5/2011 |
| JP | 2011087823 | A | 5/2011 |
| JP | 4801218 | B1 | 8/2011 |
| JP | 2011522584 | A | 8/2011 |
| JP | 2011202664 | A | 10/2011 |
| JP | 2011218130 | A | 11/2011 |
| JP | 2011224070 | A | 11/2011 |
| JP | 3175719 | U | 4/2012 |
| JP | 2012522014 | A | 9/2012 |
| JP | 2012523869 | A | 10/2012 |
| JP | 2013238608 | A | 11/2013 |
| JP | 2014521960 | A | 8/2014 |
| JP | 2015092945 | A | 5/2015 |
| JP | 2015513678 | A | 5/2015 |
| JP | 3198994 | B2 | 7/2015 |
| JP | 2015221390 | A | 12/2015 |
| JP | 2016521191 | A | 7/2016 |
| JP | 2017014698 | A | 1/2017 |
| JP | 3208707 | U | 2/2017 |
| JP | 3209321 | U | 3/2017 |
| JP | 2017070400 | A | 4/2017 |
| JP | 2017512603 | A | 5/2017 |
| JP | 2017127596 | A | 7/2017 |
| JP | 2017201272 | A | 11/2017 |
| JP | 2019010375 | A | 1/2019 |
| JP | 2019076342 | A | 5/2019 |
| JP | 2019525811 | A | 9/2019 |
| JP | 2019170942 | A | 10/2019 |
| JP | 2019533492 | A | 11/2019 |
| JP | 2020510464 | A | 4/2020 |
| JP | 2020520775 | A | 7/2020 |
| JP | 2020124425 | A | 8/2020 |
| JP | 2021007472 | A | 1/2021 |
| JP | 2021041145 | A | 3/2021 |
| JP | 2021074491 | A | 5/2021 |
| JP | 2021120686 | A | 8/2021 |
| JP | 2021520952 | A | 8/2021 |
| JP | 2021522009 | A | 8/2021 |
| JP | 2021522013 | A | 8/2021 |
| JP | 2021522019 | A | 8/2021 |
| JP | 7129493 | B2 | 8/2022 |
| JP | 2022554252 | A | 12/2022 |
| JP | 2023532132 | A | 7/2023 |
| KR | 200290061 | Y1 | 9/2002 |
| KR | 20030047451 | A | 6/2003 |
| KR | 20080005516 | A | 1/2008 |
| KR | 20090072069 | A | 7/2009 |
| KR | 20090104426 | A | 10/2009 |
| KR | 20090110359 | A | 10/2009 |
| KR | 101035745 | B1 | 5/2011 |
| KR | 20120005922 | A | 1/2012 |
| KR | 20140039485 | A | 4/2014 |
| KR | 101432639 | B1 | 8/2014 |
| KR | 20180022173 | A | 3/2018 |
| KR | 20180106659 | A | 10/2018 |
| KR | 20180108774 | A | 10/2018 |
| KR | 20230034343 | A | 3/2023 |
| PT | 2068717 | E | 6/2013 |
| SE | 505542 | C2 | 9/1997 |
| TW | 408207 | B | 10/2000 |
| TW | 202123903 | A | 7/2021 |
| WO | 8101957 | A1 | 7/1981 |
| WO | 8804558 | A1 | 6/1988 |
| WO | 9104714 | A2 | 4/1991 |
| WO | 9104714 | A3 | 6/1991 |
| WO | 9220299 | A3 | 2/1993 |
| WO | 9303690 | A1 | 3/1993 |
| WO | 9307839 | A1 | 4/1993 |
| WO | 9309736 | A2 | 5/1993 |
| WO | 9309736 | A3 | 6/1993 |
| WO | 9416914 | A1 | 8/1994 |
| WO | 9514448 | A2 | 6/1995 |
| WO | 9600096 | A1 | 1/1996 |
| WO | 9634636 | A1 | 11/1996 |
| WO | 9817211 | A1 | 4/1998 |
| WO | 9830336 | A1 | 7/1998 |
| WO | 0000112 | A1 | 1/2000 |
| WO | 0000113 | A1 | 1/2000 |
| WO | 0025651 | A1 | 5/2000 |
| WO | 0033773 | A1 | 6/2000 |
| WO | 0057784 | A1 | 10/2000 |
| WO | 0069377 | A1 | 11/2000 |
| WO | 0079497 | A1 | 12/2000 |
| WO | 0145618 | A1 | 6/2001 |
| WO | 0145621 | A1 | 6/2001 |
| WO | 02094160 | A1 | 11/2002 |
| WO | 03013967 | A1 | 2/2003 |
| WO | 03015671 | A1 | 2/2003 |
| WO | 03024824 | A1 | 3/2003 |
| WO | 03055423 | A1 | 7/2003 |
| WO | 03071931 | A2 | 9/2003 |
| WO | 03079942 | A1 | 10/2003 |
| WO | 03071931 | A3 | 2/2004 |
| WO | 2004019836 | A1 | 3/2004 |
| WO | 2004024046 | A1 | 3/2004 |
| WO | 2004026195 | A1 | 4/2004 |
| WO | 2005003725 | A2 | 1/2005 |
| WO | 2005051252 | A1 | 6/2005 |
| WO | 2005060558 | A2 | 7/2005 |
| WO | 2005074571 | A3 | 9/2005 |
| WO | 2005089687 | A2 | 9/2005 |
| WO | 2005107661 | A2 | 11/2005 |
| WO | 2006021220 | A1 | 3/2006 |
| WO | 2006037140 | A2 | 4/2006 |
| WO | 2007005851 | A2 | 1/2007 |
| WO | 2007007845 | A1 | 1/2007 |
| WO | 2007042823 | A2 | 4/2007 |
| WO | 2007055651 | A1 | 5/2007 |
| WO | 2006098950 | A3 | 11/2007 |
| WO | 2007128156 | A3 | 2/2008 |
| WO | 2008026106 | A2 | 3/2008 |
| WO | 2008078117 | A1 | 7/2008 |
| WO | 2008104019 | A1 | 9/2008 |
| WO | 2008141471 | A1 | 11/2008 |
| WO | 2009004368 | A1 | 1/2009 |
| WO | 2009004369 | A1 | 1/2009 |
| WO | 2009052496 | A1 | 4/2009 |
| WO | 2009052502 | A1 | 4/2009 |
| WO | 2009007702 | A4 | 7/2009 |
| WO | 2009101738 | A1 | 8/2009 |
| WO | 2010058192 | A1 | 5/2010 |
| WO | 2010030122 | A3 | 7/2010 |
| WO | 2010101915 | A3 | 1/2011 |
| WO | 2011018132 | A1 | 2/2011 |
| WO | 2011018133 | A1 | 2/2011 |
| WO | 2011024864 | A1 | 3/2011 |
| WO | 2011054118 | A1 | 5/2011 |
| WO | 2011079132 | A1 | 6/2011 |
| WO | 2011107972 | A1 | 9/2011 |
| WO | 2011108972 | A1 | 9/2011 |
| WO | 2011117292 | A1 | 9/2011 |
| WO | 2011123219 | A1 | 10/2011 |
| WO | 2011132043 | A1 | 10/2011 |
| WO | 2012012908 | A1 | 2/2012 |
| WO | 2012020506 | A1 | 2/2012 |
| WO | 2012065274 | A1 | 5/2012 |
| WO | 2012097462 | A1 | 7/2012 |
| WO | 2012098796 | A1 | 7/2012 |
| WO | 2012101288 | A1 | 8/2012 |

(56) References Cited

FOREIGN PATENT DOCUMENTS

| | | | |
|---|---|---|---|
| WO | 2012175916 | A1 | 12/2012 |
| WO | 2013018435 | A1 | 2/2013 |
| WO | 2013033429 | A1 | 3/2013 |
| WO | 2013055434 | A1 | 4/2013 |
| WO | 2013082397 | A1 | 6/2013 |
| WO | 2013103291 | A2 | 7/2013 |
| WO | 2013131109 | A1 | 9/2013 |
| WO | 2013167478 | A1 | 11/2013 |
| WO | 2013177716 | A1 | 12/2013 |
| WO | 2014041534 | A1 | 3/2014 |
| WO | 2014046420 | A1 | 3/2014 |
| WO | 2014118518 | A1 | 8/2014 |
| WO | 2014160852 | A1 | 10/2014 |
| WO | 2015023599 | A1 | 2/2015 |
| WO | 2015052348 | A1 | 4/2015 |
| WO | 2015068384 | A1 | 5/2015 |
| WO | 2015169403 | A1 | 11/2015 |
| WO | 2015170307 | A1 | 11/2015 |
| WO | 2015197462 | A1 | 12/2015 |
| WO | 2016051385 | A1 | 4/2016 |
| WO | 2016055989 | A1 | 4/2016 |
| WO | 2016071894 | A1 | 5/2016 |
| WO | 2016103242 | A1 | 6/2016 |
| WO | 2016116915 | A1 | 7/2016 |
| WO | 2016124203 | A1 | 8/2016 |
| WO | 2016139448 | A1 | 9/2016 |
| WO | 2016166562 | A1 | 10/2016 |
| WO | 2016167535 | A1 | 10/2016 |
| WO | 2016191574 | A1 | 12/2016 |
| WO | 2016200088 | A1 | 12/2016 |
| WO | 2016200361 | A1 | 12/2016 |
| WO | 2016204731 | A1 | 12/2016 |
| WO | 2017001532 | A2 | 1/2017 |
| WO | 2017075226 | A1 | 5/2017 |
| WO | 2017100511 | A1 | 6/2017 |
| WO | 2017152198 | A1 | 9/2017 |
| WO | 2017153357 | A1 | 9/2017 |
| WO | 2017162559 | A1 | 9/2017 |
| WO | 2017205446 | A1 | 11/2017 |
| WO | 2017209779 | A1 | 12/2017 |
| WO | 2017210524 | A1 | 12/2017 |
| WO | 2018022414 | A1 | 2/2018 |
| WO | 2018044781 | A1 | 3/2018 |
| WO | 2018056953 | A1 | 3/2018 |
| WO | 2018090550 | A1 | 5/2018 |
| WO | 2018138513 | A1 | 8/2018 |
| WO | 2018144318 | A1 | 8/2018 |
| WO | 2018144463 | A1 | 8/2018 |
| WO | 2018150263 | A1 | 8/2018 |
| WO | 2018150268 | A1 | 8/2018 |
| WO | 2018152156 | A1 | 8/2018 |
| WO | 2018183791 | A1 | 10/2018 |
| WO | 2018150267 | A3 | 11/2018 |
| WO | 2018200721 | A1 | 11/2018 |
| WO | 2018235026 | A1 | 12/2018 |
| WO | 2018235065 | A1 | 12/2018 |
| WO | 2019004404 | A1 | 1/2019 |
| WO | 2019038732 | A1 | 2/2019 |
| WO | 2019041005 | A1 | 3/2019 |
| WO | 2019044217 | A1 | 3/2019 |
| WO | 2019044218 | A1 | 3/2019 |
| WO | 2019044219 | A1 | 3/2019 |
| WO | 2019050959 | A1 | 3/2019 |
| WO | 2019065541 | A1 | 4/2019 |
| WO | 2019096845 | A1 | 5/2019 |
| WO | 2019150385 | A1 | 8/2019 |
| WO | 2019161094 | A1 | 8/2019 |
| WO | 2019188566 | A1 | 10/2019 |
| WO | 2019190593 | A1 | 10/2019 |
| WO | 2019212949 | A1 | 11/2019 |
| WO | 2019212950 | A1 | 11/2019 |
| WO | 2019212951 | A1 | 11/2019 |
| WO | 2019212952 | A1 | 11/2019 |
| WO | 2019212954 | A1 | 11/2019 |
| WO | 2019212955 | A1 | 11/2019 |
| WO | 2019212956 | A1 | 11/2019 |
| WO | 2019214787 | A1 | 11/2019 |
| WO | 2019214788 | A1 | 11/2019 |
| WO | 2019226826 | A1 | 11/2019 |
| WO | 2019239433 | A1 | 12/2019 |
| WO | 2020000994 | A1 | 1/2020 |
| WO | 2020020618 | A1 | 1/2020 |
| WO | 2020033752 | A1 | 2/2020 |
| WO | 2020038822 | A1 | 2/2020 |
| WO | 2020088409 | A1 | 5/2020 |
| WO | 2020049394 | A3 | 6/2020 |
| WO | 2020120657 | A1 | 6/2020 |
| WO | 2020152575 | A1 | 7/2020 |
| WO | 2020182923 | A1 | 9/2020 |
| WO | 2020204967 | A1 | 10/2020 |
| WO | 2020205939 | A1 | 10/2020 |
| WO | 2020209898 | A1 | 10/2020 |
| WO | 2020242790 | A1 | 12/2020 |
| WO | 2020251893 | A1 | 12/2020 |
| WO | 2020256865 | A1 | 12/2020 |
| WO | 2021007144 | A1 | 1/2021 |
| WO | 2021007345 | A1 | 1/2021 |
| WO | 2021010844 | A1 | 1/2021 |
| WO | 2021016026 | A1 | 1/2021 |
| WO | 2021016056 | A1 | 1/2021 |
| WO | 2021016300 | A1 | 1/2021 |
| WO | 2021025919 | A1 | 2/2021 |
| WO | 2021034886 | A1 | 2/2021 |
| WO | 2021041123 | A1 | 3/2021 |
| WO | 2021046501 | A1 | 3/2021 |
| WO | 2021086868 | A1 | 5/2021 |
| WO | 2021094352 | A1 | 5/2021 |
| WO | 2021094639 | A1 | 5/2021 |
| WO | 2021097067 | A1 | 5/2021 |
| WO | 2021102296 | A1 | 5/2021 |
| WO | 2021107025 | A1 | 6/2021 |
| WO | 2021138411 | A1 | 7/2021 |
| WO | 2021138414 | A1 | 7/2021 |
| WO | 2021154686 | A1 | 8/2021 |
| WO | 2021155206 | A1 | 8/2021 |
| WO | 2021170075 | A1 | 9/2021 |
| WO | 2021173436 | A1 | 9/2021 |
| WO | 2021188817 | A1 | 9/2021 |
| WO | 2021195384 | A1 | 9/2021 |
| WO | 2021205995 | A1 | 10/2021 |
| WO | 2021207621 | A1 | 10/2021 |
| WO | 2021211568 | A1 | 10/2021 |
| WO | 2021211801 | A1 | 10/2021 |
| WO | 2021211914 | A1 | 10/2021 |
| WO | 2021216419 | A1 | 10/2021 |
| WO | 2021216422 | A1 | 10/2021 |
| WO | 2021231532 | A1 | 11/2021 |
| WO | 2021247523 | A1 | 12/2021 |
| WO | 2021257202 | A1 | 12/2021 |
| WO | 2022006256 | A1 | 1/2022 |
| WO | 2022029662 | A1 | 2/2022 |
| WO | 2022031943 | A1 | 2/2022 |
| WO | 2022035745 | A1 | 2/2022 |
| WO | 2022051220 | A1 | 3/2022 |
| WO | 2022051360 | A1 | 3/2022 |
| WO | 2022054613 | A1 | 3/2022 |
| WO | 2022066704 | A1 | 3/2022 |
| WO | 2022067392 | A1 | 4/2022 |
| WO | 2022069950 | A1 | 4/2022 |
| WO | 2022071429 | A1 | 4/2022 |
| WO | 2022076322 | A1 | 4/2022 |
| WO | 2022076427 | A2 | 4/2022 |
| WO | 2022086898 | A1 | 4/2022 |
| WO | 2022090199 | A1 | 5/2022 |
| WO | 2022098536 | A1 | 5/2022 |
| WO | 2022099087 | A1 | 5/2022 |
| WO | 2022101999 | A1 | 5/2022 |
| WO | 2022115692 | A1 | 6/2022 |
| WO | 2022125685 | A1 | 6/2022 |
| WO | 2022140545 | A1 | 6/2022 |
| WO | 2022145231 | A1 | 7/2022 |
| WO | 2022150290 | A1 | 7/2022 |
| WO | 2022150360 | A1 | 7/2022 |
| WO | 2022150463 | A1 | 7/2022 |

(56) References Cited

FOREIGN PATENT DOCUMENTS

| | | | |
|---|---|---|---|
| WO | 2022159392 | A1 | 7/2022 |
| WO | 2022170182 | A1 | 8/2022 |
| WO | 2022173803 | A1 | 8/2022 |
| WO | 2022182385 | A1 | 9/2022 |
| WO | 2022187152 | A1 | 9/2022 |
| WO | 2022192188 | A1 | 9/2022 |
| WO | 2022192347 | A1 | 9/2022 |
| WO | 2022204000 | A1 | 9/2022 |
| WO | 2022216507 | A1 | 10/2022 |
| WO | 2022216776 | A1 | 10/2022 |
| WO | 2022222030 | A1 | 10/2022 |
| WO | 2022251184 | A1 | 12/2022 |
| WO | 2022251425 | A1 | 12/2022 |
| WO | 2022271783 | A1 | 12/2022 |
| WO | 2023286058 | A1 | 1/2023 |
| WO | 2023014639 | A1 | 2/2023 |
| WO | 2023014641 | A1 | 2/2023 |
| WO | 2023018475 | A2 | 2/2023 |
| WO | 2023018656 | A1 | 2/2023 |
| WO | 2023018657 | A1 | 2/2023 |
| WO | 2023023777 | A1 | 3/2023 |
| WO | 2023034139 | A1 | 3/2023 |
| WO | 2023034453 | A1 | 3/2023 |
| WO | 2023038945 | A1 | 3/2023 |
| WO | 2023038950 | A1 | 3/2023 |
| WO | 2023049109 | A1 | 3/2023 |
| WO | 2023049156 | A1 | 3/2023 |
| WO | 2023049175 | A1 | 3/2023 |
| WO | 2023086394 | A1 | 5/2023 |
| WO | 2023146529 | A1 | 8/2023 |
| WO | 2023149884 | A1 | 8/2023 |
| WO | 2023149902 | A1 | 8/2023 |
| WO | 2023149903 | A1 | 8/2023 |
| WO | 2023154390 | A1 | 8/2023 |
| WO | 2023163725 | A1 | 8/2023 |
| WO | 2023191764 | A1 | 10/2023 |
| WO | 2023244238 | A1 | 12/2023 |
| WO | 2024043871 | A1 | 2/2024 |
| WO | 2024058788 | A1 | 3/2024 |
| WO | 2024253655 | A1 | 12/2024 |
| WO | 2025034959 | A1 | 2/2025 |
| WO | 2025038087 | A1 | 2/2025 |
| WO | 2025038088 | A1 | 2/2025 |
| WO | 2025048789 | A1 | 3/2025 |
| WO | 2025071622 | A1 | 4/2025 |
| WO | 2025179267 | A1 | 8/2025 |
| WO | 2026035497 | A1 | 2/2026 |

OTHER PUBLICATIONS

Advisory Action for U.S. Appl. No. 17/448,811 mailed Nov. 15, 2023.
Final Office Action for U.S. Appl. No. 16/904,868 mailed Nov. 2, 2023.
Final Office Action for U.S. Appl. No. 17/501,591 mailed Nov. 14, 2023.
Non-Final Office Action for U.S. Appl. No. 16/452,145 mailed Nov. 2, 2023.
Non-Final Office Action for U.S. Appl. No. 16/478,180 mailed Nov. 7, 2023.
Non-Final Office Action for U.S. Appl. No. 17/444,792 mailed Nov. 17, 2023.
Non-Final Office Action for U.S. Appl. No. 18/140,163 mailed Nov. 9, 2023.
Notice of Allowance for U.S. Appl. No. 16/369,676 mailed Nov. 14, 2023.
Notice of Allowance for U.S. Appl. No. 17/662,700 mailed Nov. 15, 2023.
Notice of Allowance for U.S. Appl. No. 18/299,788 mailed Nov. 6, 2023.
U.S. Appl. No. 17/451,719, filed Oct. 19, 2021.
U.S. Appl. No. 18/389,009, filed Nov. 13, 2023.
U.S. Appl. No. 18/562,626, filed Nov. 20, 2023.
U.S. Appl. No. 63/596,012, filed Nov. 3, 2023.
"Proximate Definition & Meaning" <https://www.merriam-webster.com/dictionary/> 2025.
"Surface Energy Data for Cellulose acetate, CAS # 9004-35-7", Diviersified Enterprises, 2009, 1 page.
"Tube Definition & Meaning" Merriam Webster Dictionary, 2025, <https://www.merriam-webster.com/dictionary/tube>.
Advisory Action for U.S. Appl. No. 16/452,258 mailed May 5, 2025.
Advisory Action for U.S. Appl. No. 17/378,015 mailed Oct. 28, 2025.
Advisory Action for U.S. Appl. No. 17/394,055 mailed Jan. 9, 2026.
Advisory Action for U.S. Appl. No. 17/446,256 mailed Nov. 6, 2025.
Advisory Action for U.S. Appl. No. 17/446,654 mailed Feb. 28, 2025.
Advisory Action for U.S. Appl. No. 17/451,345 mailed May 13, 2025.
Advisory Action for U.S. Appl. No. 17/595,747 mailed Mar. 17, 2025.
Advisory Action for U.S. Appl. No. 17/653,314 mailed Apr. 8, 2025.
Advisory Action for U.S. Appl. No. 17/655,464 mailed Feb. 25, 2025.
Advisory Action for U.S. Appl. No. 17/664,487 mailed Apr. 24, 2025.
Advisory Action for U.S. Appl. No. 17/757,311 mailed Jul. 2, 2025.
Advisory Action for U.S. Appl. No. 18/265,736 mailed Mar. 4, 2026.
Corrected Notice of Allowability for U.S. Appl. No. 17/444,792 mailed Jun. 24, 2025.
Corrected Notice of Allowability for U.S. Appl. No. 17/653,314 mailed Oct. 29, 2025.
Corrected Notice of Allowability for U.S. Appl. No. 17/754,736 mailed Feb. 12, 2026.
Corrected Notice of Allowability for U.S. Appl. No. 17/808,354 mailed Nov. 25, 2025.
Corrected Notice of Allowability for U.S. Appl. No. 17/996,253 mailed Apr. 28, 2025.
Corrected Notice of Allowability for U.S. Appl. No. 18/134,857 mailed Mar. 14, 2025.
Corrected Notice of Allowability for U.S. Appl. No. 18/260,122 mailed Aug. 11, 2025.
Corrected Notice of Allowability for U.S. Appl. No. 18/264,004 mailed Feb. 10, 2026.
Corrected Notice of Allowability for U.S. Appl. No. 18/264,004 mailed Feb. 3, 2026.
Di Mauro, et al., "Penile length and circumference dimensions: A large study in young Italian men" Reconstructive Urology, Men's Health Working Parties of the European Association of Urology (EAU) Young Academic Urologists (YAU). pp. 1-7, Mar. 8, 2021.
Final Office Action for U.S. Appl. No. 16/452,258 mailed Feb. 11, 2026.
Final Office Action for U.S. Appl. No. 17/051,600 mailed Aug. 6, 2025.
Final Office Action for U.S. Appl. No. 17/378,015 mailed Jun. 18, 2025.
Final Office Action for U.S. Appl. No. 17/394,055 mailed Sep. 24, 2025.
Final Office Action for U.S. Appl. No. 17/446,256 mailed Jun. 11, 2025.
Final Office Action for U.S. Appl. No. 17/446,654 mailed Dec. 22, 2025.
Final Office Action for U.S. Appl. No. 17/451,345 mailed Feb. 6, 2025.
Final Office Action for U.S. Appl. No. 17/595,747 mailed Feb. 19, 2026.
Final Office Action for U.S. Appl. No. 17/597,408 mailed Mar. 24, 2025.
Final Office Action for U.S. Appl. No. 17/614,173 mailed May 20, 2025.
Final Office Action for U.S. Appl. No. 17/625,941 mailed Feb. 18, 2025.

(56) References Cited

OTHER PUBLICATIONS

Final Office Action for U.S. Appl. No. 17/628,411 mailed Apr. 30, 2025.
Final Office Action for U.S. Appl. No. 17/631,619 mailed Oct. 1, 2025.
Final Office Action for U.S. Appl. No. 17/653,137 mailed Jun. 25, 2025.
Final Office Action for U.S. Appl. No. 17/653,314 mailed Jan. 30, 2025.
Final Office Action for U.S. Appl. No. 17/653,920 mailed Apr. 24, 2025.
Final Office Action for U.S. Appl. No. 17/655,464 mailed Feb. 17, 2026.
Final Office Action for U.S. Appl. No. 17/664,487 mailed Jan. 5, 2026.
Final Office Action for U.S. Appl. No. 17/756,201 mailed Dec. 30, 2025.
Final Office Action for U.S. Appl. No. 17/757,311 mailed Mar. 31, 2025.
Final Office Action for U.S. Appl. No. 17/759,697 mailed Jun. 4, 2025.
Final Office Action for U.S. Appl. No. 17/808,354 mailed Jun. 13, 2025.
Final Office Action for U.S. Appl. No. 17/809,083 mailed Jan. 23, 2026.
Final Office Action for U.S. Appl. No. 17/907,125 mailed Apr. 30, 2025.
Final Office Action for U.S. Appl. No. 17/929,887, filed Jan. 13, 2026.
Final Office Action for U.S. Appl. No. 17/933,590 mailed Feb. 19, 2026.
Final Office Action for U.S. Appl. No. 18/003,029 mailed Nov. 26, 2025.
Final Office Action for U.S. Appl. No. 18/006,807 mailed Dec. 23, 2025.
Final Office Action for U.S. Appl. No. 18/042,842 mailed Jan. 27, 2026.
Final Office Action for U.S. Appl. No. 18/043,618 mailed Nov. 26, 2025.
Final Office Action for U.S. Appl. No. 18/139,523 mailed May 8, 2025.
Final Office Action for U.S. Appl. No. 18/164,800 mailed Dec. 5, 2025.
Final Office Action for U.S. Appl. No. 18/247,986 mailed Jan. 7, 2026.
Final Office Action for U.S. Appl. No. 18/265,736 mailed Dec. 1, 2025.
Foamtech, "Foam Packaging Isnert: Best Selection Guide", https://web/archive.org/web/20170922162235/http://www.foamtechchina/com:80/foam-packaging-insert/, Sep. 22, 2017, 25 pages.
International Search Report and Written Opinion from International Application No. PCT/US2023/031432 mailed Feb. 29, 2024.
International Search Report and Written Opinion from International Application No. PCT/US2023/036875 mailed May 31, 2024.
International Search Report and Written Opinion from International Application No. PCT/US2023/077205 mailed Jul. 19, 2024.
International Search Report and Written Opinion from International Application No. PCT/US2024/053681 mailed Jan. 27, 2025.
International Search Report and Written Opinion from International Application No. PCT/US2024/058598 mailed Mar. 28, 2025.
International Search Report and Written Opinion from International Application No. PCT/US2025/018907 mailed May 16, 2025.
International Search Report and Written Opinion from International Application No. PCT/US2025/018909 mailed May 20, 2025.
International Search Report and Written Opinion from International Application No. PCT/US2025/018913 mailed Jun. 18, 2025.
Issue Notification for U.S. Appl. No. 16/433,773 mailed Jan. 21, 2026.
Issue Notification for U.S. Appl. No. 16/478,180 mailed Mar. 5, 2025.
Issue Notification for U.S. Appl. No. 16/904,868 mailed Apr. 30, 2025.
Issue Notification for U.S. Appl. No. 17/051,399 mailed Mar. 4, 2026.
Issue Notification for U.S. Appl. No. 17/051,585 mailed Mar. 26, 2025.
Issue Notification for U.S. Appl. No. 17/444,792 mailed Jun. 25, 2025.
Issue Notification for U.S. Appl. No. 17/451,354 mailed Feb. 25, 2026.
Issue Notification for U.S. Appl. No. 17/501,591 mailed Mar. 5, 2025.
Issue Notification for U.S. Appl. No. 17/529,769 mailed Feb. 19, 2025.
Issue Notification for U.S. Appl. No. 17/597,673 mailed Jun. 4, 2025.
Issue Notification for U.S. Appl. No. 17/625,941 mailed Feb. 25, 2026.
Issue Notification for U.S. Appl. No. 17/646,771 mailed Mar. 19, 2025.
Issue Notification for U.S. Appl. No. 17/653,137 mailed Feb. 4, 2025.
Issue Notification for U.S. Appl. No. 17/653,314 mailed Feb. 11, 2026.
Issue Notification for U.S. Appl. No. 17/653,920 mailed Oct. 22, 2025.
Issue Notification for U.S. Appl. No. 17/661,090 mailed Feb. 5, 2025.
Issue Notification for U.S. Appl. No. 17/663,330 mailed Feb. 26, 2025.
Issue Notification for U.S. Appl. No. 17/749,340 mailed May 28, 2025.
Issue Notification for U.S. Appl. No. 17/755,236 mailed Oct. 29, 2025.
Issue Notification for U.S. Appl. No. 17/758,316 mailed Jun. 25, 2025.
Issue Notification for U.S. Appl. No. 17/808,354 mailed Mar. 4, 2026.
Issue Notification for U.S. Appl. No. 17/878,268 mailed Feb. 4, 2026.
Issue Notification for U.S. Appl. No. 17/907,125 mailed Dec. 30, 2025.
Issue Notification for U.S. Appl. No. 17/912,147 mailed Mar. 18, 2026.
Issue Notification for U.S. Appl. No. 17/996,064 mailed Nov. 5, 2025.
Issue Notification for U.S. Appl. No. 17/996,155 mailed Oct. 8, 2025.
Issue Notification for U.S. Appl. No. 17/996,253 mailed Oct. 29, 2025.
Issue Notification for U.S. Appl. No. 17/996,468 mailed Nov. 26, 2025.
Issue Notification for U.S. Appl. No. 18/007,105 mailed Oct. 1, 2025.
Issue Notification for U.S. Appl. No. 18/044,413 mailed Dec. 30, 2025.
Issue Notification for U.S. Appl. No. 18/134,857 mailed May 28, 2025.
Issue Notification for U.S. Appl. No. 18/140,751 mailed Feb. 12, 2025.
Issue Notification for U.S. Appl. No. 18/260,122 mailed Nov. 12, 2025.
Issue Notification for U.S. Appl. No. 18/415,080 mailed Apr. 9, 2025.
Issue Notification for U.S. Appl. No. 18/426,795 mailed Feb. 19, 2025.
Issue Notification for U.S. Appl. No. 18/584,002 mailed Apr. 16, 2025.
Non-Final Office Action for U.S. Appl. No. 16/433,773 mailed Feb. 28, 2025.
Non-Final Office Action for U.S. Appl. No. 16/452,258 mailed Sep. 24, 2025.

(56) References Cited

OTHER PUBLICATIONS

Non-Final Office Action for U.S. Appl. No. 17/051,600 mailed Feb. 28, 2025.
Non-Final Office Action for U.S. Appl. No. 17/378,015 mailed Dec. 12, 2025.
Non-Final Office Action for U.S. Appl. No. 17/394,055 mailed Mar. 13, 2025.
Non-Final Office Action for U.S. Appl. No. 17/394,055 mailed Mar. 19, 2025.
Non-Final Office Action for U.S. Appl. No. 17/446,256 mailed Dec. 2, 2025.
Non-Final Office Action for U.S. Appl. No. 17/446,654 mailed May 1, 2025.
Non-Final Office Action for U.S. Appl. No. 17/451,354 mailed Mar. 19, 2025.
Non-Final Office Action for U.S. Appl. No. 17/595,747 mailed Jun. 12, 2025.
Non-Final Office Action for U.S. Appl. No. 17/614,173 mailed Dec. 29, 2025.
Non-Final Office Action for U.S. Appl. No. 17/628,411 mailed Dec. 22, 2025.
Non-Final Office Action for U.S. Appl. No. 17/631,619 mailed Mar. 19, 2025.
Non-Final Office Action for U.S. Appl. No. 17/635,866 mailed Jul. 29, 2025.
Non-Final Office Action for U.S. Appl. No. 17/645,821 mailed Mar. 31, 2025.
Non-Final Office Action for U.S. Appl. No. 17/653,137 mailed Jan. 28, 2025.
Non-Final Office Action for U.S. Appl. No. 17/653,314 mailed May 8, 2025.
Non-Final Office Action for U.S. Appl. No. 17/655,464 mailed Mar. 20, 2025.
Non-Final Office Action for U.S. Appl. No. 17/664,487 mailed May 19, 2025.
Non-Final Office Action for U.S. Appl. No. 17/754,736 mailed Mar. 31, 2025.
Non-Final Office Action for U.S. Appl. No. 17/756,201 mailed Apr. 24, 2025.
Non-Final Office Action for U.S. Appl. No. 17/757,311 mailed Sep. 2, 2025.
Non-Final Office Action for U.S. Appl. No. 17/758,152 mailed Apr. 8, 2025.
Non-Final Office Action for U.S. Appl. No. 17/759,587 mailed Jan. 26, 2026.
Non-Final Office Action for U.S. Appl. No. 17/759,697 mailed Sep. 17, 2025.
Non-Final Office Action for U.S. Appl. No. 17/809,083 mailed Apr. 2, 2025.
Non-Final Office Action for U.S. Appl. No. 17/809,083 mailed Mar. 7, 2025.
Non-Final Office Action for U.S. Appl. No. 17/878,268 mailed Mar. 17, 2025.
Non-Final Office Action for U.S. Appl. No. 17/912,147 mailed May 29, 2025.
Non-Final Office Action for U.S. Appl. No. 17/929,887 mailed Jun. 25, 2025.
Non-Final Office Action for U.S. Appl. No. 17/930,238 mailed Jun. 30, 2025.
Non-Final Office Action for U.S. Appl. No. 17/933,590 mailed Jul. 29, 2025.
Non-Final Office Action for U.S. Appl. No. 17/996,064 mailed Mar. 6, 2025.
Non-Final Office Action for U.S. Appl. No. 17/996,556 mailed Dec. 22, 2025.
Non-Final Office Action for U.S. Appl. No. 18/003,029 mailed Apr. 18, 2025.
Non-Final Office Action for U.S. Appl. No. 18/006,807 mailed May 29, 2025.
Non-Final Office Action for U.S. Appl. No. 18/034,902 mailed Mar. 20, 2026.
Non-Final Office Action for U.S. Appl. No. 18/042,842 mailed May 22, 2025.
Non-Final Office Action for U.S. Appl. No. 18/043,618 mailed May 19, 2025.
Non-Final Office Action for U.S. Appl. No. 18/043,807 mailed Feb. 10, 2026.
Non-Final Office Action for U.S. Appl. No. 18/115,444 mailed Oct. 22, 2025.
Non-Final Office Action for U.S. Appl. No. 18/139,523 mailed Nov. 19, 2025.
Non-Final Office Action for U.S. Appl. No. 18/150,360 mailed Nov. 5, 2025.
Non-Final Office Action for U.S. Appl. No. 18/164,800 mailed Apr. 25, 2025.
Non-Final Office Action for U.S. Appl. No. 18/246,121 mailed Jan. 22, 2026.
Non-Final Office Action for U.S. Appl. No. 18/247,986 mailed Jun. 4, 2025.
Non-Final Office Action for U.S. Appl. No. 18/249,577 mailed Nov. 17, 2025.
Non-Final Office Action for U.S. Appl. No. 18/254,638 mailed Nov. 17, 2025.
Non-Final Office Action for U.S. Appl. No. 18/259,626 mailed Jan. 30, 2026.
Non-Final Office Action for U.S. Appl. No. 18/259,626 mailed Jul. 11, 2025.
Non-Final Office Action for U.S. Appl. No. 18/260,394, filed Jan. 13, 2026.
Non-Final Office Action for U.S. Appl. No. 18/263,800 mailed Feb. 5, 2026.
Non-Final Office Action for U.S. Appl. No. 18/264,004 mailed May 15, 2025.
Non-Final Office Action for U.S. Appl. No. 18/264,278 mailed Nov. 10, 2025.
Non-Final Office Action for U.S. Appl. No. 18/265,736 mailed Jul. 1, 2025.
Non-Final Office Action for U.S. Appl. No. 18/376,274 mailed Mar. 9, 2026.
Non-Final Office Action for U.S. Appl. No. 18/548,152 mailed Sep. 16, 2025.
Non-Final Office Action for U.S. Appl. No. 18/549,387 mailed Mar. 4, 2026.
Non-Final Office Action for U.S. Appl. No. 18/551,492 mailed Mar. 19, 2026.
Non-Final Office Action for U.S. Appl. No. 18/553,625 mailed Oct. 2, 2025.
Non-Final Office Action for U.S. Appl. No. 18/556,945 mailed Dec. 19, 2025.
Non-Final Office Action for U.S. Appl. No. 18/562,626 mailed Feb. 11, 2026.
Non-Final Office Action for U.S. Appl. No. 18/563,672 mailed Feb. 12, 2026.
Non-Final Office Action for U.S. Appl. No. 18/662,216 mailed Mar. 9, 2026.
Non-Final Office Action for U.S. Appl. No. 18/682,006 mailed Mar. 4, 2026.
Non-Final Office Action for U.S. Appl. No. 18/689,532 mailed Mar. 19, 2026.
Non-Final Office Action for U.S. Appl. No. 18/690,392 mailed Feb. 9, 2026.
Non-Final Office Action for U.S. Appl. No. 18/694,090 mailed Mar. 17, 2026.
Non-Final Office Action for U.S. Appl. No. 18/757,964 mailed Aug. 20, 2025.
Non-Final Office Action for U.S. Appl. No. 29/892,478 mailed Mar. 12, 2026.
Notice of Allowance for U.S. Appl. No. 16/433,773 mailed Oct. 10, 2025.
Notice of Allowance for U.S. Appl. No. 17/051,399 mailed Nov. 17, 2025.

(56) References Cited

OTHER PUBLICATIONS

Notice of Allowance for U.S. Appl. No. 17/051,600 mailed Jan. 5, 2026.
Notice of Allowance for U.S. Appl. No. 17/394,055 mailed Mar. 20, 2026.
Notice of Allowance for U.S. Appl. No. 17/444,792 mailed Mar. 28, 2025.
Notice of Allowance for U.S. Appl. No. 17/451,345 mailed Jun. 24, 2025.
Notice of Allowance for U.S. Appl. No. 17/451,354 mailed Nov. 18, 2025.
Notice of Allowance for U.S. Appl. No. 17/596,629 mailed Jan. 29, 2025.
Notice of Allowance for U.S. Appl. No. 17/596,629 mailed May 27, 2025.
Notice of Allowance for U.S. Appl. No. 17/597,673 mailed Feb. 26, 2025.
Notice of Allowance for U.S. Appl. No. 17/625,887 mailed Mar. 3, 2026.
Notice of Allowance for U.S. Appl. No. 17/625,941 mailed Nov. 13, 2025.
Notice of Allowance for U.S. Appl. No. 17/635,866 mailed Mar. 2, 2026.
Notice of Allowance for U.S. Appl. No. 17/645,821 mailed Nov. 24, 2025.
Notice of Allowance for U.S. Appl. No. 17/653,137 mailed Oct. 22, 2025.
Notice of Allowance for U.S. Appl. No. 17/653,314 mailed Oct. 20, 2025.
Notice of Allowance for U.S. Appl. No. 17/653,920 mailed Jul. 9, 2025.
Notice of Allowance for U.S. Appl. No. 17/749,340 mailed Feb. 14, 2025.
Notice of Allowance for U.S. Appl. No. 17/754,736 mailed Jan. 28, 2026.
Notice of Allowance for U.S. Appl. No. 17/755,236 mailed Jul. 17, 2025.
Notice of Allowance for U.S. Appl. No. 17/758,316 mailed Mar. 24, 2025.
Notice of Allowance for U.S. Appl. No. 17/759,697 mailed Jan. 30, 2026.
Notice of Allowance for U.S. Appl. No. 17/808,354 mailed Nov. 12, 2025.
Notice of Allowance for U.S. Appl. No. 17/878,268 mailed Oct. 15, 2025.
Notice of Allowance for U.S. Appl. No. 17/907,125 mailed Sep. 26, 2025.
Notice of Allowance for U.S. Appl. No. 17/912,147 mailed Dec. 3, 2025.
Notice of Allowance for U.S. Appl. No. 17/930,238 mailed Dec. 16, 2025.
Notice of Allowance for U.S. Appl. No. 17/996,064 mailed Jul. 29, 2025.
Notice of Allowance for U.S. Appl. No. 17/996,155 mailed Jun. 24, 2025.
Notice of Allowance for U.S. Appl. No. 17/996,155 mailed Mar. 11, 2025.
Notice of Allowance for U.S. Appl. No. 17/996,253 mailed Apr. 11, 2025.
Notice of Allowance for U.S. Appl. No. 17/996,253 mailed Jul. 11, 2025.
Notice of Allowance for U.S. Appl. No. 17/996,468 mailed Apr. 14, 2025.
Notice of Allowance for U.S. Appl. No. 17/996,468 mailed Jul. 15, 2025.
Notice of Allowance for U.S. Appl. No. 18/007,105 mailed Jun. 17, 2025.
Notice of Allowance for U.S. Appl. No. 18/044,413 mailed Sep. 16, 2025.
Notice of Allowance for U.S. Appl. No. 18/134,857 mailed Feb. 20, 2025.
Notice of Allowance for U.S. Appl. No. 18/260,122 mailed Jul. 30, 2025.
Notice of Allowance for U.S. Appl. No. 18/264,004 mailed Jan. 30, 2026.
Notice of Allowance for U.S. Appl. No. 18/294,370 mailed Mar. 17, 2026.
Notice of Allowance for U.S. Appl. No. 18/610,523 mailed Mar. 4, 2026.
Restriction Requirement for U.S. Appl. No. 17/625,887 mailed Sep. 2, 2025.
Restriction Requirement for U.S. Appl. No. 17/755,236 mailed Apr. 24, 2025.
Restriction Requirement for U.S. Appl. No. 17/929,887 mailed Mar. 10, 2025.
Restriction Requirement for U.S. Appl. No. 17/930,238 mailed Apr. 17, 2025.
Restriction Requirement for U.S. Appl. No. 17/996,556 mailed Aug. 11, 2025.
Restriction Requirement for U.S. Appl. No. 18/034,902 mailed Nov. 6, 2025.
Restriction Requirement for U.S. Appl. No. 18/041,109 mailed Jun. 4, 2025.
Restriction Requirement for U.S. Appl. No. 18/041,109 mailed Oct. 23, 2025.
Restriction Requirement for U.S. Appl. No. 18/150,360 mailed May 19, 2025.
Restriction Requirement for U.S. Appl. No. 18/246,121 mailed Jul. 25, 2025.
Restriction Requirement for U.S. Appl. No. 18/249,577 mailed Aug. 25, 2025.
Restriction Requirement for U.S. Appl. No. 18/254,638 mailed Jul. 21, 2025.
Restriction Requirement for U.S. Appl. No. 18/260,394 mailed Jul. 25, 2025.
Restriction Requirement for U.S. Appl. No. 18/294,370 mailed Nov. 26, 2025.
Restriction Requirement for U.S. Appl. No. 18/294,403 mailed Jan. 27, 2026.
Restriction Requirement for U.S. Appl. No. 18/335,579 mailed Nov. 26, 2025.
Restriction Requirement for U.S. Appl. No. 18/373,424 mailed Nov. 14, 2025.
Restriction Requirement for U.S. Appl. No. 18/376,274 mailed Dec. 10, 2025.
Restriction Requirement for U.S. Appl. No. 18/549,387 mailed Dec. 9, 2025.
Restriction Requirement for U.S. Appl. No. 18/551,492 mailed Nov. 10, 2025.
Restriction Requirement for U.S. Appl. No. 18/569,711 mailed Jan. 6, 2026.
Restriction Requirement for U.S. Appl. No. 18/569,778 mailed Jan. 15, 2026.
Restriction Requirement for U.S. Appl. No. 18/662,216 mailed Nov. 26, 2025.
Restriction Requirement for U.S. Appl. No. 19/237,638 mailed Dec. 18, 2025.
Supplemental Notice of Allowance for U.S. Appl. No. 17/597,673 mailed Apr. 10, 2025.
U.S. Appl. No. 17/051,399, filed Oct. 28, 2020.
U.S. Appl. No. 17/596,629, filed Dec. 15, 2021.
U.S. Appl. No. 17/625,941, filed Jan. 10, 2022.
U.S. Appl. No. 18/034,902, filed May 2, 2023.
U.S. Appl. No. 19/039,165 filed Jan. 28, 2025.
U.S. Appl. No. 19/046,047, filed Feb. 5, 2025.
U.S. Appl. No. 19/047,728, filed Feb. 7, 2025.
U.S. Appl. No. 19/048,004, filed Feb. 7, 2025.
U.S. Appl. No. 19/049,501, filed Feb. 10, 2025.
U.S. Appl. No. 19/049,783, filed Feb. 10, 2025.
U.S. Appl. No. 19/058,726, filed Feb. 20, 2025.
U.S. Appl. No. 19/069,480, filed Mar. 4, 2025.
U.S. Appl. No. 19/078,602, filed Mar. 13, 2025.

(56) References Cited

OTHER PUBLICATIONS

U.S. Appl. No. 19/092,262, filed Mar. 27, 2025.
U.S. Appl. No. 19/103,165, filed Feb. 11, 2025.
U.S. Appl. No. 19/110,938, filed Mar. 12, 2025.
U.S. Appl. No. 19/111,921, filed Mar. 14, 2025.
U.S. Appl. No. 19/127,234, filed May 5, 2025.
U.S. Appl. No. 19/171,983, filed Apr. 7, 2025.
U.S. Appl. No. 19/179,540, filed Apr. 15, 2025.
U.S. Appl. No. 19/202,862, filed May 8, 2025.
U.S. Appl. No. 19/207,699, filed May 14, 2025.
U.S. Appl. No. 19/215,723, filed May 22, 2025.
U.S. Appl. No. 19/237,368, filed Jun. 13, 2025.
U.S. Appl. No. 19/240,380, filed Jun. 17, 2025.
U.S. Appl. No. 19/329,723, filed Sep. 16, 2025.
U.S. Appl. No. 19/337,217, filed Sep. 23, 2025.
U.S. Appl. No. 19/353,151, filed Oct. 8, 2025.
U.S. Appl. No. 19/356,506, filed Oct. 13, 2025.
U.S. Appl. No. 19/358,647, filed Oct. 15, 2025.
U.S. Appl. No. 19/370,361, filed Oct. 27, 2025.
U.S. Appl. No. 19/418,150, filed Dec. 12, 2025.
U.S. Appl. No. 19/443,729, filed Jan. 8, 2026.
U.S. Appl. No. 19/447,347, filed Jan. 13, 2026.
U.S. Appl. No. 19/451,614, filed Jan. 16, 2026.
U.S. Appl. No. 19/491,481, filed Dec. 9, 2025.
U.S. Appl. No. 19/494,631, filed Dec. 18, 2025.
U.S. Appl. No. 19/510,850, filed Feb. 12, 2026.
U.S. Appl. No. 19/513,755, filed Feb. 24, 2026.
U.S. Appl. No. 19/513,838, filed Feb. 24, 2026.
U.S. Appl. No. 19/514,100, filed Feb. 25, 2026.
U.S. Appl. No. 19/534,156, filed Feb. 9, 2026.
U.S. Appl. No. 19/535,649, filed Feb. 10, 2026.
U.S. Appl. No. 19/539,961, filed Feb. 13, 2026.
U.S. Appl. No. 19/541,655, filed Feb. 17, 2026.
U.S. Appl. No. 19/544,501, filed Feb. 19, 2026.
U.S. Appl. No. 19/554,125, filed Mar. 2, 2026.
“” Advisory Action for U.S. Appl. No. 14/952,591 mailed Jun. 1, 2018.
“” Advisory Action for U.S. Appl. No. 15/238,427 mailed Apr. 10, 2019.
“” Advisory Action for U.S. Appl. No. 16/245,726 mailed Apr. 19, 2023.
“” Advisory Action for U.S. Appl. No. 16/369,676 mailed Mar. 24, 2023.
“” Advisory Action for U.S. Appl. No. 16/433,773 mailed Feb. 15, 2023.
“” Advisory Action for U.S. Appl. No. 16/452,258 mailed Oct. 26, 2022.
“” Advisory Action for U.S. Appl. No. 16/478,180 mailed Sep. 21, 2022.
“” Advisory Action for U.S. Appl. No. 16/478,180 mailed Sep. 7, 2023.
“” Advisory Action for U.S. Appl. No. 16/899,956 mailed Jul. 9, 2021.
“” Advisory Action for U.S. Appl. No. 16/904,868 mailed Jul. 2, 2021.
“” Advisory Action for U.S. Appl. No. 16/904,868 mailed Jun. 15, 2022.
“” Advisory Action for U.S. Appl. No. 16/905,400 mailed Feb. 16, 2022.
“” Advisory Action for U.S. Appl. No. 16/905,400 mailed Jun. 9, 2021.
“” Advisory Action for U.S. Appl. No. 17/051,550 mailed Sep. 8, 2023.
“” Advisory Action for U.S. Appl. No. 17/051,585 mailed Oct. 17, 2023.
“” Advisory Action for U.S. Appl. No. 17/444,792 mailed Aug. 25, 2023.
“” Advisory Action for U.S. Appl. No. 17/451,345 mailed Oct. 20, 2023.
“” Advisory Action for U.S. Appl. No. 17/662,700 mailed Jan. 30, 2023.
“” Corrected International Search Report and Written Opinion for International Application No. PCT/US2017/043025 mailed Jan. 11, 2018.
“” Corrected Notice of Allowability for U.S. Appl. No. 15/221,106 mailed Jul. 2, 2019.
“” Corrected Notice of Allowability for U.S. Appl. No. 15/612,325 mailed Mar. 17, 2021.
“” Corrected Notice of Allowability for U.S. Appl. No. 17/330,657 mailed Dec. 9, 2021.
“” Final Office Action for U.S. Appl. No. 14/947,759 mailed Apr. 8, 2016.
“” Final Office Action for U.S. Appl. No. 14/952,591 mailed Feb. 23, 2018.
“” Final Office Action for U.S. Appl. No. 14/952,591 mailed Nov. 1, 2019.
“” Final Office Action for U.S. Appl. No. 14/952,591 mailed Nov. 27, 2020.
“” Final Office Action for U.S. Appl. No. 15/171,968 mailed Feb. 14, 2020.
“” Final Office Action for U.S. Appl. No. 15/171,968 mailed Mar. 19, 2019.
“” Final Office Action for U.S. Appl. No. 15/221,106 mailed Jan. 23, 2019.
“” Final Office Action for U.S. Appl. No. 15/238,427 mailed Jan. 2, 2019.
“” Final Office Action for U.S. Appl. No. 15/260,103 mailed Feb. 14, 2019.
“” Final Office Action for U.S. Appl. No. 15/612,325 mailed Sep. 17, 2020.
“” Final Office Action for U.S. Appl. No. 16/245,726 mailed Nov. 25, 2022.
“” Final Office Action for U.S. Appl. No. 16/369,676 mailed Aug. 31, 2023.
“” Final Office Action for U.S. Appl. No. 16/369,676 mailed Dec. 5, 2022.
“” Final Office Action for U.S. Appl. No. 16/433,773 mailed Oct. 10, 2023.
“” Final Office Action for U.S. Appl. No. 16/433,773 mailed Oct. 25, 2022.
“” Final Office Action for U.S. Appl. No. 16/449,039 mailed Aug. 1, 2022.
“” Final Office Action for U.S. Appl. No. 16/452,145 mailed Mar. 25, 2022.
“” Final Office Action for U.S. Appl. No. 16/452,258 mailed Jun. 14, 2022.
“” Final Office Action for U.S. Appl. No. 16/478,180 mailed Jun. 22, 2022.
“” Final Office Action for U.S. Appl. No. 16/478,180 mailed May 31, 2023.
“” Final Office Action for U.S. Appl. No. 16/899,956 mailed Apr. 19, 2021.
“” Final Office Action for U.S. Appl. No. 16/904,868 mailed Mar. 10, 2022.
“” Final Office Action for U.S. Appl. No. 16/904,868 mailed Mar. 26, 2021.
“” Final Office Action for U.S. Appl. No. 16/905,400 mailed Apr. 6, 2021.
“” Final Office Action for U.S. Appl. No. 16/905,400 mailed Dec. 9, 2021.
“” Final Office Action for U.S. Appl. No. 17/051,399 mailed Mar. 9, 2023.
“” Final Office Action for U.S. Appl. No. 17/051,550 mailed May 23, 2023.
“” Final Office Action for U.S. Appl. No. 17/051,585 mailed Jul. 27, 2023.
“” Final Office Action for U.S. Appl. No. 17/088,272 mailed May 25, 2021.
“” Final Office Action for U.S. Appl. No. 17/179,116 mailed Oct. 31, 2023.
“” Final Office Action for U.S. Appl. No. 17/444,792 mailed Jun. 15, 2023.

(56) References Cited

OTHER PUBLICATIONS

"" Final Office Action for U.S. Appl. No. 17/446,256 mailed Sep. 19, 2023.
"" Final Office Action for U.S. Appl. No. 17/448,811 mailed Aug. 3, 2023.
"" Final Office Action for U.S. Appl. No. 17/451,345 mailed May 3, 2023.
"" Final Office Action for U.S. Appl. No. 17/451,354 mailed Oct. 30, 2023.
"" Final Office Action for U.S. Appl. No. 17/453,260 mailed Oct. 5, 2023.
"" Final Office Action for U.S. Appl. No. 17/653,137 mailed Sep. 21, 2023.
"" Final Office Action for U.S. Appl. No. 17/655,464 mailed Sep. 1, 2023.
"" Final Office Action for U.S. Appl. No. 17/662,700 mailed Sep. 30, 2022.
"" Final Office Action for U.S. Appl. No. 29/624,661 mailed Feb. 18, 2020.
"" International Search Report and Written Opinion from International Application No. PCT/IB2021/057173 mailed Nov. 5, 2021.
"" International Search Report and Written Opinion from International Application No. PCT/US2016/049274 mailed Dec. 1, 2016.
"" International Search Report and Written Opinion from International Application No. PCT/US2017/035625 mailed Aug. 15, 2017.
"" International Search Report and Written Opinion from International Application No. PCT/US2017/043025 mailed Oct. 18, 2017.
"" International Search Report and Written Opinion from International Application No. PCT/US2018/015968 mailed Apr. 6, 2018.
"" International Search Report and Written Opinion from International Application No. PCT/US2019/029608 mailed Sep. 3, 2019.
"" International Search Report and Written Opinion from International Application No. PCT/US2019/029609 mailed Sep. 3, 2019.
"" International Search Report and Written Opinion from International Application No. PCT/US2019/029610 mailed Sep. 3, 2019.
"" International Search Report and Written Opinion from International Application No. PCT/US2019/029611 mailed Jul. 3, 2019.
"" International Search Report and Written Opinion from International Application No. PCT/US2019/029613 mailed Jul. 3, 2019.
"" International Search Report and Written Opinion from International Application No. PCT/US2019/029614 mailed Sep. 26, 2019.
"" International Search Report and Written Opinion from International Application No. PCT/US2019/029616 mailed Aug. 30, 2019.
"" International Search Report and Written Opinion from International Application No. PCT/US2020/023572 mailed Jul. 6, 2020.
"" International Search Report and Written Opinion from International Application No. PCT/US2020/033064 mailed Aug. 31, 2020.
"" International Search Report and Written Opinion from International Application No. PCT/US2020/033122 mailed Aug. 31, 2020.
"" International Search Report and Written Opinion from International Application No. PCT/US2020/040860 mailed Oct. 2, 2020.
"" International Search Report and Written Opinion from International Application No. PCT/US2020/041242 mailed Nov. 17, 2020.
"" International Search Report and Written Opinion from International Application No. PCT/US2020/041249 mailed Oct. 2, 2020.
"" International Search Report and Written Opinion from International Application No. PCT/US2020/042262 mailed Oct. 14, 2020.
"" International Search Report and Written Opinion from International Application No. PCT/US2020/043059 mailed Oct. 6, 2020.
"" International Search Report and Written Opinion from International Application No. PCT/US2020/044024 mailed Nov. 12, 2020.
"" International Search Report and Written Opinion from International Application No. PCT/US2020/046914 mailed Dec. 1, 2020.
"" International Search Report and Written Opinion from International Application No. PCT/US2020/055680 mailed Dec. 15, 2020.
"" International Search Report and Written Opinion from International Application No. PCT/US2020/057562 mailed Jan. 27, 2021.
"" International Search Report and Written Opinion from International Application No. PCT/US2020/061563 mailed Feb. 19, 2021.
"" International Search Report and Written Opinion from International Application No. PCT/US2020/065234 mailed Apr. 12, 2021.
"" International Search Report and Written Opinion from International Application No. PCT/US2020/067451 mailed Mar. 25, 2021.
"" International Search Report and Written Opinion from International Application No. PCT/US2020/067454 mailed Mar. 29, 2021.
"" International Search Report and Written Opinion from International Application No. PCT/US2020/067455 mailed Mar. 26, 2021.
"" International Search Report and Written Opinion from International Application No. PCT/US2021/015024 mailed May 18, 2021.
"" International Search Report and Written Opinion from International Application No. PCT/US2021/015787 mailed May 27, 2021.
"" International Search Report and Written Opinion from International Application No. PCT/US2021/023001 mailed Jun. 21, 2021.
"" International Search Report and Written Opinion from International Application No. PCT/US2021/024162 mailed Jul. 8, 2021.
"" International Search Report and Written Opinion from International Application No. PCT/US2021/026607 mailed Jul. 29, 2021.
"" International Search Report and Written Opinion from International Application No. PCT/US2021/027061 mailed Jul. 19, 2021.
"" International Search Report and Written Opinion from International Application No. PCT/US2021/027104 mailed Jul. 6, 2021.
"" International Search Report and Written Opinion from International Application No. PCT/US2021/027314 mailed Jul. 6, 2021.
"" International Search Report and Written Opinion from International Application No. PCT/US2021/027422 mailed Aug. 12, 2021.
"" International Search Report and Written Opinion from International Application No. PCT/US2021/027425 mailed Aug. 11, 2021.
"" International Search Report and Written Opinion from International Application No. PCT/US2021/027913 mailed Jul. 12, 2021.
"" International Search Report and Written Opinion from International Application No. PCT/US2021/027917 mailed Aug. 19, 2021.
"" International Search Report and Written Opinion from International Application No. PCT/US2021/039866 mailed Oct. 7, 2021.
"" International Search Report and Written Opinion from International Application No. PCT/US2021/043893 mailed Nov. 22, 2021.
"" International Search Report and Written Opinion from International Application No. PCT/US2021/044699 mailed Nov. 22, 2021.
"" International Search Report and Written Opinion from International Application No. PCT/US2021/045188 mailed Jan. 26, 2022.
"" International Search Report and Written Opinion from International Application No. PCT/US2021/047536 mailed Dec. 23, 2021.
"" International Search Report and Written Opinion from International Application No. PCT/US2021/048211 mailed Dec. 22, 2021.
"" International Search Report and Written Opinion from International Application No. PCT/US2021/048661 mailed Feb. 14, 2022.
"" International Search Report and Written Opinion from International Application No. PCT/US2021/049404 mailed Jan. 18, 2022.
"" International Search Report and Written Opinion from International Application No. PCT/US2021/051456 mailed Jan. 19, 2022.
"" International Search Report and Written Opinion from International Application No. PCT/US2021/053593 mailed Apr. 11, 2022.
"" International Search Report and Written Opinion from International Application No. PCT/US2021/055515 mailed Jan. 28, 2022.
"" International Search Report and Written Opinion from International Application No. PCT/US2021/056566 mailed Feb. 11, 2022.
"" International Search Report and Written Opinion from International Application No. PCT/US2021/060993 mailed Mar. 18, 2022.
"" International Search Report and Written Opinion from International Application No. PCT/US2021/062440 mailed Mar. 28, 2022.
"" International Search Report and Written Opinion from International Application No. PCT/US2022/011108 mailed Apr. 22, 2022.
"" International Search Report and Written Opinion from International Application No. PCT/US2022/011281 mailed Apr. 25, 2022.
"" International Search Report and Written Opinion from International Application No. PCT/US2022/011419 mailed Jun. 7, 2022.
"" International Search Report and Written Opinion from International Application No. PCT/US2022/011421 mailed Jun. 13, 2022.
"" International Search Report and Written Opinion from International Application No. PCT/US2022/012794 mailed May 3, 2022.
"" International Search Report and Written Opinion from International Application No. PCT/US2022/014285 mailed Sep. 28, 2022.

(56) References Cited

OTHER PUBLICATIONS

"" International Search Report and Written Opinion from International Application No. PCT/US2022/014749 mailed Sep. 28, 2022.
"" International Search Report and Written Opinion from International Application No. PCT/US2022/015026 mailed Oct. 31, 2022.
"" International Search Report and Written Opinion from International Application No. PCT/US2022/015045 mailed Sep. 9, 2022.
"" International Search Report and Written Opinion from International Application No. PCT/US2022/015073 mailed Sep. 8, 2022.
"" International Search Report and Written Opinion from International Application No. PCT/US2022/015418 mailed Nov. 11, 2022.
"" International Search Report and Written Opinion from International Application No. PCT/US2022/015420 mailed Nov. 18, 2022.
"" International Search Report and Written Opinion from International Application No., PCT/US2022/015471 mailed May 16, 2022.
"" International Search Report and Written Opinion from International Application No. PCT/US2022/015492 mailed Apr. 26, 2022.
"" International Search Report and Written Opinion from International Application No. PCT/US2022/015781 mailed May 6, 2022.
"" International Search Report and Written Opinion from International Application No. PCT/US2022/016942 mailed Jun. 8, 2022.
"" International Search Report and Written Opinion from International Application No. PCT/US2022/018159 mailed Dec. 12, 2022.
"" International Search Report and Written Opinion from International Application No. PCT/US2022/018170 mailed May 31, 2022.
"" International Search Report and Written Opinion from International Application No. PCT/US2022/019254 mailed Jun. 7, 2022.
"" International Search Report and Written Opinion from International Application No. PCT/US2022/019480 mailed Jun. 13, 2022.
"" International Search Report and Written Opinion from International Application No. PCT/US2022/021103 mailed Jun. 23, 2022.
"" International Search Report and Written Opinion from International Application No. PCT/US2022/022111 mailed Oct. 26, 2022.
"" International Search Report and Written Opinion from International Application No. PCT/US2022/023594 mailed Jul. 12, 2022.
"" International Search Report and Written Opinion from International Application No. PCT/US2022/026667 mailed Aug. 22, 2022.
"" International Search Report and Written Opinion from International Application No. PCT/US2022/030685 mailed Oct. 31, 2022.
"" International Search Report and Written Opinion from International Application No. PCT/US2022/031032 mailed Sep. 9, 2022.
"" International Search Report and Written Opinion from International Application No. PCT/US2022/032424 mailed Oct. 11, 2022.
"" International Search Report and Written Opinion from International Application No. PCT/US2022/034457 mailed Oct. 12, 2022.
"" International Search Report and Written Opinion from International Application No. PCT/US2022/034744 mailed Dec. 9, 2022.
"" International Search Report and Written Opinion from International Application No. PCT/US2022/039018 mailed Jan. 10, 2023.
"" International Search Report and Written Opinion from International Application No. PCT/US2022/039022 mailed Jan. 10, 2023.
"" International Search Report and Written Opinion from International Application No. PCT/US2022/039711 mailed Jan. 12, 2023.
"" International Search Report and Written Opinion from International Application No. PCT/US2022/039714 mailed Nov. 22, 2022.
"" International Search Report and Written Opinion from International Application No. PCT/US2022/041085 mailed Mar. 16, 2023.
"" International Search Report and Written Opinion from International Application No. PCT/US2022/041688 mailed Nov. 21, 2022.
"" International Search Report and Written Opinion from International Application No. PCT/US2022/042719 mailed Dec. 5, 2022.
"" International Search Report and Written Opinion from International Application No. PCT/US2022/042725 mailed Dec. 19, 2022.
"" International Search Report and Written Opinion from International Application No. PCT/US2022/043818 mailed Mar. 24, 2023.
"" International Search Report and Written Opinion from International Application No. PCT/US2022/044107 mailed Dec. 23, 2022.
"" International Search Report and Written Opinion from International Application No. PCT/US2022/044208 mailed May 8, 2023.
"" International Search Report and Written Opinion from International Application No. PCT/US2022/044212 mailed Jan. 20, 2023.
"" International Search Report and Written Opinion from International Application No. PCT/US2022/044243 mailed Feb. 24, 2023.
"" International Search Report and Written Opinion from International Application No. PCT/US2022/049300 mailed Jun. 6, 2023.
"" International Search Report and Written Opinion from International Application No. PCT/US2022/050909 mailed Jul. 24, 2023.
"" International Search Report and Written Opinion from International Application No. PCT/US2023/012696 mailed Jul. 6, 2023.
"" International Search Report and Written Opinion from International Application No. PCT/US2023/018474 mailed Sep. 11, 2023.
"" Issue Notification for U.S. Appl. No. 14/952,591 mailed Jul. 28, 2021.
"" Issue Notification for U.S. Appl. No. 15/171,968 mailed Mar. 3, 2021.
"" Issue Notification for U.S. Appl. No. 15/221,106 mailed Jul. 24, 2019.
"" Issue Notification for U.S. Appl. No. 15/238,427 mailed Jul. 24, 2019.
"" Issue Notification for U.S. Appl. No. 15/260,103 mailed Aug. 7, 2019.
"" Issue Notification for U.S. Appl. No. 15/611,587 mailed Feb. 20, 2019.
"" Issue Notification for U.S. Appl. No. 15/612,325 mailed Mar. 24, 2021.
"" Issue Notification for U.S. Appl. No. 16/245,726 mailed Oct. 18, 2023.
"" Issue Notification for U.S. Appl. No. 16/899,956 mailed Mar. 29, 2023.
"" Issue Notification for U.S. Appl. No. 16/905,400 mailed Nov. 30, 2022.
"" Issue Notification for U.S. Appl. No. 17/088,272 mailed Jun. 15, 2022.
"" Issue Notification for U.S. Appl. No. 17/330,657 mailed Jun. 22, 2022.
"" Issue Notification for U.S. Appl. No. 17/461,036 mailed Oct. 11, 2023.
"" Issue Notification for U.S. Appl. No. 29/624,661 mailed Aug. 4, 2021.
"" Non-Final Office Action for U.S. Appl. No. 14/947,759 mailed Mar. 17, 2016.
"" Non-Final Office Action for U.S. Appl. No. 14/952,591 mailed Aug. 1, 2017.
"" Non-Final Office Action for U.S. Appl. No. 14/952,591 mailed Mar. 20, 2020.
"" Non-Final Office Action for U.S. Appl. No. 14/952,591 mailed Mar. 21, 2019.
"" Non-Final Office Action for U.S. Appl. No. 14/952,591 mailed Sep. 28, 2018.
"" Non-Final Office Action for U.S. Appl. No. 15/171,968 mailed May 11, 2020.
"" Non-Final Office Action for U.S. Appl. No. 15/171,968 mailed Aug. 20, 2019.
"" Non-Final Office Action for U.S. Appl. No. 15/171,968 mailed Jun. 12, 2018.
"" Non-Final Office Action for U.S. Appl. No. 15/221,106 mailed Jun. 5, 2018.
"" Non-Final Office Action for U.S. Appl. No. 15/238,427 mailed Aug. 8, 2018.
"" Non-Final Office Action for U.S. Appl. No. 15/260,103 mailed Sep. 26, 2018.
"" Non-Final Office Action for U.S. Appl. No. 15/611,587 mailed Dec. 29, 2017.
"" Non-Final Office Action for U.S. Appl. No. 15/611,587 mailed Jul. 13, 2018.
"" Non-Final Office Action for U.S. Appl. No. 15/612,325 mailed Mar. 19, 2020.
"" Non-Final Office Action for U.S. Appl. No. 16/245,726 mailed Jan. 21, 2022.
"" Non-Final Office Action for U.S. Appl. No. 16/369,676 mailed Mar. 31, 2022.

(56) References Cited

OTHER PUBLICATIONS

"" Non-Final Office Action for U.S. Appl. No. 16/433,773 mailed Apr. 11, 2023.
"" Non-Final Office Action for U.S. Appl. No. 16/433,773 mailed Apr. 21, 2022.
"" Non-Final Office Action for U.S. Appl. No. 16/449,039 mailed Apr. 27, 2023.
"" Non-Final Office Action for U.S. Appl. No. 16/449,039 mailed Dec. 8, 2021.
"" Non-Final Office Action for U.S. Appl. No. 16/452,145 mailed Mar. 28, 2023.
"" Non-Final Office Action for U.S. Appl. No. 16/452,145 mailed Sep. 28, 2021.
"" Non-Final Office Action for U.S. Appl. No. 16/452,258 mailed Apr. 26, 2023.
"" Non-Final Office Action for U.S. Appl. No. 16/452,258 mailed Sep. 28, 2021.
"" Non-Final Office Action for U.S. Appl. No. 16/478,180 mailed Dec. 20, 2022.
"" Non-Final Office Action for U.S. Appl. No. 16/478,180 mailed Oct. 22, 2021.
"" Non-Final Office Action for U.S. Appl. No. 16/899,956 mailed Oct. 16, 2020.
"" Non-Final Office Action for U.S. Appl. No. 16/899,956 mailed Sep. 2, 2021.
"" Non-Final Office Action for U.S. Appl. No. 16/904,868 mailed Mar. 15, 2023.
"" Non-Final Office Action for U.S. Appl. No. 16/904,868 mailed Nov. 25, 2020.
"" Non-Final Office Action for U.S. Appl. No. 16/904,868 mailed Oct. 5, 2021.
"" Non-Final Office Action for U.S. Appl. No. 16/905,400 mailed Apr. 27, 2022.
"" Non-Final Office Action for U.S. Appl. No. 16/905,400 mailed Dec. 2, 2020.
"" Non-Final Office Action for U.S. Appl. No. 16/905,400 mailed Jul. 22, 2021.
"" Non-Final Office Action for U.S. Appl. No. 17/051,399 mailed Aug. 18, 2023.
"" Non-Final Office Action for U.S. Appl. No. 17/051,550 mailed Dec. 15, 2022.
"" Non-Final Office Action for U.S. Appl. No. 17/051,550 mailed Oct. 24, 2023.
"" Non-Final Office Action for U.S. Appl. No. 17/051,585 mailed Mar. 29, 2023.
"" Non-Final Office Action for U.S. Appl. No. 17/088,272 mailed Jan. 25, 2021.
"" Non-Final Office Action for U.S. Appl. No. 17/179,116 mailed Mar. 24, 2023.
"" Non-Final Office Action for U.S. Appl. No. 17/326,980 mailed Jul. 11, 2023.
"" Non-Final Office Action for U.S. Appl. No. 17/330,657 mailed Aug. 11, 2021.
"" Non-Final Office Action for U.S. Appl. No. 17/444,792 mailed Feb. 10, 2023.
"" Non-Final Office Action for U.S. Appl. No. 17/446,256 mailed Apr. 13, 2023.
"" Non-Final Office Action for U.S. Appl. No. 17/446,654 mailed Sep. 8, 2023.
"" Non-Final Office Action for U.S. Appl. No. 17/448,811 mailed Mar. 1, 2023.
"" Non-Final Office Action for U.S. Appl. No. 17/450,864 mailed May 10, 2023.
"" Non-Final Office Action for U.S. Appl. No. 17/451,345 mailed Dec. 7, 2022.
"" Non-Final Office Action for U.S. Appl. No. 17/451,354 mailed May 3, 2023.
"" Non-Final Office Action for U.S. Appl. No. 17/453,260 mailed Mar. 14, 2023.
"" Non-Final Office Action for U.S. Appl. No. 17/453,560 mailed Oct. 16, 2023.
"" Non-Final Office Action for U.S. Appl. No. 17/501,591 mailed Apr. 25, 2023.
"" Non-Final Office Action for U.S. Appl. No. 17/645,821 mailed Oct. 25, 2023.
"" Non-Final Office Action for U.S. Appl. No. 17/646,771 mailed Jul. 5, 2023.
"" Non-Final Office Action for U.S. Appl. No. 17/653,137 mailed Apr. 7, 2023.
"" Non-Final Office Action for U.S. Appl. No. 17/655,464 mailed Mar. 14, 2023.
"" Non-Final Office Action for U.S. Appl. No. 17/657,474 mailed Sep. 12, 2023.
"" Non-Final Office Action for U.S. Appl. No. 17/661,090 mailed Jul. 6, 2023.
"" Non-Final Office Action for U.S. Appl. No. 17/662,700 mailed Jul. 22, 2022.
"" Non-Final Office Action for U.S. Appl. No. 17/663,330 mailed Jun. 29, 2023.
"" Non-Final Office Action for U.S. Appl. No. 17/664,487 mailed Jun. 8, 2023.
"" Non-Final Office Action for U.S. Appl. No. 18/139,523 mailed Aug. 17, 2023.
"" Non-Final Office Action for U.S. Appl. No. 18/140,751 mailed Sep. 14, 2023.
"" Non-Final Office Action for U.S. Appl. No. 29/624,661 mailed Jul. 18, 2019.
"" Non-Final Office Action for U.S. Appl. No. 29/694,002 mailed Jun. 24, 2020.
"" Non-Final Office Action for U.S. Appl. No. 29/741,751 mailed Jan. 18, 2022.
"" Notice of Allowance for U.S. Appl. No. 14/952,591 mailed Apr. 5, 2021.
"" Notice of Allowance for U.S. Appl. No. 14/952,591 mailed Jul. 8, 2021.
"" Notice of Allowance for U.S. Appl. No. 15/171,968 mailed Feb. 16, 2021.
"" Notice of Allowance for U.S. Appl. No. 15/171,968 mailed Nov. 6, 2020.
"" Notice of Allowance for U.S. Appl. No. 15/221,106 mailed May 1, 2019.
"" Notice of Allowance for U.S. Appl. No. 15/238,427 mailed May 23, 2019.
"" Notice of Allowance for U.S. Appl. No. 15/260,103 mailed Jun. 7, 2019.
"" Notice of Allowance for U.S. Appl. No. 15/611,587 mailed Dec. 21, 2018.
"" Notice of Allowance for U.S. Appl. No. 15/612,325 mailed Feb. 19, 2021.
"" Notice of Allowance for U.S. Appl. No. 15/612,325 mailed Jan. 21, 2021.
"" Notice of Allowance for U.S. Appl. No. 16/245,726 mailed Jul. 6, 2023.
"" Notice of Allowance for U.S. Appl. No. 16/449,039 mailed Dec. 15, 2022.
"" Notice of Allowance for U.S. Appl. No. 16/899,956 mailed Apr. 19, 2022.
"" Notice of Allowance for U.S. Appl. No. 16/899,956 mailed Aug. 10, 2022.
"" Notice of Allowance for U.S. Appl. No. 16/899,956 mailed Dec. 1, 2022.
"" Notice of Allowance for U.S. Appl. No. 16/899,956 mailed Dec. 29, 2021.
"" Notice of Allowance for U.S. Appl. No. 16/905,400 mailed Aug. 17, 2022.
"" Notice of Allowance for U.S. Appl. No. 17/051,554 mailed Jul. 6, 2023.
"" Notice of Allowance for U.S. Appl. No. 17/051,554 mailed Oct. 18, 2023.
"" Notice of Allowance for U.S. Appl. No. 17/088,272 mailed Aug. 5, 2021.

(56) References Cited

OTHER PUBLICATIONS

"" Notice of Allowance for U.S. Appl. No. 17/088,272 mailed Mar. 4, 2022.
"" Notice of Allowance for U.S. Appl. No. 17/088,272 mailed Nov. 24, 2021.
"" Notice of Allowance for U.S. Appl. No. 17/330,657 mailed Mar. 16, 2022.
"" Notice of Allowance for U.S. Appl. No. 17/330,657 mailed Nov. 26, 2021.
"" Notice of Allowance for U.S. Appl. No. 17/461,036 mailed Feb. 22, 2023.
"" Notice of Allowance for U.S. Appl. No. 17/461,036 mailed Jun. 30, 2023.
"" Notice of Allowance for U.S. Appl. No. 17/461,036 mailed Oct. 6, 2022.
"" Notice of Allowance for U.S. Appl. No. 17/662,700 mailed Jul. 28, 2023.
"" Notice of Allowance for U.S. Appl. No. 17/662,700 mailed Mar. 28, 2023.
"" Notice of Allowance for U.S. Appl. No. 17/663,046 mailed Jan. 30, 2023.
"" Notice of Allowance for U.S. Appl. No. 18/299,788 mailed Jul. 24, 2023.
"" Notice of Allowance for U.S. Appl. No. 29/624,661 mailed Apr. 28, 2021.
"" Notice of Allowance for U.S. Appl. No. 29/624,661 mailed Jul. 10, 2020.
"" Notice of Allowance for U.S. Appl. No. 29/624,661 mailed May 14, 2020.
"" Notice of Allowance for U.S. Appl. No. 29/624,661 mailed Sep. 29, 2020.
"" Notice of Allowance for U.S. Appl. No. 29/694,002 mailed Apr. 29, 2021.
"" Notice of Allowance for U.S. Appl. No. 29/694,002 mailed Jan. 29, 2021.
"" Notice of Allowance for U.S. Appl. No. 29/694,002 mailed Oct. 16, 2020.
"" Notice of Allowance for U.S. Appl. No. 29/741,751 mailed Jun. 9, 2022.
"" Notice to File Missing Parts for U.S. Appl. No. 17/179,116 mailed Mar. 3, 2021.
"" Restriction Requirement for U.S. Appl. No. 16/433,773 mailed Dec. 7, 2021.
"" Restriction Requirement for U.S. Appl. No. 16/478,180 mailed May 25, 2021.
"" Restriction Requirement for U.S. Appl. No. 17/051,600 mailed Sep. 21, 2023.
"" Restriction Requirement for U.S. Appl. No. 17/326,980 mailed Mar. 20, 2023.
"" Restriction Requirement for U.S. Appl. No. 17/446,256 mailed Jan. 23, 2023.
"" Restriction Requirement for U.S. Appl. No. 17/645,821 mailed Jul. 12, 2023.
"" Restriction Requirement for U.S. Appl. No. 17/646,771 mailed Apr. 6, 2023.
"" Restriction Requirement for U.S. Appl. No. 17/657,474 mailed Jun. 30, 2023.
"" Restriction Requirement for U.S. Appl. No. 18/134,857 mailed Oct. 23, 2023.
"" Text Messages to Lorena Eckert Re Prototype PureWick Holder dated Apr. 16, 2022.
"" U.S. Appl. No. 14/625,469, filed Feb. 28, 2015.
"" U.S. Appl. No. 14/947,759, filed Nov. 20, 2015.
"" U.S. Appl. No. 14/952,591, filed Nov. 25, 2015.
"" U.S. Appl. No. 15/171,968, filed Jun. 2, 2016.
"" U.S. Appl. No. 15/221,106, filed Jul. 27, 2016.
"" U.S. Appl. No. 15/260,103, filed Sep. 8, 2016.
"" U.S. Appl. No. 15/384,196, filed Dec. 19, 2016.
"" U.S. Appl. No. 15/611,587, filed Jun. 1, 2017 ,.
"" U.S. Appl. No. 15/612,325, filed Jun. 2, 2017.
"" U.S. Appl. No. 16/245,726, filed Jan. 11, 2019.
"" U.S. Appl. No. 16/369,676, filed Mar. 29, 2019.
"" U.S. Appl. No. 16/433,773, filed Jun. 6, 2019.
"" U.S. Appl. No. 16/449,039, filed Jun. 21, 2019.
"" U.S. Appl. No. 16/452,145, filed Jun. 25, 2019.
"" U.S. Appl. No. 16/452,258, filed Jun. 25, 2019.
"" U.S. Appl. No. 16/478,180, filed Jul. 16, 2019.
"" U.S. Appl. No. 16/904,868, filed Jun. 18, 2020.
"" U.S. Appl. No. 16/905,400, filed Jun. 18, 2020.
"" U.S. Appl. No. 17/051,550, filed Oct. 29, 2020.
"" U.S. Appl. No. 17/051,554, filed Oct. 29, 2020.
"" U.S. Appl. No. 17/051,585, filed Oct. 29, 2020.
"" U.S. Appl. No. 17/051,600, filed Oct. 29, 2020.
"" U.S. Appl. No. 17/088,272, filed Nov. 3, 2020.
"" U.S. Appl. No. 17/179,116, filed Feb. 18, 2021.
"" U.S. Appl. No. 17/330,657, filed May 26, 2021.
"" U.S. Appl. No. 17/378,015, filed Jul. 16, 2021.
"" U.S. Appl. No. 17/394,055, filed Aug. 4, 2021.
"" U.S. Appl. No. 17/444,825, filed Aug. 10, 2021.
"" U.S. Appl. No. 17/446,256, filed Aug. 27, 2021.
"" U.S. Appl. No. 17/446,654, filed Sep. 1, 2021.
"" U.S. Appl. No. 17/447,123, filed Sep. 8, 2021.
"" U.S. Appl. No. 17/450,864, filed Oct. 14, 2021.
"" U.S. Appl. No. 17/451,345, filed Oct. 19, 2021.
"" U.S. Appl. No. 17/451,354, filed Oct. 19, 2021.
"" U.S. Appl. No. 17/453,260, filed Nov. 2, 2021.
"" U.S. Appl. No. 17/453,560, filed Nov. 4, 2021.
"" U.S. Appl. No. 17/461,036 mailed Aug. 30, 2021.
"" U.S. Appl. No. 17/501,591, filed Oct. 14, 2021.
"" U.S. Appl. No. 17/595,747, filed Nov. 23, 2021.
"" U.S. Appl. No. 17/597,408, filed Jan. 5, 2022.
"" U.S. Appl. No. 17/597,673, filed Jan. 18, 2022.
"" U.S. Appl. No. 17/614,173, filed Nov. 24, 2021.
"" U.S. Appl. No. 17/631,619, filed Jan. 31, 2022.
"" U.S. Appl. No. 17/645,821, filed Dec. 23, 2021.
"" U.S. Appl. No. 17/646,771, filed Jan. 3, 2022.
"" U.S. Appl. No. 17/653,314, filed Mar. 3, 2022.
"" U.S. Appl. No. 17/653,920, filed Mar. 8, 2022 ,.
"" U.S. Appl. No. 17/655,464, filed Mar. 18, 2022.
"" U.S. Appl. No. 17/657,474, filed Mar. 31, 2022.
"" U.S. Appl. No. 17/661,090, filed Apr. 28, 2022.
"" U.S. Appl. No. 17/662,700, filed May 10, 2022.
"" U.S. Appl. No. 17/663,046, filed May 12, 2022.
"" U.S. Appl. No. 17/664,487, filed May 23, 2022.
"" U.S. Appl. No. 17/664,914, filed May 25, 2022.
"" U.S. Appl. No. 17/749,340, filed May 20, 2022.
"" U.S. Appl. No. 17/754,736, filed Apr. 11, 2022.
"" U.S. Appl. No. 17/756,201, filed May 19, 2022.
"" U.S. Appl. No. 17/758,152, filed Jun. 29, 2022.
"" U.S. Appl. No. 17/758,316, filed Jul. 1, 2022.
"" U.S. Appl. No. 17/759,697, filed Jul. 28, 2022.
"" U.S. Appl. No. 17/878,268, filed Aug. 1, 2022.
"" U.S. Appl. No. 17/907,125, filed Sep. 23, 2022.
"" U.S. Appl. No. 17/912,147, filed Sep. 16, 2022.
"" U.S. Appl. No. 17/929,887, filed Sep. 6, 2022.
"" U.S. Appl. No. 17/930,238, filed Sep. 7, 2022.
"" U.S. Appl. No. 17/933,590, filed Sep. 20, 2022.
"" U.S. Appl. No. 17/996,064, filed Oct. 12, 2022.
"" U.S. Appl. No. 17/996,155, filed Oct. 13, 2022.
"" U.S. Appl. No. 17/996,253, filed Oct. 14, 2022.
"" U.S. Appl. No. 17/996,468, filed Oct. 18, 2022.
"" U.S. Appl. No. 17/996,556, filed Oct. 19, 2022.
"" U.S. Appl. No. 18/003,029, filed Dec. 22, 2022.
"" U.S. Appl. No. 18/006,807, filed Jan. 25, 2023.
"" U.S. Appl. No. 18/007,105, filed Jan. 27, 2023.
"" U.S. Appl. No. 18/041,109, filed Feb. 9, 2023.
"" U.S. Appl. No. 18/042,842, filed Feb. 24, 2023.
"" U.S. Appl. No. 18/043,618, filed Mar. 1, 2023.
"" U.S. Appl. No. 18/115,444, filed Feb. 28, 2023.
"" U.S. Appl. No. 18/134,857, filed Apr. 14, 2023.
"" U.S. Appl. No. 18/140,163, filed Apr. 27, 2023.
"" U.S. Appl. No. 18/140,751, filed Apr. 28, 2023.
"" U.S. Appl. No. 18/164,800, filed Feb. 6, 2023.

(56) References Cited

OTHER PUBLICATIONS

"" U.S. Appl. No. 18/198,464, filed May 17, 2023.
"" U.S. Appl. No. 18/246,121, filed Mar. 21, 2023.
"" U.S. Appl. No. 18/247,986, filed Apr. 5, 2023.
"" U.S. Appl. No. 18/259,626, filed Jun. 28, 2023.
"" U.S. Appl. No. 18/260,122, filed Jun. 30, 2023.
"" U.S. Appl. No. 18/260,391, filed Jul. 5, 2023.
"" U.S. Appl. No. 18/260,394, filed Jul. 5, 2023.
"" U.S. Appl. No. 18/263,800, filed Aug. 1, 2023.
"" U.S. Appl. No. 18/264,004, filed Aug. 2, 2023.
"" U.S. Appl. No. 18/265,736, filed Jun. 7, 2023.
"" U.S. Appl. No. 18/299,788, filed Apr. 13, 2023.
"" U.S. Appl. No. 18/335,579, filed Jun. 15, 2023.
"" U.S. Appl. No. 18/373,424, filed Sep. 27, 2023.
"" U.S. Appl. No. 18/376,274, filed Oct. 3, 2023.
"" U.S. Appl. No. 18/548,152, filed Aug. 28, 2023.
"" U.S. Appl. No. 18/549,387, filed Sep. 7, 2023.
"" U.S. Appl. No. 18/549,658, filed Sep. 8, 2023.
"" U.S. Appl. No. 18/553,625, filed Oct. 2, 2023.
"" U.S. Appl. No. 18/556,945, filed Oct. 24, 2023.
"" U.S. Appl. No. 29/741,751, filed Jul. 15, 2020.
"" U.S. Appl. No. 61/955,537, filed Mar. 19, 2014.
"" U.S. Appl. No. 62/082,279, filed Nov. 20, 2014.
"" U.S. Appl. No. 62/084,078, filed Nov. 25, 2014.
"" U.S. Appl. No. 62/414,963, filed Oct. 31, 2016.
"" U.S. Appl. No. 62/452,437, filed Jan. 31, 2017.
"" U.S. Appl. No. 62/485,578, filed Apr. 14, 2017.
"" U.S. Appl. No. 62/665,297, filed May 1, 2018.
"" U.S. Appl. No. 62/665,302, filed May 1, 2018.
"" U.S. Appl. No. 62/665,317, filed May 1, 2018.
"" U.S. Appl. No. 62/665,321, filed May 1, 2018.
"" U.S. Appl. No. 62/665,331, filed May 1, 2018.
"" U.S. Appl. No. 62/665,335, filed May 1, 2018.
"" U.S. Appl. No. 62/853,279, filed May 28, 2019.
"" U.S. Appl. No. 62/853,889, filed May 29, 2019.
"" U.S. Appl. No. 62/864,656, filed Jun. 21, 2019.
"" U.S. Appl. No. 62/873,045, filed Jul. 11, 2019.
"" U.S. Appl. No. 62/873,048, filed Jul. 11, 2019.
"" U.S. Appl. No. 62/876,500, filed Jul. 19, 2019 ,.
"" U.S. Appl. No. 62/877,558, filed Jul. 23, 2019.
"" U.S. Appl. No. 62/883,172, filed Aug. 6, 2019.
"" U.S. Appl. No. 62/889,149, filed Aug. 20, 2019.
"" U.S. Appl. No. 62/923,279, filed Oct. 18, 2019.
"" U.S. Appl. No. 62/926,767, filed Oct. 28, 2019.
"" U.S. Appl. No. 62/935,337, filed Nov. 14, 2019.
"" U.S. Appl. No. 62/938,447, filed Nov. 21, 2019.
"" U.S. Appl. No. 62/949,187, filed Dec. 17, 2019.
"" U.S. Appl. No. 62/956,756, filed Jan. 3, 2020.
"" U.S. Appl. No. 62/956,767, filed Jan. 3, 2020.
"" U.S. Appl. No. 62/956,770, filed Jan. 3, 2020.
"" U.S. Appl. No. 62/967,158, filed Jan. 26, 2020.
"" U.S. Appl. No. 62/967,977, filed Jan. 30, 2020.
"" U.S. Appl. No. 62/991,754, filed Mar. 19, 2020.
"" U.S. Appl. No. 62/994,912, filed Mar. 26, 2020.
"" U.S. Appl. No. 63/008,112, filed Apr. 10, 2020.
"" U.S. Appl. No. 63/011,445, filed Apr. 17, 2020.
"" U.S. Appl. No. 63/011,487, filed Apr. 17, 2020.
"" U.S. Appl. No. 63/011,571, filed Apr. 17, 2020.
"" U.S. Appl. No. 63/011,657, filed Apr. 17, 2020.
"" U.S. Appl. No. 63/011,760, filed Apr. 17, 2020.
"" U.S. Appl. No. 63/012,347, filed Apr. 20, 2020.
"" U.S. Appl. No. 63/012,384, filed Apr. 20, 2020.
"" U.S. Appl. No. 63/030,685, filed May 27, 2020.
"" U.S. Appl. No. 63/047,374, filed Jul. 2, 2020.
"" U.S. Appl. No. 63/061,241, filed Aug. 5, 2020.
"" U.S. Appl. No. 63/061,244, filed Aug. 5, 2020.
"" U.S. Appl. No. 63/061,834, filed Aug. 6, 2020.
"" U.S. Appl. No. 63/064,017, filed Aug. 11, 2020.
"" U.S. Appl. No. 63/064,126, filed Aug. 11, 2020.
"" U.S. Appl. No. 63/067,542, filed Aug. 19, 2020.
"" U.S. Appl. No. 63/071,438, filed Aug. 28, 2020.
"" U.S. Appl. No. 63/073,545, filed Sep. 2, 2020.
"" U.S. Appl. No. 63/073,553, filed Sep. 2, 2020.
"" U.S. Appl. No. 63/074,051, filed Sep. 3, 2020.
"" U.S. Appl. No. 63/074,066, filed Sep. 3, 2020.
"" U.S. Appl. No. 63/076,032, filed Sep. 9, 2020.
"" U.S. Appl. No. 63/076,474, filed Sep. 10, 2020.
"" U.S. Appl. No. 63/076,477, filed Sep. 10, 2020.
"" U.S. Appl. No. 63/082,261, filed Sep. 23, 2020.
"" U.S. Appl. No. 63/088,506, filed Oct. 7, 2020.
"" U.S. Appl. No. 63/088,511, filed Oct. 7, 2020.
"" U.S. Appl. No. 63/094,464, filed Oct. 21, 2020.
"" U.S. Appl. No. 63/094,498, filed Oct. 21, 2020.
"" U.S. Appl. No. 63/094,594, filed Oct. 21, 2020.
"" U.S. Appl. No. 63/094,608, filed Oct. 21, 2020.
"" U.S. Appl. No. 63/094,626, filed Oct. 21, 2020.
"" U.S. Appl. No. 63/094,646, filed Oct. 21, 2020.
"" U.S. Appl. No. 63/109,066, filed Nov. 3, 2020.
"" U.S. Appl. No. 63/109,084, filed Nov. 3, 2020.
"" U.S. Appl. No. 63/112,417, filed Nov. 11, 2020.
"" U.S. Appl. No. 63/119,161, filed Nov. 30, 2020.
"" U.S. Appl. No. 63/124,271, filed Dec. 11, 2020.
"" U.S. Appl. No. 63/133,892, filed Jan. 5, 2021.
"" U.S. Appl. No. 63/134,287, filed Jan. 6, 2021.
"" U.S. Appl. No. 63/134,450, filed Jan. 6, 2021.
"" U.S. Appl. No. 63/134,631, filed Jan. 7, 2021.
"" U.S. Appl. No. 63/134,632, filed Jan. 7, 2021.
"" U.S. Appl. No. 63/134,754, filed Jan. 7, 2021.
"" U.S. Appl. No. 63/138,878, filed Jan. 19, 2021.
"" U.S. Appl. No. 63/146,946, filed Feb. 8, 2021.
"" U.S. Appl. No. 63/147,013, filed Feb. 8, 2021.
"" U.S. Appl. No. 63/147,299, filed Feb. 9, 2021.
"" U.S. Appl. No. 63/148,723, filed Feb. 12, 2021.
"" U.S. Appl. No. 63/150,640, filed Feb. 18, 2021.
"" U.S. Appl. No. 63/154,248, filed Feb. 26, 2021.
"" U.S. Appl. No. 63/155,395, filed Mar. 2, 2021.
"" U.S. Appl. No. 63/157,007, filed Mar. 5, 2021.
"" U.S. Appl. No. 63/157,014, filed Mar. 5, 2021.
"" U.S. Appl. No. 63/159,142, filed Mar. 10, 2021.
"" U.S. Appl. No. 63/159,186, filed Mar. 10, 2021.
"" U.S. Appl. No. 63/159,210, filed Mar. 10, 2021.
"" U.S. Appl. No. 63/165,273, filed Mar. 24, 2021.
"" U.S. Appl. No. 63/165,384, filed Mar. 24, 2021.
"" U.S. Appl. No. 63/171,165, filed Apr. 6, 2021.
"" U.S. Appl. No. 63/172,975, filed Apr. 9, 2021.
"" U.S. Appl. No. 63/181,695, filed Apr. 29, 2021.
"" U.S. Appl. No. 63/191,558, filed May 21, 2021.
"" U.S. Appl. No. 63/192,274, filed May 24, 2021.
"" U.S. Appl. No. 63/192,289, filed May 24, 2021.
"" U.S. Appl. No. 63/193,235, filed May 26, 2021.
"" U.S. Appl. No. 63/193,406, filed May 26, 2021.
"" U.S. Appl. No. 63/193,891, filed May 27, 2021.
"" U.S. Appl. No. 63/208,262, filed Jun. 8, 2021.
"" U.S. Appl. No. 63/214,551, filed Jun. 24, 2021.
"" U.S. Appl. No. 63/214,570, filed Jun. 24, 2021.
"" U.S. Appl. No. 63/215,017, filed Jun. 25, 2021.
"" U.S. Appl. No. 63/228,244, filed Aug. 2, 2021.
"" U.S. Appl. No. 63/228,252, filed Aug. 2, 2021.
"" U.S. Appl. No. 63/228,258, filed Aug. 2, 2021.
"" U.S. Appl. No. 63/230,894, filed Aug. 9, 2021.
"" U.S. Appl. No. 63/230,897, filed Aug. 9, 2021.
"" U.S. Appl. No. 63/238,457, filed Aug. 30, 2021.
"" U.S. Appl. No. 63/238,477, filed Aug. 30, 2021.
"" U.S. Appl. No. 63/241,328, filed Sep. 7, 2021.
"" U.S. Appl. No. 63/241,562, filed Sep. 8, 2021.
"" U.S. Appl. No. 63/241,564, filed Sep. 8, 2021.
"" U.S. Appl. No. 63/241,575, filed Sep. 8, 2021.
"" U.S. Appl. No. 63/246,972, filed Sep. 22, 2021.
"" U.S. Appl. No. 63/247,375, filed Sep. 23, 2021.
"" U.S. Appl. No. 63/247,478, filed Sep. 23, 2021.
"" U.S. Appl. No. 63/247,491, filed Sep. 23, 2021.
"" U.S. Appl. No. 63/299,208, filed Jan. 13, 2022.
"" U.S. Appl. No. 63/308,190, filed Feb. 9, 2022.

(56) References Cited

OTHER PUBLICATIONS

“” Defendant and Counterclaim Plaintiff Sage Products, LLC’s Answer, Defenses, and Counterclaims to Plaintiff’s Amended Complaint , Nov. 1, 2019.
“” *PureWick Corporation* v. *Sage Products, LLC* Transcripts vol. 2 , Mar. 29, 2022.
“” *PureWick Corporation* v. *Sage Products, LLC* Transcripts vol. 3 , Mar. 30, 2022.
“” *PureWick Corporation* v. *Sage Products, LLC* Transcripts vol. 4 , Mar. 31, 2022.
“” Memorandum Order , Feb. 2021.
“” Sage’s Initial Invalidity Contentions Regarding U.S. Pat. No. 8,287,508; U.S. Pat. No. 10,226,375; and U.S. Pat. No. 10,390,989 , May 29, 2020.
“” Sage’s Supplemental and Initial Invalidity Contentions Regarding U.S. Pat. No. 8,287,508; U.S. Pat. No. 10,226,375; U.S. Pat. No. 10,390,989 and Initial Invalidity Contentions Regarding U.S. Pat. No. 10,376,407 , Aug. 21, 2020.
“” Sage’s Second Supplemental Invalidity Contentions Regarding U.S. Pat. No. 8,287,508, U.S. Pat. No. 10,226,375, U.S. Pat. No. 10,390,989, and U.S. Pat. No. 10,376,407.
“” Boehringer CareDry System—Second Generation for Non-Invasive Urinary Management for Females , Mar. 2021.
“” *PureWick Corporation* v. *Sage Products, LLC* Transcripts vol. 5 , Apr. 1, 2022.
“” Excerpts from the 508 (U.S. Pat. No. 8,278,508) Patent’s Prosecution History , 2020.
“” *PureWick Corporation* v. *Sage Products, LLC* Transcripts vol. 1 , Mar. 28, 2022.
“” Plaintiff’s Opening Claim Construction Brief , Oct. 16, 2020.
“” Plaintiff’s Identification of Claim Terms and Proposed Constructions.
“” PureWick’s Response to Interrogatory No. 9 in *PureWick, LLC* v. *Sage Products, LLC* , Mar. 23, 2020.
“” Sage’s Preliminary Identification of Claim Elements and Proposed Constructions for U.S. Pat. No. 8,287,508, U.S. Pat. No. 10,226,376, U.S. Pat. No. 10,390,989 and U.S. Pat. No. 10,376,407.
“” Decision Granting Institution of Inter Partes Review for U.S. Pat. No. 8,287,508 , Feb. 17, 2021.
“” Corrected Certificate of Service , 2020.
“” Declaration of Diane K. Newman Curriculum Vitae , 2020.
“3 Devices Take Top Honors in Dare-To-Dream Medtech Design Contest” , R+D Digest , Nov. 2013 , 1 page.
“Advanced Mission Extender Device (AMDX) Products” , Omni Medical Systems, Inc. , 15 pages.
“AMXD Control Starter Kit” , Omni Medical Systems, Inc. , 1 page.
“AMXD Control Starter Kit Brochure” , https://www.omnimedicalsys.com/index.php?page=products , 8 pages.
“AMXDmax Advanced Mission Extender Device User & Maintenance Guide” , Omni Medical , Jan. 11, 2010 , 10 pages.
“AMXDmax Development History 2002-2014” , Omni Medical Systems, Inc. , 2 pages.
“AMXDmax In-Flight Bladder Relief”, Omni Medical; Omni Medical Systems, Inc. , 2015.
“AMXDX—Advanced Mission Extender Device Brochure” , Omni Medical , 2 pages.
“Combat Force Multiplier in Flight Bladder Relief Cockpit Essential Equipment Brochure” , Omni Medical , 20 pages.
“External Urine Management for Female Anatomy” , https://www.stryker.com/us/en/sage/products/sage-primafit.html , Jul. 2020 , 4 pages.
“GSA Price List” , Omni Medical , Apr. 2011 , 2 pages.
“High Absorbancy Cellulose Acetate Electrospun Nanofibers for Feminine Hygiene Application” , https://www.sciencedirect.com/science/article/abs/pii/S2352940716300701?via%3Dihub , Jul. 2016 , 3 pages.
“How is Polypropylene Fiber Made” , https:www.yarnsandfibers.com/textile-resources/synthetic-fibers/polypropylene-fiber/polypropylene-fiber-production-raw-materials/how-is-polypropylene-fiber-made/ last accessed 2020 , Oct. 7, 2020 , 3 pages.
“How Period Panties Work” , www.shethinx.com/pages/thinx-itworks , 2020 , 10 pages.
“Hydrogel properties of electrospun polyvinylpyrrolidone and polyvinylpyrrolidone/poly(acrylic acid) blend nanofibers” , https://pubs.rsc.org/en/content/articlelanding/2015/ra/c5ra07514a#!divAbstract , 2015 , 5 pages.
“In Flight Bladder Relief” , Omni Medical , 14 pages.
“Letter to Mark Harvie of Omni Measurement Systems” , Department of Veterans Affairs , Nov. 1, 2007 , 11 pages.
“Making Women’s Sanitary Products Safer and Cheaper” , https://www.elsevier.com/connect/making-womens-sanitary-products-safer-and-cheaper , Sep. 2016 , 10 pages.
“Novel Nanofibers Make Safe and Effective Absorbent for Sanitary Products” , https://www.materialstoday.com/nanomaterials/news/nanofibers-make-safe-and-effective-absorbent/ , Oct. 2016 , 3 pages.
“Research and Development Work Relating to Assistive Technology Jun. 2005” , British Department of Health , Nov. 2006 , 40 pages.
“Revised AMXDmax Advanced Mission Extender Device User & Maintenance Guide” , Omni Medical Systems , Oct. 8, 2019 , 52 pages.
“Rising Warrior Insulated Gallon Jug Cover” , https://www.amazon.com/Rising-Warrior-Insulated-Sleeve , 2021 , 2 pages.
“Step by Step How Ur24 WorksHome” , http://medicalpatentur24.com , Aug. 30, 2017 , 4 pages.
“Underwear that absorbs your period” , Thinx! , 7 pages.
“Urine Bag Cover-Catheter Bag Cover 2000 ml vol. Medline Style-Multiple Sclerosis-Spine Injury-Suprapublic Catheter-Bladder Incontinence” , https://www.etsy.com/listing/1142934658/urine-bag-cover-caatheter-bag-cover-2000 , 2022 , 1 page.
“User & Maintenance Guide” , Omni Medical , 2007 , 16 pages.
“Vinyl Dust Cover, Janome #741811000, Janome, Sewing Parts Online” , https://www.sewingpartsonline.com/vinyl-dust-cover-janome-74181000 , 2020 , 2 pages.
“Winners Announced for Dare-to-Dream Medtech Design Challenge” , https://www.mddionline.com/design-engineering/winners-announced-dare-dream-medtech-design-challenge , 2014 , 4 pages.
Ali , “Sustainability Assessment: Seventh Generation Diapers versus gDiapers” , The University of Vermont , Dec. 6, 2011 , pp. 1-31.
Autumn , et al. , “Frictional adhesion: a new angle on gecko attachment” , The Journal of Experimental Biology , 2006 , pp. 3569-3579.
Cañas , et al. , “Effect of nano- and micro-roughness on adhesion of bioinspired micropatterned surfaces” , Acta Biomaterialia 8 , 2012 , pp. 282-288.
Chaudhary , et al. , “Bioinspired dry adhesive: Poly(dimethylsiloxane) grafted with poly(2-ethylhexyl acrylate) brushes” , European Polymer Journal , 2015 , pp. 432-440.
Dai , et al. , “Non-sticky and Non-slippery Biomimetic Patterned Surfaces” , Journal of Bionic Engineering , Mar. 2020 , pp. 326-334.
Espinoza-Ramirez , “Nanobiodiversity and Biomimetic Adhesives Development: From Nature to Production and Application” , Journal of Biomaterials and Nanobiotechnology , pp. 78-101, 2019.
Hollister , “Female Urinary and Pouch and Male Urinary Pouch Brochure” , www.hollister.com , 2011 , 1 page.
Hollister , “Male Urinary Pouch External Collection Device” http://www.hollister.com/en/products/Continence-Care-Products/Urine-Collectors/Urine-Collection-Accessories/Male-Urinary-Pouch-External-Collection-Device.
Hollister , “Retracted Penis Pouch by Hollister” , Vitality Medical.com.
Hwang , et al. , “Multifunctional Smart Skin Adhesive Patches for Advanced Health Care” , Adv. Healthcare Mater , 2018 , pp. 1-20.
Jagota , et al. , “Adhesion, friction, and compliance of bio-mimetic and bio-inspired structured interfaces” , Materials Science and Engineering , 2011 , pp. 253-292.
Jeong , et al. , “A nontransferring dry adhesive with hierarchical polymer nanohairs” , PNAS , Apr. 7, 2009 , pp. 5639-5644.
Jeong , et al. , “Nanohairs and nanotubes: Efficient structural elements for gecko-inspired artificial dry adhesives”, Science Direct , 2009 , pp. 335-346.
Karp , et al. , “Dry solution to a sticky problem” , Nature. , 2011 , pp. 42-43.

(56) References Cited

OTHER PUBLICATIONS

Lee , et al. , "Continuous Fabrication of Wide-Tip Microstructures for Bio-Inspired Dry Adhesives via Tip Inking Process" , Journal of Chemistry , Jan. 2, 2019 , pp. 1-5.
Macaulay , et al. , "A Noninvasive Continence Management System: Development and Evaluation of a Novel Toileting Device for Women" , The Wound, Ostomy and Continence Nurses Society , 2007 , pp. 641-648.
Merriam-Webster Dictionary, , "Embed Definition & Meaning" , https://www.merriam-webster.com/dictionary/embed last accessed Aug. 3, 2023 , 2003.
Newman , et al. , "The Urinary Incontinence Sourcebook" , Petition for Interparties Review , 1997 , 23 pages.
Newton , et al. , "Measuring Safety, Effectiveness and Ease of Use of PureWick in the Management of Urinary Incontinence in Bedbound Women: Case Studies" , , 11 pages.
Parmar , "10 Finalists Chosen for Dare-to-Dream Medtech Design Challenge (PureWick)" , Design Services , Nov. 10, 2014 , 3 pages.
Parness , et al. , "A microfabricated wedge-shaped adhesive array displaying gecko-like dynamic adhesion, directionality" , J.R. Soc. Interface , 2009 , pp. 1223-1232.
Pieper , et al. , "An external urine-collection device for women: A clinical trial" , Journal of ER Nursing, vol. 20, No. 2 , Mar./Apr. 1993 , pp. 51-55.
Purewick , "Incontinence Relief for Women" , Presentation , Sep. 23, 2015 , 7 pages.
Pytlik , "Super Absorbent Polymers" , University of Buffalo.
Sachtman , "New Relief for Pilots? It Depends" , Wired , 2008 , 2 pages.
Tsipenyuk , et al. , "Use of biomimetic hexagonal surface texture in friction against lubricated skin" , Journal of The Royal Society—Interface , 2014 , pp. 1-6.
Vinas , "A Solution For An Awkward—But Serious—Subject" , http://www.aero-news.net/index.cfm?do=main.textpost&id=69ae2bb1-838b-4098-a7b5-7flbb2505688 last accessed Feb. 8, 2021.
Advisory Action for U.S. Appl. No. 16/433,773 mailed Dec. 29, 2023.
Advisory Action for U.S. Appl. No. 16/449,039 mailed Jan. 25, 2024.
Advisory Action for U.S. Appl. No. 16/452,258 mailed Apr. 8, 2024.
Advisory Action for U.S. Appl. No. 16/478,180 mailed Jun. 7, 2024.
Advisory Action for U.S. Appl. No. 16/904,868 mailed Jan. 2, 2024.
Advisory Action for U.S. Appl. No. 17/051,585 mailed Oct. 8, 2024.
Advisory Action for U.S. Appl. No. 17/179,116 mailed Jan. 8, 2024.
Advisory Action for U.S. Appl. No. 17/444,792 mailed Jul. 8, 2024.
Advisory Action for U.S. Appl. No. 17/446,256 mailed Dec. 8, 2023.
Advisory Action for U.S. Appl. No. 17/446,256 mailed Nov. 19, 2024.
Advisory Action for U.S. Appl. No. 17/446,654 mailed Apr. 15, 2024.
Advisory Action for U.S. Appl. No. 17/450,864 mailed Mar. 21, 2024.
Advisory Action for U.S. Appl. No. 17/451,345 mailed Jul. 3, 2024.
Advisory Action for U.S. Appl. No. 17/451,354 mailed Jan. 30, 2024.
Advisory Action for U.S. Appl. No. 17/453,260 mailed Dec. 22, 2023.
Advisory Action for U.S. Appl. No. 17/501,591 mailed Feb. 22, 2024.
Advisory Action for U.S. Appl. No. 17/597,673 mailed Jan. 7, 2025.
Advisory Action for U.S. Appl. No. 17/645,821 mailed Jul. 2, 2024.
Advisory Action for U.S. Appl. No. 17/646,771 mailed Feb. 29, 2024.
Advisory Action for U.S. Appl. No. 17/653,137 mailed Dec. 1, 2023.
Advisory Action for U.S. Appl. No. 17/653,137 mailed Nov. 20, 2024.
Advisory Action for U.S. Appl. No. 17/653,920 mailed Oct. 28, 2024.
Advisory Action for U.S. Appl. No. 17/655,464 mailed Dec. 13, 2023.
Advisory Action for U.S. Appl. No. 17/661,090 mailed Feb. 26, 2024.
Advisory Action for U.S. Appl. No. 17/663,330 mailed Feb. 27, 2024.
Advisory Action for U.S. Appl. No. 17/664,487 mailed Mar. 13, 2024.
Advisory Action for U.S. Appl. No. 17/808,354 mailed Jun. 12, 2024.
Advisory Action for U.S. Appl. No. 18/003,029 mailed Jan. 8, 2025.
Advisory Action for U.S. Appl. No. 18/134,857 mailed Oct. 23, 2024.
Advisory Action for U.S. Appl. No. 18/139,523 mailed Apr. 24, 2024.
Advisory Action for U.S. Appl. No. 18/140,163 mailed Jun. 3, 2024.
Advisory Action for U.S. Appl. No. 18/140,751 mailed Apr. 24, 2024.
Advisory Action for U.S. Appl. No. 18/164,800 mailed Feb. 12, 2024.
Advisory Action for U.S. Appl. No. 18/164,800 mailed Jan. 8, 2025.
Communication of Notice of Opposition of European Application No. 17807547.9 mailed Jan. 5, 2024.
Corrected Notice of Allowability for U.S. Appl. No. 16/369,676 mailed Dec. 7, 2023.
Corrected Notice of Allowability for U.S. Appl. No. 17/326,980 mailed Feb. 8, 2024.
Corrected Notice of Allowability for U.S. Appl. No. 17/450,864 mailed Oct. 24, 2024.
Corrected Notice of Allowability for U.S. Appl. No. 17/501,591 mailed Aug. 9, 2024.
Corrected Notice of Allowability for U.S. Appl. No. 17/646,771 mailed Jan. 17, 2025.
Corrected Notice of Allowability for U.S. Appl. No. 17/657,474 mailed Mar. 13, 2024.
Corrected Notice of Allowability for U.S. Appl. No. 17/657,474 mailed May 14, 2024.
Corrected Notice of Allowability for U.S. Appl. No. 17/664,914 mailed Aug. 9, 2024.
Corrected Notice of Allowability for U.S. Appl. No. 18/426,795 mailed Dec. 4, 2024.
Final Office Action for U.S. Appl. No. 16/433,773 mailed Sep. 9, 2024.
Final Office Action for U.S. Appl. No. 16/449,039 mailed Nov. 21, 2023.
Final Office Action for U.S. Appl. No. 16/452,258 mailed Dec. 21, 2023.
Final Office Action for U.S. Appl. No. 16/452,258 mailed Jan. 6, 2025.
Final Office Action for U.S. Appl. No. 16/478,180 mailed Feb. 28, 2024.
Final Office Action for U.S. Appl. No. 17/051,399 mailed Jan. 8, 2024.
Final Office Action for U.S. Appl. No. 17/051,585 mailed Jul. 5, 2024.
Final Office Action for U.S. Appl. No. 17/051,600 mailed Jun. 27, 2024.
Final Office Action for U.S. Appl. No. 17/444,792 mailed Apr. 3, 2024.
Final Office Action for U.S. Appl. No. 17/446,256 mailed Aug. 7, 2024.
Final Office Action for U.S. Appl. No. 17/446,654 mailed Dec. 18, 2024.
Final Office Action for U.S. Appl. No. 17/446,654 mailed Jan. 31, 2024.
Final Office Action for U.S. Appl. No. 17/447,123 mailed May 14, 2024.
Final Office Action for U.S. Appl. No. 17/450,864 mailed Dec. 28, 2023.
Final Office Action for U.S. Appl. No. 17/451,345 mailed Apr. 18, 2024.
Final Office Action for U.S. Appl. No. 17/451,354 mailed Oct. 28, 2024.

(56) References Cited

OTHER PUBLICATIONS

Final Office Action for U.S. Appl. No. 17/595,747 mailed Dec. 12, 2024.
Final Office Action for U.S. Appl. No. 17/597,673 mailed Oct. 22, 2024.
Final Office Action for U.S. Appl. No. 17/645,821 mailed Apr. 3, 2024.
Final Office Action for U.S. Appl. No. 17/646,771 mailed Dec. 21, 2023.
Final Office Action for U.S. Appl. No. 17/653,137 mailed Aug. 7, 2024.
Final Office Action for U.S. Appl. No. 17/653,920 mailed Aug. 14, 2024.
Final Office Action for U.S. Appl. No. 17/655,464 mailed Nov. 29, 2024.
Final Office Action for U.S. Appl. No. 17/661,090 mailed Dec. 11, 2023.
Final Office Action for U.S. Appl. No. 17/663,330 mailed Dec. 12, 2023.
Final Office Action for U.S. Appl. No. 17/664,487 mailed Jan. 13, 2025.
Final Office Action for U.S. Appl. No. 17/664,487 mailed Jan. 4, 2024.
Final Office Action for U.S. Appl. No. 17/808,354 mailed Apr. 10, 2024.
Final Office Action for U.S. Appl. No. 18/003,029 mailed Oct. 22, 2024.
Final Office Action for U.S. Appl. No. 18/134,857 mailed Jul. 25, 2024.
Final Office Action for U.S. Appl. No. 18/139,523 mailed Dec. 22, 2023.
Final Office Action for U.S. Appl. No. 18/140,163 mailed Mar. 27, 2024.
Final Office Action for U.S. Appl. No. 18/140,751 mailed Jan. 17, 2024.
Final Office Action for U.S. Appl. No. 18/164,800 mailed Dec. 6, 2023.
Final Office Action for U.S. Appl. No. 18/164,800 mailed Oct. 22, 2024.
International Search Report and Written Opinion from International Application No. PCT/US2023/024805 mailed Dec. 14, 2023.
International Search Report and Written Opinion from International Application No. PCT/US2023/025192 mailed Feb. 7, 2024.
International Search Report and Written Opinion from International Application No. PCT/US2023/025939 mailed Feb. 7, 2024.
International Search Report and Written Opinion from International Application No. PCT/US2023/030365 mailed Mar. 13, 2024.
International Search Report and Written Opinion from International Application No. PCT/US2023/030373 mailed Mar. 13, 2024.
International Search Report and Written Opinion from International Application No. PCT/US2023/031433 mailed Mar. 4, 2024.
International Search Report and Written Opinion from International Application No. PCT/US2023/031740 mailed Mar. 4, 2024.
International Search Report and Written Opinion from International Application No. PCT/US2023/036238 mailed Jul. 22, 2024.
International Search Report and Written Opinion from International Application No. PCT/US2023/036868 mailed Jun. 5, 2024.
International Search Report and Written Opinion from International Application No. PCT/US2023/075507 mailed Jun. 13, 2024.
International Search Report and Written Opinion from International Application No. PCT/US2023/077168 mailed Jun. 24, 2024.
International Search Report and Written Opinion from International Application No. PCT/US2023/077208 mailed May 10, 2024.
International Search Report and Written Opinion from International Application No. PCT/US2023/080680 mailed Jul. 22, 2024.
International Search Report and Written Opinion from International Application No. PCT/US2023/085516 mailed Aug. 26, 2024.
Issue Notification for U.S. Appl. No. 16/369,676 mailed Oct. 2, 2024.
Issue Notification for U.S. Appl. No. 16/449,039 mailed Jun. 19, 2024.
Issue Notification for U.S. Appl. No. 16/452,145 mailed Oct. 23, 2024.
Issue Notification for U.S. Appl. No. 17/051,550 mailed Mar. 13, 2024.
Issue Notification for U.S. Appl. No. 17/051,554 mailed Mar. 6, 2024.
Issue Notification for U.S. Appl. No. 17/179,116 mailed Dec. 25, 2024.
Issue Notification for U.S. Appl. No. 17/326,980 mailed Jul. 10, 2024.
Issue Notification for U.S. Appl. No. 17/447,123 mailed Nov. 13, 2024.
Issue Notification for U.S. Appl. No. 17/448,811 mailed Jul. 3, 2024.
Issue Notification for U.S. Appl. No. 17/450,864 mailed Jan. 8, 2025.
Issue Notification for U.S. Appl. No. 17/453,260 mailed Jul. 10, 2024.
Issue Notification for U.S. Appl. No. 17/453,560 mailed Aug. 7, 2024.
Issue Notification for U.S. Appl. No. 17/657,474 mailed Jun. 19, 2024.
Issue Notification for U.S. Appl. No. 17/662,700 mailed Oct. 23, 2024.
Issue Notification for U.S. Appl. No. 17/663,046 mailed Dec. 20, 2023.
Issue Notification for U.S. Appl. No. 17/664,914 mailed Nov. 6, 2024.
Issue Notification for U.S. Appl. No. 17/667,097 mailed Dec. 11, 2024.
Issue Notification for U.S. Appl. No. 18/140,163 mailed Dec. 4, 2024.
Issue Notification for U.S. Appl. No. 18/198,464 mailed Nov. 20, 2024.
Issue Notification for U.S. Appl. No. 18/299,788 mailed Feb. 21, 2024.
Issue Notification for U.S. Appl. No. 18/389,009 mailed Dec. 18, 2024.
Non-Final Office Action for U.S. Appl. No. 16/369,676 mailed Feb. 29, 2024.
Non-Final Office Action for U.S. Appl. No. 16/433,773 mailed Feb. 26, 2024.
Non-Final Office Action for U.S. Appl. No. 16/452,258 mailed Jun. 20, 2024.
Non-Final Office Action for U.S. Appl. No. 16/478,180 mailed Aug. 7, 2024.
Non-Final Office Action for U.S. Appl. No. 16/904,868 mailed Mar. 12, 2024.
Non-Final Office Action for U.S. Appl. No. 17/051,585 mailed Jan. 8, 2024.
Non-Final Office Action for U.S. Appl. No. 17/051,600 mailed Jan. 17, 2024.
Non-Final Office Action for U.S. Appl. No. 17/179,116 mailed Feb. 26, 2024.
Non-Final Office Action for U.S. Appl. No. 17/378,015 mailed Jul. 5, 2024.
Non-Final Office Action for U.S. Appl. No. 17/444,792 mailed Oct. 30, 2024.
Non-Final Office Action for U.S. Appl. No. 17/446,256 mailed Dec. 13, 2024.
Non-Final Office Action for U.S. Appl. No. 17/446,256 mailed Feb. 13, 2024.
Non-Final Office Action for U.S. Appl. No. 17/446,654 mailed Jun. 25, 2024.
Non-Final Office Action for U.S. Appl. No. 17/447,123 mailed Jan. 24, 2024.
Non-Final Office Action for U.S. Appl. No. 17/448,811 mailed Jan. 17, 2024.
Non-Final Office Action for U.S. Appl. No. 17/450,864 mailed May 29, 2024.

(56) References Cited

OTHER PUBLICATIONS

Non-Final Office Action for U.S. Appl. No. 17/451,345 mailed Jan. 17, 2024.
Non-Final Office Action for U.S. Appl. No. 17/451,345 mailed Jul. 25, 2024.
Non-Final Office Action for U.S. Appl. No. 17/451,354 mailed Apr. 4, 2024.
Non-Final Office Action for U.S. Appl. No. 17/595,747 mailed Jun. 7, 2024.
Non-Final Office Action for U.S. Appl. No. 17/597,408 mailed Aug. 15, 2024.
Non-Final Office Action for U.S. Appl. No. 17/597,673 mailed Mar. 20, 2024.
Non-Final Office Action for U.S. Appl. No. 17/614,173 mailed Sep. 24, 2024.
Non-Final Office Action for U.S. Appl. No. 17/625,941 mailed Nov. 4, 2024.
Non-Final Office Action for U.S. Appl. No. 17/628,411 mailed Sep. 23, 2024.
Non-Final Office Action for U.S. Appl. No. 17/645,821 mailed Sep. 6, 2024.
Non-Final Office Action for U.S. Appl. No. 17/646,771 mailed Apr. 24, 2024.
Non-Final Office Action for U.S. Appl. No. 17/653,137 mailed Jan. 18, 2024.
Non-Final Office Action for U.S. Appl. No. 17/653,314 mailed Aug. 29, 2024.
Non-Final Office Action for U.S. Appl. No. 17/653,920 mailed Mar. 15, 2024.
Non-Final Office Action for U.S. Appl. No. 17/653,920 mailed Nov. 27, 2024.
Non-Final Office Action for U.S. Appl. No. 17/655,464 mailed Mar. 26, 2024.
Non-Final Office Action for U.S. Appl. No. 17/661,090 mailed May 22, 2024.
Non-Final Office Action for U.S. Appl. No. 17/663,330 mailed Jul. 1, 2024.
Non-Final Office Action for U.S. Appl. No. 17/664,487 mailed Jun. 17, 2024.
Non-Final Office Action for U.S. Appl. No. 17/664,914 mailed Jan. 31, 2024.
Non-Final Office Action for U.S. Appl. No. 17/749,340 mailed Aug. 14, 2024.
Non-Final Office Action for U.S. Appl. No. 17/757,311 mailed Oct. 22, 2024.
Non-Final Office Action for U.S. Appl. No. 17/758,316 mailed Aug. 28, 2024.
Non-Final Office Action for U.S. Appl. No. 17/759,697 mailed Dec. 4, 2024.
Non-Final Office Action for U.S. Appl. No. 17/808,354 mailed Dec. 13, 2024.
Non-Final Office Action for U.S. Appl. No. 17/808,354 mailed Nov. 28, 2023.
Non-Final Office Action for U.S. Appl. No. 17/907,125 mailed Dec. 13, 2024.
Non-Final Office Action for U.S. Appl. No. 18/003,029 mailed Mar. 26, 2024.
Non-Final Office Action for U.S. Appl. No. 18/134,857 mailed Jan. 25, 2024.
Non-Final Office Action for U.S. Appl. No. 18/139,523 mailed Aug. 26, 2024.
Non-Final Office Action for U.S. Appl. No. 18/140,751 mailed Jun. 21, 2024.
Non-Final Office Action for U.S. Appl. No. 18/164,800 mailed Mar. 22, 2024.
Non-Final Office Action for U.S. Appl. No. 18/198,464 mailed Dec. 7, 2023.
Non-Final Office Action for U.S. Appl. No. 18/389,009 mailed May 24, 2024.
Non-Final Office Action for U.S. Appl. No. 18/426,795 mailed Aug. 9, 2024.
Non-Final Office Action for U.S. Appl. No. 18/451,080 mailed Jul. 30, 2024.
Non-Final Office Action for U.S. Appl. No. 18/584,002 mailed Sep. 19, 2024.
Notice of Allowance for U.S. Appl. No. 16/369,676 mailed Jun. 17, 2024.
Notice of Allowance for U.S. Appl. No. 16/449,039 mailed Mar. 28, 2024.
Notice of Allowance for U.S. Appl. No. 16/452,145 mailed Jul. 11, 2024.
Notice of Allowance for U.S. Appl. No. 16/478,180 mailed Dec. 16, 2024.
Notice of Allowance for U.S. Appl. No. 16/904,868 mailed Jan. 21, 2025.
Notice of Allowance for U.S. Appl. No. 16/904,868 mailed Sep. 29, 2024.
Notice of Allowance for U.S. Appl. No. 17/051,550 mailed Feb. 7, 2024.
Notice of Allowance for U.S. Appl. No. 17/051,585 mailed Dec. 26, 2024.
Notice of Allowance for U.S. Appl. No. 17/179,116 mailed Sep. 13, 2024.
Notice of Allowance for U.S. Appl. No. 17/326,980 mailed Apr. 5, 2024.
Notice of Allowance for U.S. Appl. No. 17/326,980 mailed Jan. 29, 2024.
Notice of Allowance for U.S. Appl. No. 17/447,123 mailed Jul. 26, 2024.
Notice of Allowance for U.S. Appl. No. 17/448,811 mailed Jun. 14, 2024.
Notice of Allowance for U.S. Appl. No. 17/450,864 mailed Sep. 18, 2024.
Notice of Allowance for U.S. Appl. No. 17/453,260 mailed Apr. 8, 2024.
Notice of Allowance for U.S. Appl. No. 17/453,560 mailed Jan. 31, 2024.
Notice of Allowance for U.S. Appl. No. 17/501,591 mailed Jul. 31, 2024.
Notice of Allowance for U.S. Appl. No. 17/501,591 mailed Nov. 20, 2024.
Notice of Allowance for U.S. Appl. No. 17/527,769 mailed Nov. 20, 2024.
Notice of Allowance for U.S. Appl. No. 17/646,771 mailed Dec. 17, 2024.
Notice of Allowance for U.S. Appl. No. 17/657,474 mailed Mar. 5, 2024.
Notice of Allowance for U.S. Appl. No. 17/657,474 mailed May 2, 2024.
Notice of Allowance for U.S. Appl. No. 17/661,090 mailed Oct. 30, 2024.
Notice of Allowance for U.S. Appl. No. 17/662,700 mailed Jun. 12, 2024.
Notice of Allowance for U.S. Appl. No. 17/662,700 mailed Mar. 6, 2024.
Notice of Allowance for U.S. Appl. No. 17/663,330 mailed Nov. 20, 2024.
Notice of Allowance for U.S. Appl. No. 17/664,914 mailed Jul. 26, 2024.
Notice of Allowance for U.S. Appl. No. 17/667,097 mailed Aug. 28, 2024.
Notice of Allowance for U.S. Appl. No. 18/140,163 mailed Aug. 21, 2024.
Notice of Allowance for U.S. Appl. No. 18/140,751 mailed Nov. 1, 2024.
Notice of Allowance for U.S. Appl. No. 18/198,464 mailed Apr. 17, 2024.
Notice of Allowance for U.S. Appl. No. 18/198,464 mailed Jul. 30, 2024.
Notice of Allowance for U.S. Appl. No. 18/389,009 mailed Aug. 28, 2024.

(56) References Cited

OTHER PUBLICATIONS

Notice of Allowance for U.S. Appl. No. 18/415,080 mailed Dec. 30, 2024.
Notice of Allowance for U.S. Appl. No. 18/426,795 mailed Nov. 20, 2024.
Notice of Allowance for U.S. Appl. No. 18/584,002 mailed Jan. 8, 2025.
Restriction Requirement for U.S. Appl. No. 17/527,769 mailed Jun. 17, 2024.
Restriction Requirement for U.S. Appl. No. 17/596,629 mailed Sep. 19, 2024.
Restriction Requirement for U.S. Appl. No. 17/625,941 mailed Aug. 7, 2024.
Restriction Requirement for U.S. Appl. No. 17/667,097 mailed Mar. 20, 2024.
Restriction Requirement for U.S. Appl. No. 17/754,736 mailed Nov. 20, 2024.
Restriction Requirement for U.S. Appl. No. 17/756,201 mailed Oct. 4, 2024.
Restriction Requirement for U.S. Appl. No. 17/758,152 mailed Nov. 5, 2024.
Restriction Requirement for U.S. Appl. No. 17/809,083 mailed Dec. 31, 2024.
Restriction Requirement for U.S. Appl. No. 17/878,268 mailed Sep. 20, 2024.
Submission in Opposition Proceedings for European Application No. 17807547.9 filed Jan. 10, 2024.
Supplemental Notice of Allowance for U.S. Appl. No. 17/051,550 mailed Feb. 21, 2024.
Supplemental Notice of Allowance for U.S. Appl. No. 17/051,554 mailed Feb. 14, 2024.
U.S. Appl. No. 17/013,822, filed Sep. 7, 2020.
U.S. Appl. No. 17/444,792, filed Aug. 10, 2021.
U.S. Appl. No. 18/249,577, filed Oct. 19, 2021.
U.S. Appl. No. 18/294,370, filed Feb. 1, 2024.
U.S. Appl. No. 18/294,403, filed Feb. 1, 2024.
U.S. Appl. No. 18/415,080, filed Jan. 17, 2024.
U.S. Appl. No. 18/426,795, filed Jan. 30, 2024.
U.S. Appl. No. 18/563,672, filed Nov. 22, 2023.
U.S. Appl. No. 18/569,711, filed Dec. 13, 2023.
U.S. Appl. No. 18/569,778, filed Dec. 13, 2023.
U.S. Appl. No. 18/584,002, filed Feb. 22, 2024.
U.S. Appl. No. 18/610,523, filed Mar. 20, 2024.
U.S. Appl. No. 18/662,216, filed May 13, 2024.
U.S. Appl. No. 18/681,987, filed Feb. 7, 2024.
U.S. Appl. No. 18/682,006, filed Feb. 7, 2024.
U.S. Appl. No. 18/687,117, filed Feb. 27, 2024.
U.S. Appl. No. 18/688,023, filed Feb. 29, 2024.
U.S. Appl. No. 18/693,638, filed Mar. 20, 2024.
U.S. Appl. No. 18/694,090, filed Mar. 21, 2024.
U.S. Appl. No. 18/728,604, filed Jul. 12, 2024.
U.S. Appl. No. 18/757,964, filed Jun. 28, 2024.
U.S. Appl. No. 18/758,025, filed Jun. 28, 2024.
U.S. Appl. No. 18/828,559, filed Sep. 9, 2024.
U.S. Appl. No. 18/834,115, filed Jul. 29, 2024.
U.S. Appl. No. 18/834,176, filed Jul. 29, 2024.
U.S. Appl. No. 18/834,340, filed Jul. 30, 2024.
U.S. Appl. No. 18/835,068, filed Aug. 1, 2024.
U.S. Appl. No. 18/835,444, filed Aug. 2, 2024.
U.S. Appl. No. 18/836,204, filed Aug. 6, 2024.
U.S. Appl. No. 18/841,630, filed Aug. 26, 2024.
U.S. Appl. No. 18/851,197, filed Sep. 26, 2024.
U.S. Appl. No. 18/886,306, filed Sep. 16, 2024.
U.S. Appl. No. 18/903,592, filed Oct. 1, 2024.
U.S. Appl. No. 18/925,921, filed Oct. 24, 2024.
U.S. Appl. No. 18/930,014, filed Oct. 29, 2024.
U.S. Appl. No. 18/931,853, filed Oct. 30, 2024.
U.S. Appl. No. 18/951,944, filed Nov. 19, 2024.
U.S. Appl. No. 18/957,011, filed Nov. 22, 2024.
U.S. Appl. No. 18/974,367, filed Dec. 9, 2024.
U.S. Appl. No. 18/982,930, filed Dec. 16, 2024.
U.S. Appl. No. 63,564,696, filed Mar. 13, 2024.
U.S. Appl. No. 63/181,709, filed Apr. 29, 2021.
U.S. Appl. No. 63/561,893, filed Dec. 11, 2023.
U.S. Appl. No. 63/568,615, filed Mar. 22, 2024.
U.S. Appl. No. 63/608,553, filed Dec. 11, 2023.
U.S. Appl. No. 63/683,428, filed Aug. 15, 2024.
U.S. Appl. No. 63/711,438, filed Oct. 24, 2024.
U.S. Appl. No. 63/711,445, filed Oct. 24, 2024.
U.S. Appl. No. 63/720,004, filed Nov. 13, 2024.
"Dictionary.com, Abut Definition and Meaning", Dictionary.com, https://www.dictionary.com/browse/abut, 2024, 1 page.
"Oblong", Cambridge Dictionary, https://dictionary.cambridge.org/dictionary/english/oblong, 2024, 1 page.
Britannica, "Polyolefin", Britannica Online Encyclopedia, T. Editors of Encyclopaedia, https://www.britannica.com/science/polyolefin, Jul. 26, 2012.
Martin, "Chapter 5 Applications of Polyethylene Oxide (POLYOX) in Hydrophilic Matrices", Hydrophilic Matrix Tablets for Oral Controlled Release, AAPS Advances in the Pharmaceutical Sciences vol. 16, 2014, pp. 123-141.
Wikipedia article, "Decibel", https://web.archive.org/web/20200415211917/https://en.wikipedia/org/wiki/Decibel last accessed Mar. 11, 2024, 21 pages.
Wikipedia article, "Fiberglass" https://web.archive.org.web/20200309194847/https://en.wikipedia.org/wiki/Fiberglass last accessed Mar. 11, 2024.
Wikipedia article, "Zylinder (Geometrie)", https://de.wikipedia.org/w/index.php?title=Zylinder(Geometrie)&oldid=154862081, version of Jun. 1, 2016, 7 pages.

* cited by examiner

URINE COLLECTION CONTAINER BAFFLE STRUCTURES, AND RELATED SYSTEMS AND METHODS

CROSS-REFERENCE TO RELATED APPLICATIONS

This application is a U.S. national phase of International Application No. PCT/US2022/030685 filed May 24, 2022, which claims priority to U.S. Provisional Patent Application No. 63/193,235 filed on May 26, 2021, the disclosure of each of which is incorporated herein, in its entirety, by this reference.

BACKGROUND

An individual may have limited or impaired mobility such that typical urination processes are challenging or impossible. For example, the individual may have surgery or a disability that impairs mobility. In another example, the individual may have restricted travel conditions such as those experienced by pilots, drivers, and workers in hazardous areas. Additionally, fluid collection from the individual may be needed for monitoring purposes or clinical testing.

Bed pans and urinary catheters, such as a Foley catheter, may be used to address some of these circumstances. However, bed pans and urinary catheters have several problems associated therewith. For example, bed pans may be prone to discomfort, spills, and other hygiene issues. Urinary catheters be may be uncomfortable, painful, and may cause urinary tract infections. Conventional urine collection devices also may be limited to use when a patient is confined to a bed in a supine position.

Thus, users and manufacturers of fluid collection devices continue to seek new and improved devices, systems, and methods to collect urine.

SUMMARY

Embodiments disclosed herein are related to urine collection container baffle structures, and related systems and methods. In an embodiment, a urine collection system includes a urine collection device, a conduit, a canister, and a baffle structure. The urine collection device is configured to be positioned at least proximate to a urethra of a user. The conduit is in fluid communication with the urine collection device. The canister includes an interior region, and the baffle structure is positioned or positionable in the interior region of the canister.

In an embodiment, a urine collection container includes a canister, a baffle structure, and a lid. The canister has an interior region and the baffle structure is positioned or positionable in the interior region of the canister. The lid is secured or securable to the canister and includes a collection port and a vacuum port.

In an embodiment, a method of collecting fluid includes positioning a baffle structure in an interior region of a canister. The method also includes positioning a fluid collection device at least proximate to a urethra of a user, the urine collection device being in fluid communication with the canister through a conduit. The method also includes collecting urine discharged by the user in the urine collection device. The method also includes drawing urine from the urine collection device through the conduit into the interior region of the canister, the urine contacting at least a portion of the baffle structure in the interior region of the canister.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Embodiments disclosed herein are related to urine collection containers and systems including baffle structures, and related methods. The devices and systems disclosed herein are configured to collect fluids from an individual. The fluids collected by the fluid collection devices may include at least one of urine, vaginal discharge, penile discharge, reproductive fluids, blood, sweat, or other bodily fluids.

In conventional urine collection systems, the sound of urine splashing during urine collection and/or canister movement is often embarrassing for users. For example, the urine may enter at the top of a canister and fall to the bottom of the canister or the urine level in the canister, increasing the splashing noise as the falling urine increases speed before contacting the bottom of the container or the urine level. The splashing noise may draw attention to the urine collection system during urine collection and/or movement by the user. Users of urine collection systems may have concerns about discretion when using urine collection systems, especially when the urine collection systems are used in ambulatory settings or other settings outside of a clinical setting. For example, some users may use a urine collection system while sitting in a wheelchair, with the urine collection canister positioned on a support on the wheelchair. As the wheelchair moves, the urine in the canister may create an embarrassing splashing noise, preventing the discretion desired by the user.

To improve conventional urine collection systems, baffle structures described herein are positioned or positionable in the canister of a urine collection systems. In at least one, some, or all embodiments of urine collection systems described herein, the baffle structure may be inserted into the canister to act as a baffling system that results in the technical effect of preventing the urine (or other fluids) from falling a longer distance and splashing in the canister, thereby preventing or inhibiting the distinct splashing noise common to conventional urine collection systems. The baffle structure may instead guide the urine through the baffle structure to the bottom of the canister and/or the urine level in the canister.

Figure 1A:
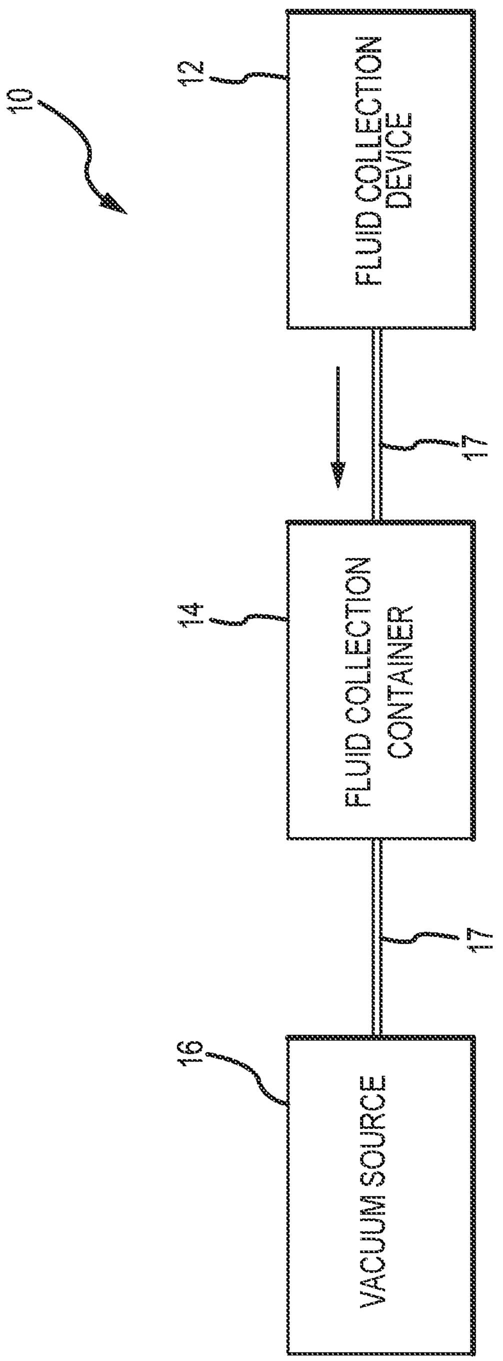
FIG. 1A is a block diagram of a portable fluid collection system, according to an embodiment.

FIG. 1A is a block diagram of a fluid collection system 10, according to an embodiment. The fluid collection system 10 may be included in embodiments of fluid collection systems described herein. The system 10 includes a fluid (e.g., urine) collection device 12 (e.g., any of the fluid collection devices disclosed herein), a fluid (e.g., urine) collection container 14, and a vacuum source 16 (e.g., pump). The fluid collection device 12, the fluid collection container 14, and the vacuum source 16 may be fluidly coupled to each other via one or more conduits 17. For example, fluid collection device 12 may be operably coupled to one or more of the fluid collection container 14 or the vacuum source 16 via the conduit 17. In some embodiments, the vacuum source 16 may be secured directly to the fluid collection container 14. Fluid (e.g., urine or other bodily fluids) collected in the fluid collection device 12 may be removed from the fluid collection device 12 via the conduit 17 secured to the fluid collection device 12. Suction force may be introduced into the chamber of the fluid collection device 12 via the inlet of the conduit 17 responsive to suction (e.g., vacuum) force applied at the outlet of the conduit 17.

The suction force may be applied to the outlet of the conduit 17 by the vacuum source 16 either directly or indirectly. The suction force may be applied indirectly via the fluid collection container 14. For example, the outlet of the conduit 17 may be disposed within or fluidly coupled to an interior region of the fluid collection container 14 and an additional conduit 17 may extend from the fluid collection container 14 to the vacuum source 16. Accordingly, the vacuum source 16 may apply suction to the fluid collection device 12 via the fluid collection container 14. The suction force may be applied directly via the vacuum source 16. For example, the outlet of the conduit 17 may be disposed within the vacuum source 16. An additional conduit 17 may extend from the vacuum source 16 to a point outside of the fluid collection device 12, such as to the fluid collection container 14. In such examples, the vacuum source 16 may be disposed between the fluid collection device 12 and the fluid collection container 14.

The fluid collection container 14 is sized and shaped to retain a fluid therein. The fluid collection container 14 may include a bag (e.g., drainage bag), a bottle, a canister, or a cup (e.g., collection jar), or any other enclosed container for storing bodily fluid(s) such as urine. In some examples, the conduit 17 may extend from the fluid collection device 12 and attach to the fluid collection container 14 at a first point therein. An additional conduit 17 may attach to the fluid collection container 14 at a second point thereon and may extend and attach to the vacuum source 16. Accordingly, a vacuum (e.g., suction) may be drawn through fluid collection device 12 via the fluid collection container 14. Fluid, such as urine, may be drained from the fluid collection device 12 using the vacuum source 16.

The vacuum source 16 may include one or more of a manual vacuum pump, and electric vacuum pump, a diaphragm pump, a centrifugal pump, a displacement pump, a magnetically driven pump, a peristaltic pump, or any source configured to produce a vacuum (e.g., negative pressure). The vacuum source 16 may provide a vacuum or suction to remove fluid from the fluid collection device 12. In some examples, the vacuum source 16 may be powered by one or more of a power cord (e.g., connected to a power socket), one or more batteries, or even manual power (e.g., a hand operated vacuum pump). In some examples, the vacuum source 16 may be sized and shaped to fit outside of, on, or within the fluid collection device 12. For example, the vacuum source 16 may include one or more miniaturized pumps or one or more micro pumps. The vacuum sources disclosed herein may include one or more of a switch, a button, a plug, a remote, or any other device suitable to activate the vacuum source 16.

Figure 1B:
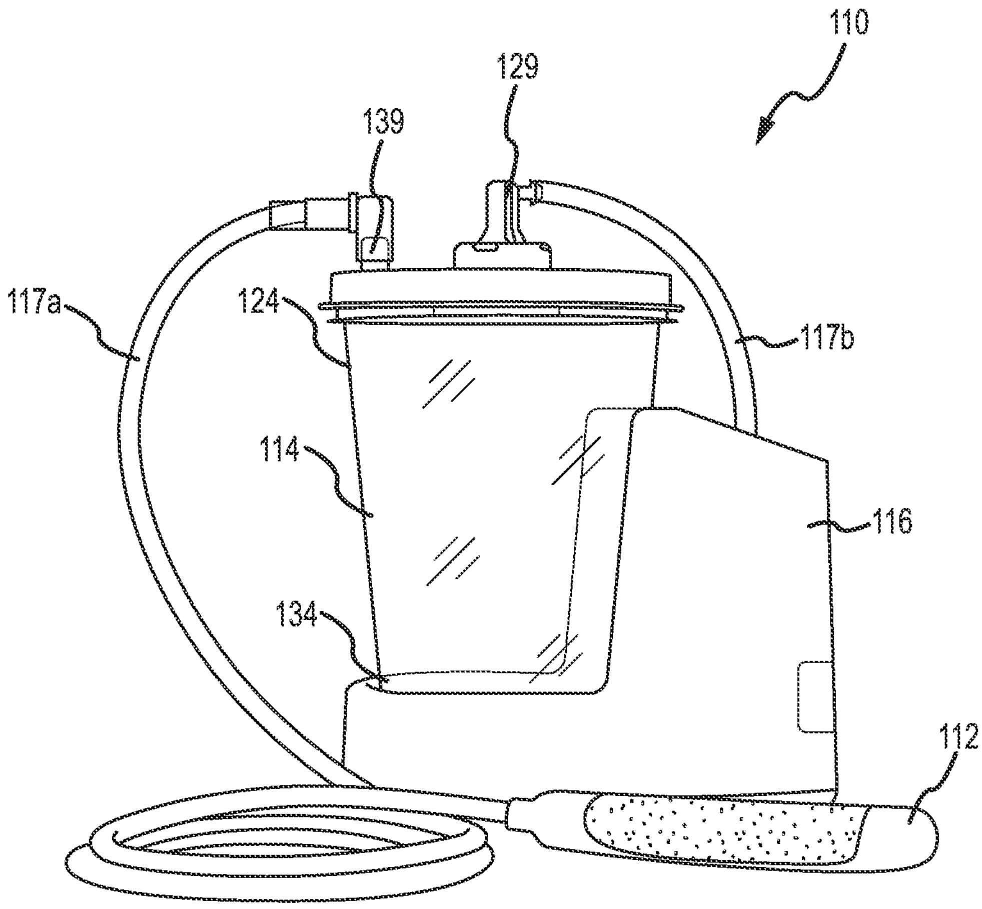
FIG. 1B is a front view of a urine collection system, according to an embodiment.

FIG. 1B shows an example of a urine collection system 100, according to an embodiment. The urine collection system 100 may include a urine collection device 112, a first conduit 117*a* in fluid communication with an interior region of the urine collection device 112, a urine collection container, and a pump 116. The urine collection container may include a canister 114 and a lid 119 secured or securable to the canister 114. The canister 114 may include a top region 124 and a bottom region 134, and may at least partially define an interior region in fluid communication with the internal region of the urine collection device 112 via the first conduit 117*a*. For example, the lid 119 may include a urine port 139 to which the first conduit 117*a* may be detachably secured to provide fluid communication between urine collection device 112 and the interior region of the canister 114. A second conduit 117*b* may provide fluid communication between the interior region of the canister 114 and the pump 116. For example, the lid 119 may include a vacuum port 129 to which the second conduit 117*b* may be detachably secured to provide fluid communication between the pump 116 and the interior region of the canister. The vacuum port 129 and/or the urine port 139 may include an adapter detachably secured thereto to secure the respective conduit 117*b*, 117*a* to the vacuum port 129 and/or the urine port 139. In some embodiments, at least one (e.g., both) of the first conduit 117*a* and the second conduit 117*b* may be detachably connected or secured to the canister 114 effective to provide fluid communication with the interior region of the canister 114. For example, the canister may include at least one (e.g. both) of the urine port 139 and the vacuum port 129.

The urine collection device 112 may be configured to be positioned at least proximate to a urethra of a user. While the urine collection device 112 shown in FIG. 1B includes a female urine collection device, the urine collection device 112 may instead include a male urine collection device. PCT International Application No. PCT/US2019/029616, for example, describes various embodiments of both male and female fluid collection devices, the disclosure of which are incorporated in their entirety by this reference. Moreover, the urine collection device 112 may be interchangeable in the urine collection system 100 between different types, varieties, and sizes of male or female urine collection devices or other bodily fluid collection devices. Generally, the urine collection device 112 may include a surface sized to be positioned proximate or adjacent to the urethra and configured to wick urine or other fluids away from the user. Urine or other fluids may be wicked from the surface to a reservoir in the urine collection device 112.

The urine collection system 100 also includes the first conduit 117*a* in fluid communication with an interior region (e.g. reservoir) of the urine collection device 112 and the interior region of the canister 114. The first conduit 117*a* may be positioned or positionable between the urine collection device 112 and the canister 114. The urine collection system 100 also may include the second conduit 117*b* providing fluid communication between the pump 116 and the interior region of the canister 114. In some embodiments, the pump 116 may be secured directly to the canister 114, and the second conduit 117*b* may be absent from the urine collection system 100. The conduits 117*a*, 117*b* may include a flexible tube. In some embodiments, at least a portion of the first conduit 117*a* is substantially opaque, thereby inhibiting viewing of the urine within the first conduit 117*a*.

The canister 114 may be reusable and dishwasher safe, and may include a generally rigid material such as polycarbonate or glass. In some embodiments, the canister 114 may be disposable. The urine collection system 100 may be configured to accommodate different volumetric sizes of canisters 114. The canister 114 may be substantially cylindrical or frustoconical. In some embodiments, the canister may include other shapes and configurations, such as a generally square or rectangular side profile. In some embodiments, the lid 119 having multiple ports 129, 139 and/or adapters for attachment of the conduits 117*a*, 117*b* thereto may be secured or securable to the canister 114. In some embodiments, the lid 119 may include additional ports or adapters than those shown in FIG. 1B. Except for the ports and/or adapters for attachment of the conduits 117*a*, 117*b*, the canister 114 may be sealed and airtight such that the urine collected in the canister 114 does not leak or spill.

The pump 116 is in fluid communication with the interior region of the canister 114 and is configured to pull a vacuum on the interior region of the canister 114 effective to draw the urine from the urine collection device 112 through the first conduit 117*a* into the canister 114. The pump 116 may be secured directly to the canister 114, or the conduit 117*b* may fluidly couple the pump 116 with the interior region of the canister 114. The pump 116 may include one or more of a manual vacuum pump, and electric vacuum pump, a diaphragm pump, a centrifugal pump, a displacement pump, a magnetically driven pump, a peristaltic pump, or any pump configured to produce a vacuum. The pump 116 may provide a vacuum or suction to remove fluid from the fluid collection device 112. In some examples, the pump 116 may be powered by one or more batteries or other power sources. The pump 116 may be included in a housing that also supports the canister 114. In some examples, the pump 116 may be sized and shaped to fit within a container support on a wheelchair. In some embodiments, the pump 116 may include a wall-mounted pump. The pump 116 may include one or more of a switch, a button, a plug, a remote, or any other device suitable to activate the pump 116.

The urine collection system 100 may include a baffle structure positioned or positionable in the interior region of the canister 114. In at least one, some or all embodiments of baffle structures described herein, the configuration of the baffle structure results in the technical effect of improving discretion during urine collection and/or filling of the canister. For example, in contrast to conventional urine collection systems, at least one, some, or all embodiments of baffle structures described herein prevent urine or other fluid from splashing into the canister 114 as the urine is drawn from the user and dispensed into the canister 114. In conventional systems, urine splashing into the canister draws attention to the urine collection system due to the noise generated by the urine splashing in the container during and after filling of the container. In urine collection systems designed for ambulatory patients, noise from urine splashing during collection and movement is increased and/or causes additional embarrassment for users.

To improve the urine collection system 100, a baffle structure may be positioned or positionable in the interior region of the canister. The baffle structure may reduce the distance urine freefalls as the urine enters the canister 114, thereby inhibiting amplification of the splashing noise. To reduce the distance the urine freefalls in the canister 114, the baffle structure may guide the urine the bottom region 134 of the canister 114 (or the current urine level in the canister 114) to prevent or minimize the splashing noise in the canister. Many embodiments of baffle structures described herein may be removable from the canister 114 and reusable in a different canister 114. In some embodiments, the baffle structures may be integrally formed (e.g., molded) with the canister 114.

Figure 2A:
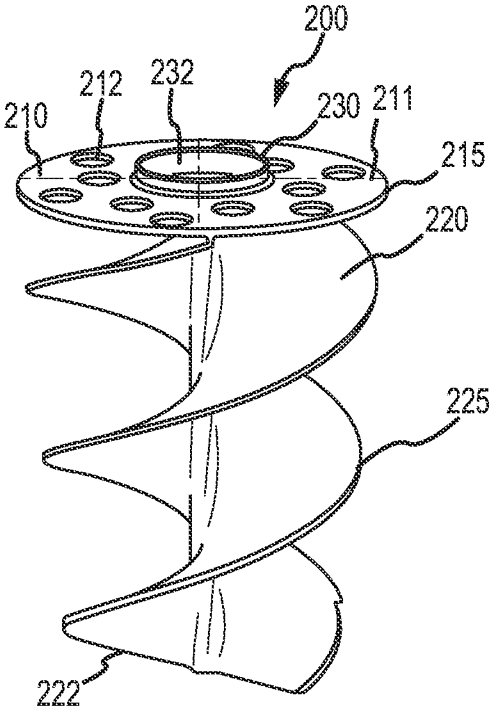
FIG. 2A is a side isometric view of a spiral baffle structure for a urine collection system, according to an embodiment.
Figure 2B:
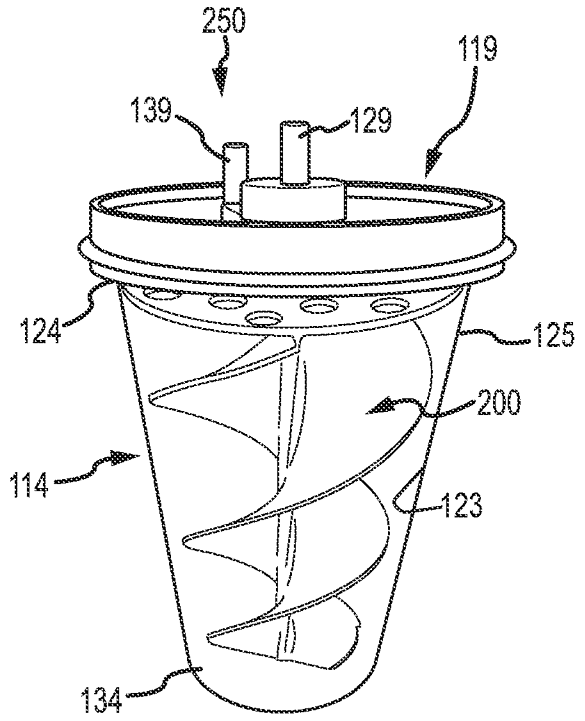
FIG. 2B is a side isometric view of a urine collection container including a canister, a lid, and the spiral baffle structure of FIG. 2A positioned in a urine collection container, according to an embodiment.

FIG. 2A is an isometric side view of a spiral baffle structure 200 and FIG. 2B is an isometric view of a urine collection container 250 including the lid 119 secured to the top region 124 of the canister 114 and the baffle structure 200 positioned in the interior region of the canister 114, according to an embodiment. The baffle structure 200 may include one or more baffles. For example, the one or more baffles of the baffle structure 200 may include at least one plate 210 having or defining a plurality of holes 212 extending therethrough and a helical body 220 secured to the plate 210. When the baffle structure 200 is positioned in the canister 114, the helical body 220 extends from the bottom region 134 at least partially towards the top region 124 of the canister 114 and the plate 210 is positioned proximate the top region 124 of the canister 114. In some embodiments, a distal end 222 of the helical body 220 opposite to the plate 210 may rest on the bottom of the canister 114.

In some embodiments, the canister 114 includes one or more sidewalls 125 having an inner perimeter 123 at least partially defining the interior region of the canister 114. The plate 210 may include an outer periphery 215 generally complementary to the inner perimeter 123 of the one or more sidewalls 125 at the top region 124 of the canister 114. The plate 210 may be sized such that the outer periphery 215 interfaces or is adjacent to the inner perimeter 123, or is spaced from the inner perimeter 123 of the canister 114. In some embodiments, the helical body 220 includes an outer periphery 225 generally complementary to the inner perimeter 123 of the one or more sidewalls 125 at least partially between the top region 124 and the bottom region 134 of the canister 114. The helical body 220 may be sized such that the outer periphery 225 interfaces or is adjacent to the inner perimeter 123, or is spaced from the inner perimeter 123 of the canister 114. For example, the canister 114 may include a frustoconical shape that narrows between the top region 124 and the bottom region 134. The plate 210 may be substantially circular and the helical body 220 may include a width that decreases as the helical body 220 increases in distance from the plate 210, generally complementary to the narrowing of the canister 114 (e.g., the width or diameter of the helical body 220 at the distal end 222 is less than the width or diameter of the helical body 220 at the top end proximate to the plate 210). In some embodiments, the plate 210 may include a shape other than a circle, such as an oval, a triangle, a rectangle, a pentagon, a hexagon, etc. A top or bottom profile of the helical body 220 also may include a shape other than a circle, such as an oval, a triangle, a rectangle, a pentagon, a hexagon, etc. The shape of the plate 210 and/or the helical body 220 may be generally complementary to the shape of the container 114.

In some embodiments, the plate 210 may include four theoretical quadrants 211 or regions of substantially equal dimensions, and the plurality of holes 212 may be positioned on the plate 210 such that at least one hole 212 of the plurality of holes 212 is positioned within each quadrant 211 of the plate 210. In some embodiments, the plurality of holes 212 may be positioned on the plate 210 such that multiple holes 212 of the plurality of holes 212 are positioned within each quadrant 211 of the plate 210.

The plate 210 also may define an opening 232 positioned on the plate 210 to generally align with and/or be positioned directly below the vacuum port 129 on the lid 119 when the lid 119 is secured to the canister 114. For example, the vacuum port 129 may be positioned generally centrally on the lid 119 and the opening 232 may be positioned generally centrally on the plate 210. In some embodiments, the vacuum port 129 may be positioned off-center on the lid 119 and the opening 232 may be positioned to align with or be directly below the vacuum port 129 when the vacuum port 129 is off-center. The opening 232 may allow the necessary air in the canister 114 to be available for suction by the pump 116 through the vacuum port 129 when the pump 116 is activated. In some embodiments, the opening 232 has an area or diameter greater than an area or diameter of each hole 212 of the plurality of holes 212. The plate 210 also may include a lip 230 at least partially defining the opening 232 and extending from the plate 210 distal to the helical body 220.

The plate 210 also may be spaced from the lid 119 when the baffle structure 200 is positioned in the interior region of the canister 114. For example the plate 210 may be spaced about 0.64 cm to about 5.1 cm from lid 119, about 1.3 cm to about 2.5 cm from the lid 119, about 2.5 cm to about 3.8 cm from the lid 119, about 3.8 cm to about 5.1 cm from the lid 119, about 0.64 cm to about 1.3 cm from lid 119, about 1.3 cm to about 1.9 cm from lid 119, about 1.9 cm to about 2.5 cm from the lid 119, about 2.5 cm to about 3.2 cm from the lid 119, about 3.2 cm to about 3.8 cm from the lid 119, about 3.8 cm to about 4.4 cm from the lid 119, about 4.4 cm to about 5.1 cm from the lid 119, less than about 5.1 cm from the lid 119, less than about 3.8 cm from the lid 119, less than about 2.5 cm from the lid 119, less than about 1.9 cm from the lid 119, or less than about 1.3 cm from the lid 119.

In use, when urine or other fluid enters the interior region of the canister 114 through the urine port 139 on the lid 119, the urine only falls a short distance (e.g., distance that is less than a distance to the bottom of the canister and/or distance that is less than a distance until the urine level in the canister 114) until the urine contacts the plate 210 of the baffle structure 200. The urine may then fall through one or more holes of the plurality of holes 212 and fall a short distance until the urine contacts the helical body 220. The urine may then continue to flow down the helical body 220 until the urine reaches the bottom of the canister 114 or the urine level in the canister. At least one, some, or all embodiments of the baffle structure 200, then, results in the technical effect of reducing the distance of freefall of urine in entering the canister 114 and/or moving through the canister, thus reducing or preventing a splashing noise in the canister 114 as the urine is collected. The baffle structure 200 also may prevent sloshing and splashing of urine held in the canister 114 as the canister 114 is moved.

Figure 3A:
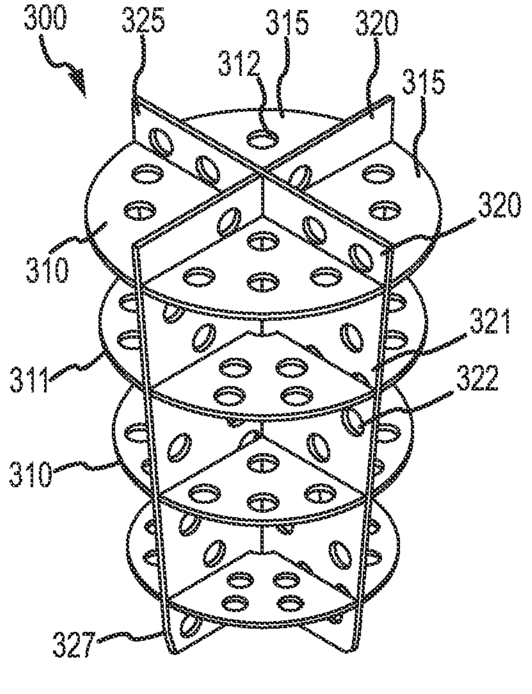
FIG. 3A is a side isometric view of a horizontal transverse baffle structure for a urine collection system, according to an embodiment.
Figure 3B:
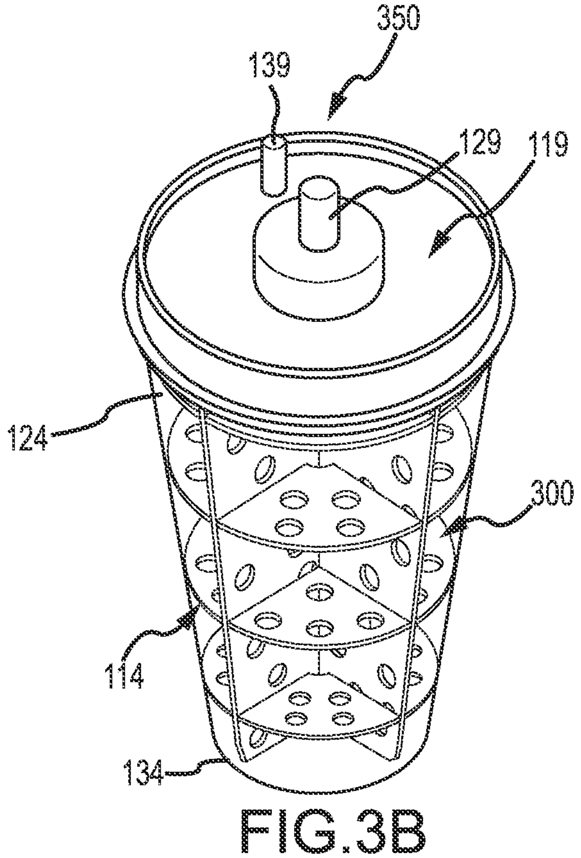
FIG. 3B is a side isometric view of a urine collection container including a canister, a lid, and the horizontal transverse baffle structure of FIG. 3A positioned in a urine collection container, according to an embodiment.

FIG. 3A is an isometric side view of a horizontal transverse baffle structure 300 and FIG. 3B is an isometric view of a urine collection container 350 including the baffle structure 300 positioned in the canister 114 and the lid 119 secured to the top region 124 of the canister 114, according to an embodiment. The baffle structure 300 may include one or more baffles. For example, the one or more baffles of the baffle structure 300 may include one or more (e.g., two, three, four, five, six, etc.) walls 320 and a plurality of a plates 310 secured and spaced along the one or more walls 320. Each plate 310 of the plurality of plates 310 may include a plurality of holes 312. In some embodiments, the plurality of plates 310 includes at least a top plate, a bottom plate, and one or more (e.g., two, three, four, etc.) intermediate plates positioned between the top plate and the bottom plate.

The one or more walls 320 may be positioned and/or secured to the plurality of plates 310 to divide each plate of the plurality of plates 310 into multiple plate regions 315. For example, the baffle structure 300 includes four walls 320 that divide each plate 310 into four different plate regions 315. At least one hole 312 of the plurality of holes 312 may be positioned in each plate region 312 of the multiple plate regions 315. In some embodiments, multiple holes 312 may be positioned in each plate region 315 of the multiple plate regions 315. The multiple holes 312 in each plate region 315 may be positioned such that alignment of the multiple holes 312 on adjacent plates 310 is absent (e.g., the multiple holes 312 in each plate region 315 are not aligned with the multiple holes 312 in each plate region 315 of an adjacent plate 310, or the multiples holes 312 in each plate region 314 are misaligned with the multiple holes 312 in each plate region 315 of an adjacent plate 310). For example, the multiple holes 312 on the top plate 310 may be arranged in a generally triangular or diamond formation, and the multiple holes 312 on the intermediate plate 310 adjacent to the top plate 310 may be arranged in a generally square formation. In any event, each hole of the plurality of holes 312 may not be aligned with any holes of the plurality of holes 312 on an adjacent plate.

In some embodiments, one or more (e.g., some or all) walls 320 of the multiple of walls 320 may include a plurality of holes 322. For example, the plurality of plates 310 may divide each wall 320 of the multiple walls 320 into multiple wall regions 321. One or more holes 322 of the plurality of holes 322 may be positioned in each wall region 321 of the multiple wall regions 321. In some embodiments, one or more (e.g., all) walls 320 of the multiple walls 320 includes a top portion 325 extending above the top plate of the plurality of plates 310 and a bottom portion 327 extending below the bottom plate of the plurality of plates 310. At least one (e.g., both) of the top portion 325 and the bottom portion 327 may include at least one hole 322 of the plurality of holes.

Turning to FIG. 3B, in some embodiments, the baffle structure 300 is removably positionable in the interior region of the canister 114. When positioned in the interior region of the canister 114, the top plate of the plurality of plates 310 is positioned proximate to the top region 124 and the bottom plate of the plurality of plates 310 is positioned proximate to the bottom region 134 of the canister 114. The plurality of plates 310 may include an outer periphery 311 generally complementary to the inner perimeter 123 of the one or more sidewalls 125 of the canister 114 when the baffle structure 300 is positioned in the interior region of the canister 114. In some embodiments, the canister 114 includes a frustoconical shape that narrows between the top region 124 and the bottom region 134. Each plate of the plurality of plates 310 may be substantially circular, with the top plate having a diameter greater than a diameter of the bottom plate. The urine collection container 350 may include the lid 119 removably secured or securable to the canister 114 with the baffle structure 300 positioned in the interior region of the canister 114. In some embodiments, the plurality of plates 310 may include a shape other than a circle, such as an oval, a triangle, a rectangle, a pentagon, a hexagon, etc. The shape of the plurality of plates 310 may be generally complementary to the shape of the container 114.

In use, urine entering the canister may fall only a short distance before contacting the top plate of the plurality of plates 310. The urine may then pass through one or more holes of the plurality of holes 312 on the top plate and fall another short distance before contacting the adjacent intermediate plate of the plurality of plates 310. The urine may then pass through one or more holes of the plurality of holes 312 on the adjacent intermediate plate of the plurality of plates 310 and fall another short distance before contacting an adjacent plate of the plurality of plates 310, and so one. In at least one, some, or all embodiments, the plurality of plates 310, then, result in the technical effect of reducing the distance of freefall of urine in entering the canister 114 and/or moving through the canister 114, thus reducing or preventing a splashing noise in the canister 114 as the urine is collected. The walls 320 also prevent or inhibit sloshing and splashing noises of urine in the canister 114 as the canister is moved.

Urine collection systems including no baffle structure, the baffle structure 200, and the baffle structure 200 were tested comparatively to determine the effect of the baffle structures 200, 300 on the noise generated during urine collection and movement of the canister 114. It was observed that the baffle structures 200, 300 decreased splashing noises during filling of the canister 114 by reducing distance of fluid freefall into pooled liquid collected in the canister 114.

Figure 4:
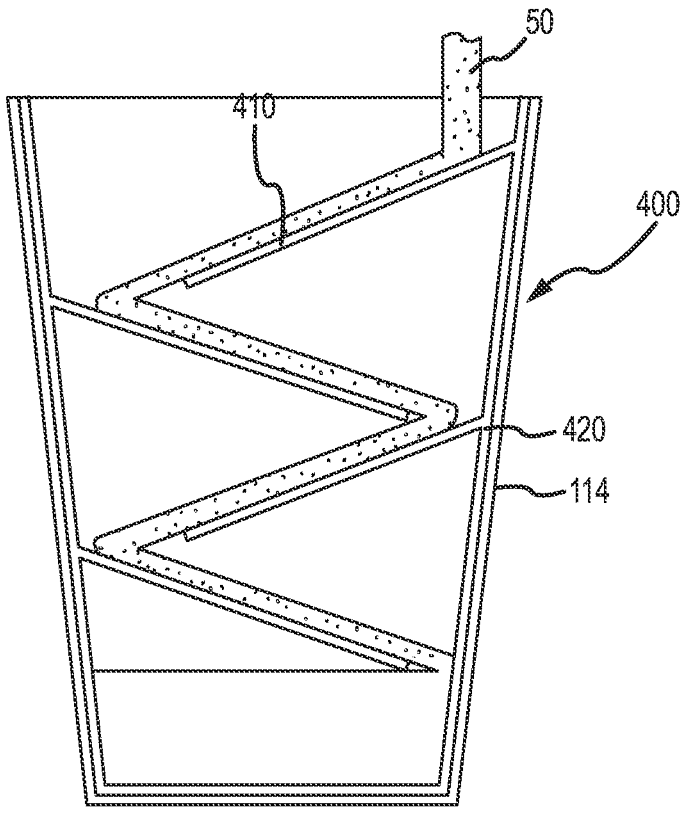
FIG. 4 is a side view of a baffle structure in a canister of a urine collection system, according to an embodiment.

Turning to FIG. 4, the canister 114 is shown with a baffle structure 400 positioned in the interior region of the canister 114, according to an embodiment. Although the canister 114 is shown without the lid 119, the lid 119 may be secured to the canister with the baffle structure 400 positioned therein effective to form a urine collection container including the baffle structure 400. In some embodiments, the baffle structure 400 includes a plurality downward sloping walls 410 that partially overlap with an adjacent wall of the plurality of downward sloping walls 410. As urine 50 enters the interior region of the canister 114, the urine 50 may first contact a top downward sloping wall of the plurality of downward sloping walls. The urine 50 may then flow to the end of the top downward sloping wall and fall to an adjacent downward sloping wall of the plurality of downward sloping walls 410. The urine may then flow down to the end of the adjacent downward sloping wall and fall onto an additional adjacent downward sloping wall of the plurality of downward sloping walls 410 below the adjacent downward sloping wall. This process may continue through the plurality of downward sloping wall 410 until the urine 50 reaches the bottom of the canister 114 and/or the level of urine 50 held in the canister 114. The plurality of downward sloping walls 410 may be positioned such there is no empty space in the canister 114 extending continuously from the top of the interior region to the bottom of the interior region.

In some embodiments, the baffle structure 400 may be removably positionable or positioned in the interior region of the canister and may include one or more a supports 420. The plurality of downward sloping walls 410 may extending inward and downward from the one or more supports 420 when the baffle structure 400 is positioned in the interior region of the canister 114.

Figure 5:
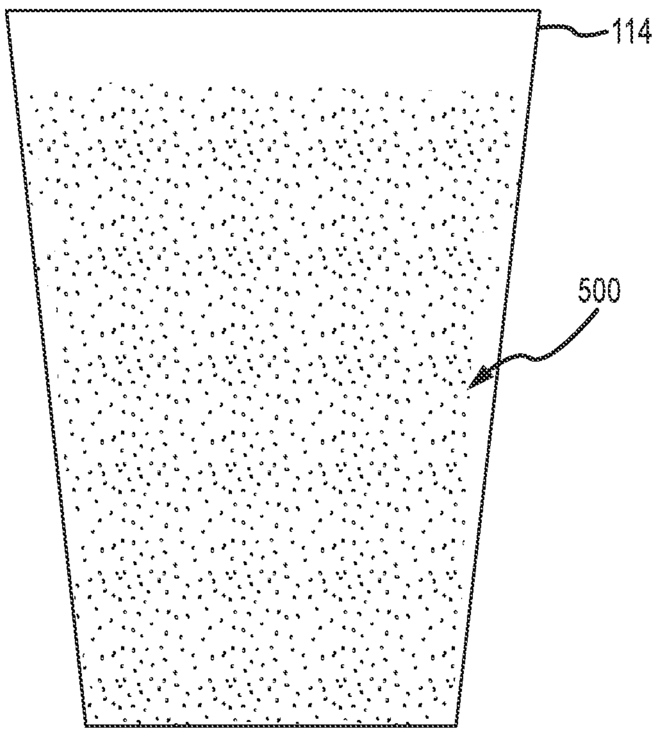
FIG. 5 is a side view of a baffle structure in a canister of a urine collection system, according to an embodiment.

Turning to FIG. 5, in some embodiments a baffle structure may include a plurality of beads 500 positioned or positionable in the interior region of the canister 114. The plurality of beads 500 may be one or more of silica beads, glass beads, carbon beads, carbon beads, clay beads, other desiccant beads, other structures such as shavings or helical pieces of material, or combinations thereof. The plurality of beads 500 may be positioned in the interior region of the canister 114 to a predetermined or desired level.

Figure 6:
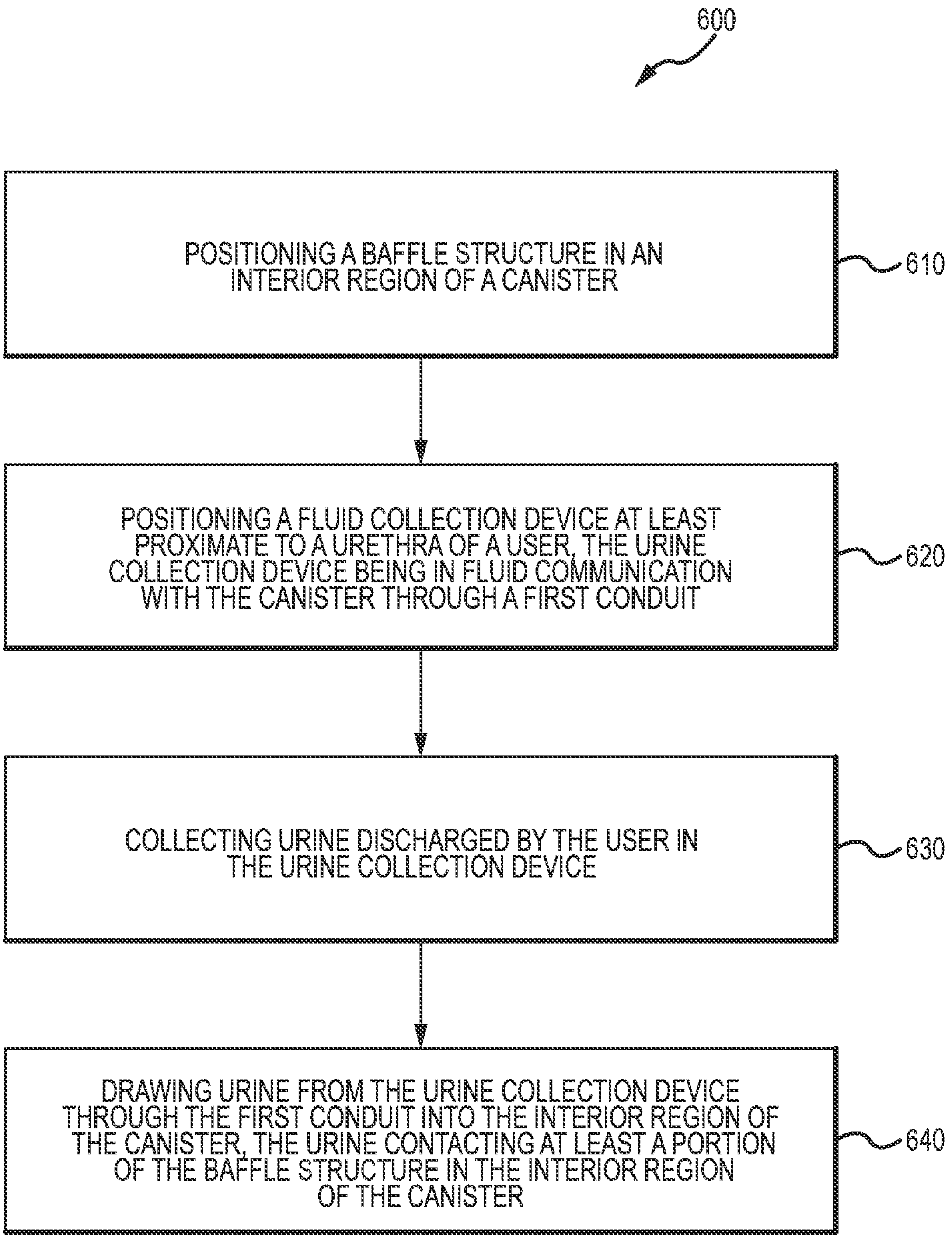
FIG. 6 is a flow diagram of a method for collecting fluid, according to an embodiment.

FIG. 6 is a flow diagram of a method 600 for collecting fluid, according to an embodiment. The method 600 includes an act 610 of positioning a baffle structure having one or more baffles in an interior region of a canister. In some embodiments, the method 600 includes an act 620 of positioning a fluid collection device at least proximate to a urethra of a user, the urine collection device being in fluid communication with the canister through a first conduit. In some embodiments, the method 600 includes an act 630 of collecting urine discharged by the user in the urine collection device. In some embodiments, the method 600 includes an act 640 of drawing urine from the urine collection device through the first conduit into the interior region of the canister, the urine contacting at least a portion of the baffle structure in the interior region of the canister.

The baffle structure in the method 600 may include any baffle structure described herein. In some embodiments, the one or baffles of the baffle structure of the method 600 may include a plate having a plurality of holes and a helical body secured to the plate and the act 610 includes positioning the plate proximate to a top region of the canister with the helical body extending at least partially between the top region and a bottom region of the canister. In some embodiments, the one or more baffles of the baffle structure of the method 600 may include one or more walls and a plurality of a plates secured and spaced along the one or more walls, each plate of the plurality of plates including a plurality of holes. The act 610 may include positioning a top plate of the plurality of plates proximate to a top region of the canister and a bottom plate of the plurality of plates proximate to a bottom region of the canister.

The acts of the method 600 described above are for illustrative purposes. For example, the acts of the method 600 can be performed in different orders, split into multiple acts, modified, supplemented, or combined. In an embodiment, one or more of the act of the method 600 can be omitted from the method 600. Any of the acts of the method 600 can include using any of the baffle structures disclosed herein.

As used herein, the term "about" or "substantially" refers to an allowable variance of the term modified by "about" or "substantially" by +10% or +5%. Further, the terms "less than," "or less," "greater than," "more than," or "or more" include, as an endpoint, the value that is modified by the terms "less than," "or less," "greater than," "more than," or "or more."

While various aspects and embodiments have been disclosed herein, other aspects and embodiments are contemplated. The various aspects and embodiments disclosed herein are for purposes of illustration and are not intended to be limiting.

What is claimed is:

1. A urine collection system, comprising:

a urine collection device configured to be positioned at least proximate to a urethra of a user;

a first conduit in fluid communication with the urine collection device;

a canister having a top region, a bottom region, and one or more sidewalls extending at least partially between the top region and the bottom region and including an inner perimeter that defines an interior region of the canister in fluid communication with the first conduit; and a baffle structure positioned or positionable in the interior region of the canister, the baffle structure including one or more plates having a plurality of holes extending therethrough and an outer periphery shaped generally complementary to the inner perimeter of the one or more sidewalls of the canister, wherein the one or more plates include at least a top plate positioned at least proximate to the top region of the canister when the baffle structure is positioned in the interior region of the canister.

2. The urine collection system of claim 1, wherein:

the baffle structure is removably positioned in the interior region of the canister and includes the top plate having the plurality of holes and a helical body secured to the top plate, the helical body extending at least partially between the top region and the bottom region and including an outer periphery generally complementary to the inner perimeter of the one or more sidewalls at least partially between the top region and the bottom region;

the canister includes a frustoconical shape that narrows between the top region and the bottom region;

the top plate is substantially circular; and the helical body includes a width that decreases as the helical body increases in distance from the top plate.

3. The urine collection system of claim 1, wherein the plurality of holes in the top plate are positioned on the top plate such that at least one hole of the plurality of holes is positioned within each quadrant of the top plate.

4. The urine collection system of claim 1, wherein the top plate defines an opening having an area or diameter greater than an area or diameter of each hole of the plurality of holes.

5. The urine collection system of claim 4, wherein the top plate includes a lip at least partially defining the opening.

6. The urine collection system of claim 4, further comprising a lid removably secured or securable to the canister and having a collection port in fluid communication with the first conduit and a vacuum port configured to provide fluid communication between a vacuum source and the interior region of the canister via a second conduit.

7. The urine collection system of claim 6, wherein the top plate is spaced from the lid and the vacuum port and the opening in the top plate are substantially aligned with the vacuum port positioned over the opening in the top plate when the baffle structure is positioned in the interior region and the lid is secured to the canister.

8. The urine collection system of claim 7, wherein the vacuum port is positioned generally centrally on the lid and the opening is positioned generally centrally on the top plate.

9. The urine collection system of claim 1, wherein the baffle structure is removably positioned in the interior region of the canister and includes one or more walls and a plurality of plates secured and spaced along the one or more walls, the plurality of plates including the top plate and one or more additional plates, each plate of the plurality of plates including the plurality of holes.

10. The urine collection system of claim 9, wherein:

the plurality of plates includes at least the top plate, a bottom plate, and one or more intermediate plates positioned between the top plate and the bottom plate; and the one or more walls include multiple walls positioned to divide each plate of the plurality of plates into multiple plate regions.

11. The urine collection system of claim 10, wherein each plate of the plurality of plates includes at least one hole of the plurality of holes positioned in each plate region of the multiple plate regions.

12. The urine collection system of claim 11, wherein each plate of the plurality of plates includes multiple holes of the plurality of holes positioned in each plate region of the multiple plate regions, the multiples holes being positioned such that alignment of the multiple holes on adjacent plates of the plurality of plates is absent.

13. The urine collection system of claim 10, wherein each wall of the multiple walls includes a plurality of holes.

14. The urine collection system of claim 13, wherein:

the plurality of plates divide each wall of the multiple walls into multiple wall regions; and one or more holes of the plurality of holes on each wall of the multiple walls are positioned in each wall region of the multiple wall regions.

15. The urine collection system of claim 10, wherein each wall of the multiple walls includes a top portion extending above the top plate and a bottom portion extending below the bottom plate.

16. The urine collection system of claim 15, wherein the top portion and the bottom portion of each wall of the multiple walls each include at least one hole.

17. The urine collection system of claim 10, wherein:

the canister includes a frustoconical shape that narrows between the top region and the bottom region;

each plate of the plurality of plates is substantially circular; and the top plate includes a diameter greater than a diameter of the bottom plate.

18. The urine collection system of claim 1, further comprising a lid removably secured or securable to the canister and having a collection port in fluid communication with the first conduit and a vacuum port configured to provide fluid communication between a vacuum source and the interior region of the canister via a second conduit.

19. The urine collection system of claim 1, further comprising a pump in fluid communication with the canister and configured to pull an at least partial vacuum on the interior region of the canister effective to draw urine from the urine collection device through the first conduit into the canister.

20. A urine collection container, comprising:

a canister having a top region, a bottom region, and one or more sidewalls extending at least partially between the top region and the bottom region and including an inner perimeter that defines an interior region of the canister;

a baffle structure positioned or positionable in the interior region of the canister, the baffle structure including one or more plates having a plurality of holes extending therethrough and an outer periphery shaped generally complementary to the inner perimeter of the one or more sidewalls of the canister, wherein the one or more plates include at least a top plate positioned at least proximate to the top region of the canister when the baffle structure is positioned in the interior region of the canister; and a lid secured or securable to the canister, the lid including a collection port and a vacuum port.

21. The urine collection container of claim 20, wherein:

the baffle structure is removably positioned in the interior region of the canister and includes the top plate having the plurality of holes and a helical body secured to the top plate, the helical body extending at least partially between the top region and the bottom region and including an outer periphery generally complementary to the inner perimeter of the one or more sidewalls at least partially between the top region and the bottom region;

the canister includes a frustoconical shape that narrows between the top region and the bottom region;

the top plate is substantially circular; and the helical body includes a width that decreases as the helical body increases in distance from the top plate.

22. The urine collection container of claim 20, wherein the plurality of holes in the top plate are positioned on the top plate such that at least one hole of the plurality of holes is positioned within each quadrant of the plate.

23. The urine collection container of claim 20, wherein the top plate defines an opening having an area or diameter greater than an area or diameter of each hole of the plurality of holes.

24. The urine collection container of claim 23, wherein the top plate includes a lip at least partially defining the opening.

25. The urine collection container of claim 24, wherein the top plate is spaced from the lid and the vacuum port and the opening in the top plate are substantially aligned with the vacuum port positioned over the opening in the top plate when the baffle structure is positioned in the interior region and the lid is secured to the canister.

26. The urine collection container of claim 25, wherein the vacuum port is positioned generally centrally on the lid and the opening is positioned generally centrally on the top plate.

27. The urine collection container of claim 20, wherein the baffle structure is removably positioned in the interior region of the canister and includes one or more walls and a plurality of plates secured and spaced along the one or more walls, the plurality of plates including the top plate and one or more additional plates, each plate of the plurality of plates including the plurality of holes.

28. The urine collection container of claim 27, wherein:

the plurality of plates includes at least the top plate, a bottom plate, and one or more intermediate plates positioned between the top plate and the bottom plate; and the one or more walls include multiple walls positioned to divide each plate of the plurality of plates into multiple plate regions.

29. The urine collection container of claim 28, wherein each plate of the plurality of plates includes at least one hole of the plurality of holes positioned in each plate region of the multiple plate regions.

30. The urine collection container of claim 29, wherein each plate of the plurality of plates includes multiple holes of the plurality of holes positioned in each plate region of the multiple plate regions, the multiples holes being positioned such that alignment of the multiple holes on adjacent plates of the plurality of plates is absent.

31. The urine collection container of claim 28, wherein each wall of the multiple walls includes a plurality of holes.

32. The urine collection container of claim 31, wherein:

the plurality of plates divide each wall of the multiple walls into multiple wall regions; and one or more holes of the plurality of holes on each wall of the multiple walls are positioned in each wall region of the multiple wall regions.

33. The urine collection container of claim 28, wherein each wall of the multiple walls includes a top portion extending above the top plate and a bottom portion extending below the bottom plate.

34. The urine collection container of claim 33, wherein the top portion and the bottom portion of each wall of the multiple walls each include at least one hole.

35. The urine collection container of claim 28, wherein:

the canister includes a frustoconical shape that narrows between the top region and the bottom region;

each plate of the plurality of plates is substantially circular; and the top plate includes a diameter greater than a diameter of the bottom plate.

36. A method of collecting fluid, the method comprising:

positioning a baffle structure in an interior region of a canister, the baffle structure including one or more plates having a plurality of holes extending therethrough and an outer periphery shaped generally complementary to an inner perimeter of one or more sidewalls of the canister, wherein the one or more plates include at least a top plate positioned at least proximate to the top region of the canister;

positioning a fluid collection device at least proximate to a urethra of a user, the urine collection device being in fluid communication with the canister through a first conduit;

collecting urine discharged by the user in the urine collection device; and drawing urine from the urine collection device through the first conduit into the interior region of the canister, the urine contacting at least a portion of the one or more baffles in the interior region of the canister.

37. The method of claim 36, wherein the baffle structure includes the plate having the plurality of holes and a helical body secured to the plate and positioning a baffle structure in an interior region of a canister includes positioning the plate proximate to a top region of the canister with the helical body extending at least partially between the top region and a bottom region of the canister.

38. The method of claim 36, wherein the baffle structure includes one or more walls and a plurality of plates secured and spaced along the one or more walls, the plurality of plates including the top plate and one or more additional plates, each plate of the plurality of plates including the plurality of holes, and wherein positioning a baffle structure in an interior region of a canister includes positioning the top plate of the plurality of plates proximate to a top region of the canister and a bottom plate of the plurality of plates proximate to a bottom region of the canister.

* * * * *